US009709891B2

(12) United States Patent
Kanda et al.

(10) Patent No.: US 9,709,891 B2
(45) Date of Patent: *Jul. 18, 2017

(54) POSITIVE RESIST COMPOSITION, RESIN USED FOR THE POSITIVE RESIST COMPOSITION, COMPOUND USED FOR SYNTHESIS OF THE RESIN AND PATTERN FORMING METHOD USING THE POSITIVE RESIST COMPOSITION

(71) Applicant: FUJIFILM Corporation, Minato-ku, Tokyo (JP)

(72) Inventors: Hiromi Kanda, Shizuoka (JP); Shinichi Kanna, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 18 days.

This patent is subject to a terminal disclaimer.

(21) Appl. No.: 14/633,729

(22) Filed: Feb. 27, 2015

(65) Prior Publication Data

US 2015/0168838 A1 Jun. 18, 2015

Related U.S. Application Data

(63) Continuation of application No. 14/158,490, filed on Jan. 17, 2014, which is a continuation of application No. 11/636,482, filed on Dec. 11, 2006, now Pat. No. 8,679,724.

(30) Foreign Application Priority Data

Dec. 9, 2005 (JP) ................................. 2005-356717
Apr. 10, 2006 (JP) ................................. 2006-107728
Jul. 19, 2006 (JP) ................................. 2006-196856

(51) Int. Cl.
*G03F 7/039* (2006.01)
*G03F 7/004* (2006.01)
*G03F 7/075* (2006.01)
*G03F 7/20* (2006.01)
*G03F 7/30* (2006.01)
*G03F 7/32* (2006.01)
*C07C 69/653* (2006.01)

(52) U.S. Cl.
CPC .......... *G03F 7/0397* (2013.01); *C07C 69/653* (2013.01); *G03F 7/0045* (2013.01); *G03F 7/0046* (2013.01); *G03F 7/039* (2013.01); *G03F 7/0392* (2013.01); *G03F 7/0395* (2013.01); *G03F 7/0757* (2013.01); *G03F 7/0758* (2013.01); *G03F 7/2041* (2013.01); *G03F 7/30* (2013.01); *G03F 7/322* (2013.01)

(58) Field of Classification Search
None
See application file for complete search history.

(56) References Cited

U.S. PATENT DOCUMENTS

| 2,472,811 | A | 6/1949 | Dickey |
| 4,613,657 | A | 9/1986 | Narita et al. |
| 6,210,856 | B1 | 4/2001 | Lin et al. |
| 6,391,514 | B1 | 5/2002 | Eilbeck et al. |
| 7,285,373 | B2 | 10/2007 | Lim et al. |
| 7,611,820 | B2 * | 11/2009 | Kanda .................... G03F 7/0045 430/270.1 |
| 7,635,554 | B2 * | 12/2009 | Fukuhara ............... G03F 7/0045 430/270.1 |
| 7,700,260 | B2 * | 4/2010 | Kanna .................... G03F 7/0046 430/270.1 |
| 7,811,740 | B2 | 10/2010 | Kanda et al. |
| 8,389,200 | B2 * | 3/2013 | Kanna .................... G03F 7/0046 430/270.1 |
| 8,697,329 | B2 * | 4/2014 | Kanda .................... G03F 7/0046 430/270.1 |
| 8,771,916 | B2 * | 7/2014 | Hirano ................ C07D 307/93 430/270.1 |
| 9,034,558 | B2 * | 5/2015 | Yamaguchi ............. C08F 12/20 430/270.1 |
| 2003/0170561 | A1 | 9/2003 | Iwasawa et al. |
| 2003/0186160 | A1 | 10/2003 | Ito |
| 2004/0005512 | A1 | 1/2004 | Mizutani et al. |
| 2004/0053160 | A1 | 3/2004 | Takahashi et al. |
| 2004/0058269 | A1 | 3/2004 | Hada et al. |
| 2004/0116750 | A1 | 6/2004 | Koboyashi et al. |
| 2004/0197707 | A1 | 10/2004 | Yamanaka et al. |
| 2004/0242821 | A1 | 12/2004 | Hatakeyama et al. |
| 2004/0259028 | A1 * | 12/2004 | Sato ...................... G03F 7/0397 430/270.1 |
| 2005/0019690 | A1 | 1/2005 | Kodama |

(Continued)

FOREIGN PATENT DOCUMENTS

| EP | 1 517 179 A1 | 3/2005 |
| EP | 1 566 693 A2 | 8/2005 |

(Continued)

OTHER PUBLICATIONS

JPO English abstract for JP2005-221960 (2005).*
Machine-assisted English translation for JP2005-221960 provided by JPO (2005).*
Office Action dated Feb. 16, 2015 issued by the Korean Intellectual Property Office in counterpart Korean Patent Application No. 10-2014-0021173.
Office Action issued on Oct. 12, 2015, by the European Patent Office in counterpart European Application No. 06025353.1.
Database WPI Week 198024, Derwent Publications Ltd., London, (Continued)

*Primary Examiner* — Sin Lee
(74) *Attorney, Agent, or Firm* — Sughrue Mion, PLLC

(57) ABSTRACT

A positive resist composition comprises: (A) a resin of which solubility in an alkali developer increases under an action of an acid; (B) a compound capable of generating an acid upon irradiation with actinic rays or radiation; (C) a resin having at least one of a fluorine atom and a silicon atom; and (D) a solvent; and a pattern forming method using the positive resist composition.

24 Claims, 1 Drawing Sheet

(56) References Cited

U.S. PATENT DOCUMENTS

| | | | |
|---|---|---|---|
| 2005/0026074 A1 | 2/2005 | Inabe et al. | |
| 2006/0008736 A1 | 1/2006 | Kanda et al. | |
| 2006/0078823 A1* | 4/2006 | Kanda | G03F 7/0046 430/270.1 |
| 2006/0246073 A1 | 11/2006 | Knight et al. | |
| 2006/0246373 A1 | 11/2006 | Wang | |
| 2006/0292490 A1 | 12/2006 | Kodama et al. | |
| 2007/0059639 A1* | 3/2007 | Kanda | G03F 7/0045 430/270.1 |
| 2007/0254235 A1* | 11/2007 | Allen et al. | 430/270.1 |
| 2010/0297553 A1* | 11/2010 | Kanda | G03F 7/0046 430/270.1 |

FOREIGN PATENT DOCUMENTS

| | | |
|---|---|---|
| EP | 1 580 598 A2 | 9/2005 |
| EP | 1 645 908 A1 | 4/2006 |
| EP | 1 720 072 A1 | 11/2006 |
| EP | 1 764 652 A2 | 3/2007 |
| EP | 1 367 440 B1 | 9/2011 |
| JP | 57-153433 A | 9/1982 |
| JP | 60-042411 A | 3/1985 |
| JP | 7-220990 A | 8/1995 |
| JP | 10-303114 A | 11/1998 |
| JP | 10-309455 A | 11/1998 |
| JP | 2002-90991 A | 3/2002 |
| JP | 2003-173027 A | 6/2003 |
| JP | 2004-271844 A | 9/2004 |
| JP | 2004-294688 A | 10/2004 |
| JP | 2005-91713 | 4/2005 |
| JP | 2005-99156 A | 4/2005 |
| JP | 2005-221714 A | 8/2005 |
| JP | 2005-221960 * | 8/2005 |
| JP | 2005-234330 A | 9/2005 |
| TW | 1227376 | 4/1993 |
| TW | 200508801 | 3/2005 |
| WO | 2004-068242 A1 | 8/2004 |

OTHER PUBLICATIONS

GB (XP-002479594) Abstract of JP 55-060609, (1980).
JPO English abstract for JP 55-60509 (Saeki), (1980).
Office Action dated Nov. 8, 2012 in Taiwanese Patent Application No. 095145560.
Office Action dated Jul. 4, 2013 in corresponding Taiwan Application No. 095145560.
Ito et al ("Radical Copolymerization of 2-Trifluoromethylacrylic Monomers. II. Kinetics, Monomer Reactivities, an Penultimate Effect in Their Copolymerization with Norbornenes and Vinyl Ethers", Journal of Polymer Science Part A: Polymer Chemistry, vol. 42 (6), pp. 1478-1505. (2004).
Extended European Search Report dated May 23, 2008 in European Application No. 06025353.1.
J.A. Hoffnagle, et al., "Liquid Immersion Deep-Ultraviolet Interferometric Lithography", American Vacuum Society 1999, pp. 3306-3309.
B. J. Lin "Semiconductor Foundry, Lithography, and Partners", Micropatterning Division, TSMC, Inc. Emerging Lithographic Technologies VI, pp. 11-24, (2002).
Notification of Reasons for Refusal dated Jul. 21, 2011, in Japanese Application No. 2006-331641.
Notice of Submission of Opinion dated Dec. 24, 2013, issued by the Korean Intellectual Property Office in Korean Application No. 10-2006-0124415.
Office Action dated May 13, 2014 in Korean Application No. 10-2014-0021173.
Office Action dated Jun. 24, 2014 issued by the Korean Intellectual Property Office in Korean Patent Application No. 10-2006-0124415.
Office Action dated Jul. 3, 2014 Issued by the European Patent Office in European Patent Application No. 06025353.1.
Office Action dated Nov. 25, 2014 issued by Korean Intellectual Property Office in Korean Patent Application No. 10-2014-0021173.
Derwent English abstract for JP2005-91713 (2005).
Office Action dated Jun. 13, 2016 issued by the European Patent Office in counterpart European Patent Application No. 06025353.1.
Office Action dated Mar. 23, 2017 issued by the European Patent Office in counterpart European Patent Application No. 06025353.1.

* cited by examiner

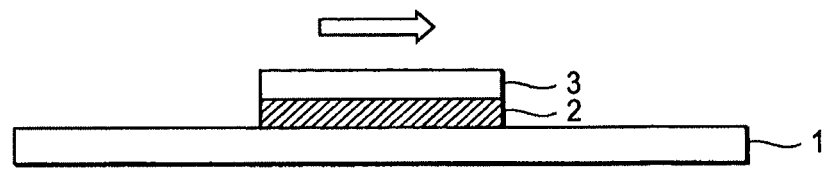

… (US 9,709,891 B2)

POSITIVE RESIST COMPOSITION, RESIN USED FOR THE POSITIVE RESIST COMPOSITION, COMPOUND USED FOR SYNTHESIS OF THE RESIN AND PATTERN FORMING METHOD USING THE POSITIVE RESIST COMPOSITION

This is a Continuation Application of application Ser. No. 14/158,490, filed Jan. 17, 2014, which is a Continuation Application of application Ser. No. 11/636,482, filed Dec. 11, 2006 (now U.S. Pat. No. 8,679,724, issued Mar. 25, 2014), which claims priority under 35 U.S.C. §119 from JP 2005-356717, filed Dec. 9, 2005, JP 2006-107728, filed Apr. 10, 2006 and JP 2006-196856 filed Jul. 19, 2006, the disclosures of which are incorporated herein by reference.

BACKGROUND

1. Field of the Invention

The present invention relates to a positive resist composition for use in the production process of a semiconductor such as IC, in the production of a circuit substrate of liquid crystal, thermal head or the like, and in the lithography process of other photo-applications; a resin used for the positive resist composition; a compound used for the synthesis of the resin; and a pattern forming method using the positive resist composition. More specifically, the present invention relates to a positive resist composition suitable for exposure by an immersion-type projection exposure apparatus using a light source of emitting far ultraviolet light at a wavelength of 300 nm or less; a resin used for the positive resist composition; a compound used for the synthesis of the resin; and a pattern forming method using the positive resist composition.

2. Description of the Related Art

Along with the miniaturization of semiconductor devices, the trend is moving into shorter wavelength of the exposure light source and higher numerical aperture (high NA) of the projection lens. At present, an exposure machine with NA of 0.84 has been developed, where an ArF excimer laser having a wavelength of 193 nm is used as the light source. As commonly well known, these can be expressed by the following formulae:

(Resolving power)$=k_1 \cdot (\lambda/\mathrm{NA})$ (Focal depth)$=\pm k_2 \cdot \lambda/\mathrm{NA}^2$ wherein $\lambda$ is the wavelength of the exposure light source, NA is the numerical aperture of the projection lens, and $k_1$ and $k_2$ are constants related to the process.

In order to realize still shorter wavelength and higher resolving power, studies are being made on an exposure machine where an $F_2$ excimer laser having a wavelength of 157 nm is used as the light source. However, the lens material used for the exposure apparatus so as to realize shorter wavelength and the material used for the resist are very limited and therefore, it is extremely difficult to stabilize the production cost or quality of the apparatus and materials. This may lead to a failure in procuring the exposure apparatus and the resist each assured of sufficiently high performance and stability within a required time period.

Conventionally, a so-called immersion method of filling a high refractive-index liquid (hereinafter sometimes referred to as an "immersion liquid") between the projection lens and the sample has been known as a technique of increasing the resolving power in an optical microscope.

As for the "effect of immersion", assuming that the wavelength of exposure light in air is $\lambda_0$, the refractive index of the immersion liquid to air is n, the convergence half-angle of beam is $\theta$ and $\mathrm{NA}_0 = \sin\theta$, the above-described resolving power and focal depth when immersed can be expressed by the following formulae:

(Resolving power)$=k_1 \cdot (\lambda_0/n)/\mathrm{NA}_0$ (Focal depth)$=\pm k_2 \cdot (\lambda_0/n)/\mathrm{NA}_0^2$ That is, the effect of immersion is equal to use of an exposure wavelength of 1/n. In other words, in the case of a projection optical system with the same NA, the focal depth can be made n times larger by the immersion. This is effective for all pattern profiles and can be combined with super-resolution techniques such as phase-shift method and modified illumination method which are being studied at present.

Examples of the apparatus where this effect is applied to the transfer of a fine image pattern of a semiconductor device are described in JP-A-57-153433 (the term "JP-A" as used herein means an "unexamined published Japanese patent application")) and JP-A-7-220990.

Recent progress of the immersion exposure technique is reported, for example, in SPIE Proc., 4688, 11 (2002), J. Vac. Sci. Tecnol. B, 17 (1999), SPIE Proc., 3999, 2 (2000) and JP-A-10-303114. In the case of using an ArF excimer laser as the light source, in view of safety on handling as well as transmittance and refractive index at 193 nm, pure water (refractive index at 193 nm: 1.44) is considered to be a most promising immersion liquid. In the case of using an $F_2$ excimer laser as the light source, a fluorine-containing solution is being studied in the light of balance between transmittance and refractive index at 157 nm, but those satisfied in view of environmental safety or refractive index have been not yet found out. Considering the degree of immersion effect and the maturity of resist, the immersion exposure technique is expected to be most soon mounted on an ArF exposure machine.

Since the discovery of a resist for a KrF excimer laser (248 nm), an image forming method called chemical amplification is used as the image forming method for a resist so as to compensate the reduction in the sensitivity due to light absorption. The image forming method, for example, using positive chemical amplification is an image forming method where an acid generator in the exposed area decomposes upon exposure to generate an acid, the acid generated is used as a reaction catalyst in the baking after exposure (PEB: post exposure bake) to convert the alkali-insoluble group into an alkali-soluble group, and the exposed area is removed by an alkali developer.

A resist for an ArF excimer laser (wavelength: 193 nm) using this chemical amplification mechanism is predominating at present, but change in the resist profile due to time delay between exposure and PEB cannot be satisfactorily suppressed and improvement is demanded.

Also, it is pointed out that when the chemical amplification resist is applied to immersion exposure, the resist layer, comes, into contact with the immersion liquid at the exposure, as a result, the resist layer deteriorates or a component adversely affecting the immersion liquid bleeds out from the resist layer. International Publication No. WO 2004-068242, pamphlet describes a case where when the resist for ArF exposure is dipped in water before and after exposure, the resist performance is changed, and this is indicated as a problem in the immersion exposure.

Furthermore, in the immersion exposure process, when the exposure is performed by using a scanning-type immersion exposure machine, unless the immersion liquid moves following the movement of lens, the exposure speed decreases and this may affect the productivity. In the case where the immersion liquid is water, the resist film is preferably hydrophobic because of good followability of water.

SUMMARY OF THE INVENTION

An object of the present invention is to provide a positive resist composition ensuring that collapse of the resist pattern and deterioration of the profile due to time delay between exposure and PEB less occur not only at the normal exposure (dry exposure) but also at the immersion exposure and the followability for the immersion liquid at the immersion exposure is good; a resin used for the positive resist composition; a compound used for the synthesis of the resin; and a pattern forming method using the positive resist composition.

The present invention provides a positive resist composition having the following constructions, a resin used for the positive resist composition, a compound used for the synthesis of the resin, and a pattern forming method using the positive resist composition. The above-described object of the present invention can be attained by these composition, resin, compound and method.

(1) A positive resist composition, which comprises:

(A) a resin having a monocyclic or polycyclic alicyclic hydrocarbon structure of which solubility in an alkali developer increases under an action of an acid;

(B) a compound capable of generating an acid upon irradiation with actinic rays or radiation;

(C) a resin having at least one of a fluorine atom and a silicon atom; and (D) a solvent.

(2) The positive resist composition as described in (1) above, wherein the resin (C) is solid at 25° C.

(3) The positive resist composition as described in (1) or (2) above, wherein the resin (C) has a glass transition temperature of from 50 to 200° C.

(4) The positive resist composition as described in any of (1) to (3) above, wherein the resin (C) has a group represented by formula (F3a):

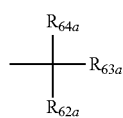

(F3a)

wherein $R_{62a}$ and $R_{63a}$ each independently represents an alkyl group with at least one hydrogen atom being substituted by a fluorine atom, and $R_{62a}$ and $R_{63a}$ may combine with each other to form a ring; and $R_{64a}$ represents a hydrogen atom, a fluorine atom or an alkyl group.

(5) The positive resist composition as described in any of (1) to (3) above, wherein the resin (C) has a group represented by any one of formulae (CS-1) to (CS-3):

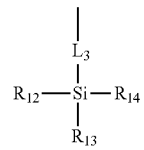

(CS-1)

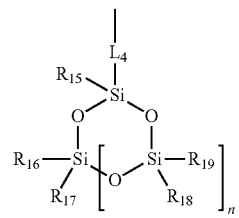

(CS-2)

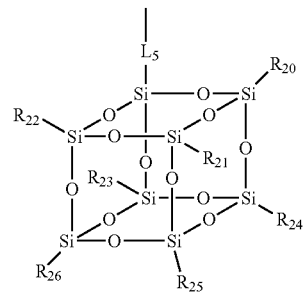

(CS-3)

wherein $R_{12}$ to $R_{26}$ each independently represents a linear or branched alkyl group or a cycloalkyl group; and $L_3$ to $L_5$ each independently represents a single bond or a divalent linking group.

(6) The positive resist composition as described in any of (1) to (3) above, wherein the resin (C) is a resin selected from following (C-1) to (C-6):

(C-1) a resin containing (a) a repeating unit having a fluoroalkyl group;

(C-2) a resin containing (b) a repeating unit having a trialkylsilyl group or a cyclic siloxane structure;

(C-3) a resin containing (a) a repeating unit having a fluoroalkyl group and (c) a repeating unit having a branched alkyl group, a cycloalkyl group, a branched alkenyl group, a cycloalkenyl group or an aryl group;

(C-4) a resin containing (b) a repeating unit having a trialkylsilyl group or a cyclic siloxane structure and (c) a repeating unit having a branched alkyl group, a cycloalkyl group, a branched alkenyl group, a cycloalkenyl group or an aryl group;

(C-5) a resin containing (a) a repeating unit having a fluoroalkyl group and (b) a repeating unit having a trialkylsilyl group or a cyclic siloxane structure; and (C-6) a resin containing (a) a repeating unit having a fluoroalkyl group, (b) a repeating unit having a trialkylsilyl group or a cyclic siloxane structure and (c) a repeating unit having a branched alkyl group, a cycloalkyl group, a branched alkenyl group, a cycloalkenyl group or an aryl group.

(7) The positive resist composition as described in any of (1) to (3) above,
wherein the resin (C) has a repeating unit represented by formula (Ia):

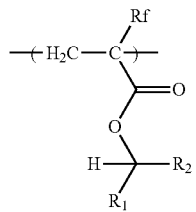
(Ia)

wherein Rf represents a fluorine atom or an alkyl group with at least one hydrogen atom being substituted by a fluorine atom;
$R_1$ represents an alkyl group; and
$R_2$ represents a hydrogen atom or an alkyl group.

(8) The positive resist composition as described in any of (1) to (3) above,
wherein the resin (C) has a repeating unit represented by formula (II) and a repeating unit represented by formula (III):

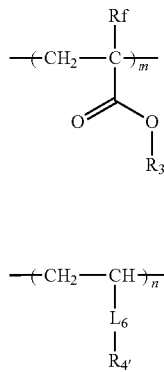
(II)

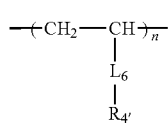
(III)

wherein Rf represents a fluorine atom or an alkyl group with at least one hydrogen atom being substituted by a fluorine atom;
$R_3$ represents an alkyl group, a cycloalkyl group, an alkenyl group or a cycloalkenyl group;
$R_4$ represents an alkyl group, a cycloalkyl group, an alkenyl group, a cycloalkenyl group, a trialkylsilyl group or a group having a cyclic siloxane structure;
$L_6$ represents a single bond or a divalent linking group;
$0<m<100$; and
$0<n<100$.

(9) A compound, which is represented by formula (I):

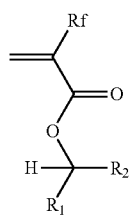
(I)

wherein Rf represents a fluorine atom or an alkyl group with at least one hydrogen atom being substituted by a fluorine atom;
$R_1$ represents an alkyl group; and
$R_2$ represents a hydrogen atom or an alkyl group.

(10) A resin, which has a repeating unit represented by formula (Ia):

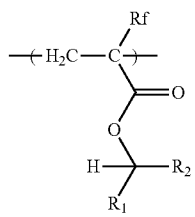
(Ia)

wherein Rf represents a fluorine atom or an alkyl group with at least one hydrogen atom being substituted by a fluorine atom;
$R_1$ represents an alkyl group; and
$R_2$ represents a hydrogen atom or an alkyl group.

(11) A resin, which has a repeating unit represented by formula (II) and a repeating unit represented by formula (III):

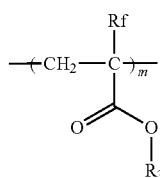
(II)

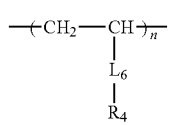
(III)

wherein Rf represents a fluorine atom or an alkyl group with at least one hydrogen atom being substituted by a fluorine atom;
$R_3$ represents an alkyl group, a cycloalkyl group, an alkenyl group or a cycloalkenyl group;
$R_4$ represents an alkyl group, a cycloalkyl group, an alkenyl group, a cycloalkenyl group, a trialkylsilyl group or a group having a cyclic siloxane structure;
$L_6$ represents a single bond or a divalent linking group;
$0<m<100$; and
$0<n<100$.

(12) A pattern forming method, which comprises:
forming a resist film from a positive resist composition as described in any of (1) to (8) above; and
exposing and developing the resist film.

Furthermore, preferred embodiments of the present invention are set forth below.

(13) The positive resist composition as described in any of (1) to (8) above,
wherein the resin (C) is stable to an acid and insoluble in an alkali developer.

(14) The positive resist composition as described in any of (1) to (8) above, wherein in the resin (C), the total amount of repeating units having an alkali-soluble group or a group of which solubility in a developer increases under the action of an acid or an alkali is 20 mol % or less based on all repeating units constituting the resin (C).

(15) The positive resist composition as described in any of (1) to (8), (13) and (14) above, wherein when formed into a film, a receding contact angle of water with the film is 70° or more.

(16) The positive resist composition as described in any of (1) to (8) and (13) to (15) above, wherein the resin (C) has a weight average molecular weight of from 1,000 to 50,000.

(17) The positive resist composition as described in any of (1) to (8) and (13) to (16) above, wherein an amount of the resin (C) added is from 0.1 to 5 mass % based on the entire solid content in the positive resist composition.

(18) The positive resist composition as described in any of (1) to (8) and (13) to (17) above, which further comprises (E) a basic compound.

(19) The positive resist composition as described in any of (1) to (8) and (13) to (18) above, which further comprises (F) a fluorine-containing and/or silicon-containing surfactant.

(20) The positive resist composition as described in any of (1) to (8) and (13) to (19) above, wherein the solvent (D) is a mixed solvent of two or more species including propylene glycol monomethyl ether acetate.

(21) The positive resist composition as described in any of (1) to (8) and (13) to (20) above, wherein the resin (A) contains a repeating unit having an alicyclic hydrocarbon group substituted by a hydroxyl group or a cyano group.

(22) The positive resist composition as described in any of (1) to (8) and (13) to (21) above, wherein the resin (A) is a copolymer containing at least a (meth)acrylate-based repeating unit having a lactone ring, a (meth)acrylate-based repeating unit having an organic group substituted by at least one a hydroxyl group and a cyano group and a (meth)acrylate-based repeating unit having an acid-decomposable group.

(23) The positive resist composition as described in any of (1) to (8) and (13) to (22) above, wherein the resin (A) has a weight average molecular weight of from 5,000 to 15,000 and a dispersity of from 1.2 to 3.0.

(24) The positive resist composition as described in any of (1) to (8) and (13) to (23) above, wherein the compound (B) is a compound capable of generating a fluorine atom-containing aliphatic sulfonic acid or a fluorine atom-containing benzenesulfonic acid upon irradiation with actinic rays or radiation.

(25) The positive resist composition as described in any of (1) to (8) and (13) to (24) above, wherein the compound (B) has a triphenylsulfonium structure.

(26) The positive resist composition as described in (25) above, wherein the compound (B) is a triphenylsulfonium salt compound having a fluorine-unsubstituted alkyl or cycloalkyl group in a cation moiety.

(27) The positive resist composition as described in any of (1) to (8) and (13) to (26) above, wherein the entire solid content concentration in the positive resist composition is from 1.0 to 6.0 mass %.

(28) The positive resist composition as described in any of (1) to (8) and (13) to (27) above, wherein the resin (A) does not have a fluorine atom and a silicon atom.

(29) The pattern forming method as described in (12) above, wherein the exposure is performed by exposure to light at a wavelength of 1 to 200 nm.

(30) The pattern forming method as described in (12) or (29) above, which further comprises an immersion exposure step.

BRIEF DESCRIPTION OF THE DRAWING

FIG. 1 is a schematic view showing the method for evaluating the followability of water.

DETAILED DESCRIPTION OF THE INVENTION

The present invention is described in detail below.

In the present invention, when a group (atomic group) is denoted without specifying whether substituted or unsubstituted, the group includes both a group having no substituent and a group having a substituent. For example, an "alkyl group" includes not only an alkyl group having no substituent (unsubstituted alkyl group) but also an alkyl group having a substituent (substituted alkyl group).

(A) Resin having a monocyclic, or polycyclic alicyclic hydrocarbon structure of which solubility in an alkali developer increases under the action of an acid The resin for use in the positive resist composition of the present invention is a resin which has a monocyclic or polycyclic alicyclic hydrocarbon structure and decomposes under the action of an acid to increase the solubility in an alkali developer, and this is a resin having a group capable of decomposing under the action of an acid to produce an alkali-soluble group (hereinafter sometimes referred to as an "acid-decomposable group") in the main or side chain or both the main and side chains of the resin (sometimes referred to as an "acid-decomposable resin", an "acid-decomposable resin (A)" or a "resin (A)").

Examples of the alkali-soluble group include groups having a phenolic hydroxyl group, a carboxylic acid group, a fluorinated alcohol group, a sulfonic acid group, a sulfonamide group, a sulfonylimide group, an (alkylsulfonyl) (alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl) methylene group, a bis(alkylsulfonyl)-imide group, a tris (alkylcarbonyl)methylene group or a tris(alkylsulfonyl)methylene group.

Among these alkali-soluble groups, preferred are a carboxylic acid group, a fluorinated alcohol group (preferably hexafluoroisopropanol) and a sulfonic acid group.

The group capable of decomposing under the action of an acid (acid-decomposable group) is preferably a group resulting from displacement of a hydrogen atom of these alkali-soluble groups by a group which splits off by the effect of an acid.

Examples of the group which splits off by the effect of an acid include —C($R_{36}$)($R_{37}$)($R_{38}$), —C($R_{36}$)($R_{37}$)(O$R_{39}$) and —C($R_{01}$)($R_{02}$)(O$R_{39}$).

In the formulae, $R_{36}$ to $R_{39}$ each independently represents an alkyl group, a cycloalkyl group, an aryl group, an aralkyl group or an alkenyl group, and $R_{36}$ and $R_{37}$ may combine with each other to form a ring.

$R_{01}$ and $R_{02}$ each independently represents a hydrogen atom, an alkyl group, a cycloalkyl group, an aryl group, an aralkyl group or an alkenyl group.

Preferred examples of the acid-decomposable group include a cumyl ester group, an enol ester group, an acetal ester group and a tertiary alkyl ester group, with a tertiary alkyl ester group being more preferred.

The positive resist composition of the present invention containing a resin having a monocyclic or polycyclic alicyclic hydrocarbon structure and being capable of decomposing under the action of an acid to increase the solubility in an alkali developer can be preferably used when irradiation of ArF excimer laser light is conducted.

The resin having a monocyclic or polycyclic alicyclic hydrocarbon structure and being capable of decomposing under the action of an acid to increase the solubility in an alkali developer (hereinafter sometimes referred to as an "alicyclic hydrocarbon-based acid-decomposable resin") is preferably a resin containing at least one repeating unit selected from the group consisting of a repeating unit having an alicyclic hydrocarbon-containing partial structure represented by any one of the following formulae (pI) to (pV), and a repeating unit represented by the following formula (II-AB):

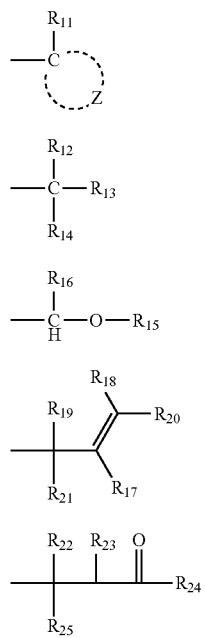

(pI)
(pII)
(pIII)
(pIV)
(pV)

In formulae (pI) to (pV), $R_{11}$ represents a methyl group, an ethyl group, an n-propyl group, an isopropyl group, an n-butyl group, an isobutyl group or a sec-butyl group. Z represents an atomic group necessary for forming a cycloalkyl group together with the carbon atom.

$R_{12}$ to $R_{16}$ each independently represents a linear or branched alkyl group having a carbon number of 1 to 4 or a cycloalkyl group, provided that at least one of $R_{12}$ to $R_{14}$ or either one of $R_{15}$ and $R_{16}$ represents a cycloalkyl group.

$R_{17}$ to $R_{21}$ each independently represents a hydrogen atom, a linear or branched alkyl group having a carbon number of 1 to 4 or a cycloalkyl group, provided that at least one of $R_{17}$ to $R_{21}$ represents a cycloalkyl group and that either one of $R_{19}$ and $R_{21}$ represents a linear or branched alkyl group having a carbon number of 1 to 4 or a cycloalkyl group.

$R_{22}$ to $R_{25}$ each independently represents a hydrogen atom, a linear or branched alkyl group having a carbon number of 1 to 4 or a cycloalkyl group, provided that at least one of $R_{22}$ to $R_{25}$ represents a cycloalkyl group. $R_{23}$ and $R_{24}$ may combine with each other to form a ring.

(II-AB)

In formula (II-AB), $R_{11}'$ and $R_{12}'$ each independently represents a hydrogen atom, a cyano group, a halogen atom or an alkyl group.

Z' represents an atomic group for forming an alicyclic structure, containing two bonded carbon atoms (C—C).

Formula (II-AB) is preferably the following formula (II-AB1) or (II-AB2):

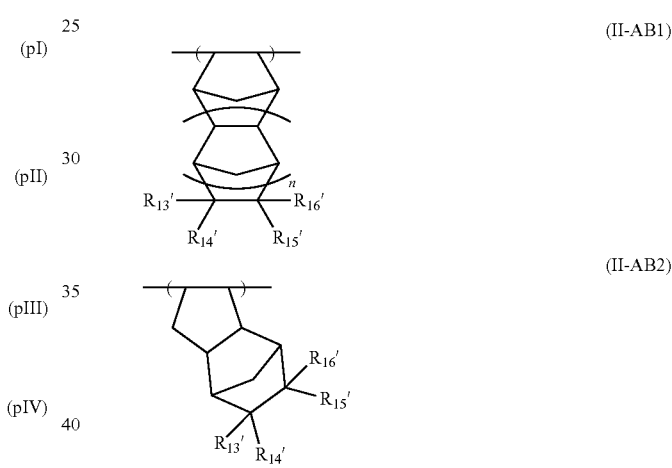

(II-AB1)
(II-AB2)

In formulae (II-AB1) and (II-AB2), $R_{13}'$ to $R_{16}'$ each independently represents a hydrogen atom, a halogen atom, a cyano group, —COOH, —COOR$_5$, a group capable of decomposing under the action of an acid, —C(=O)—X-A'-$R_{17}'$, an alkyl group or a cycloalkyl group, and at least two members out of $R_{13}'$ to $R_{16}'$ may combine to form a ring.

$R_5$ represents an alkyl group, a cycloalkyl group or a group having a lactone structure.

X represents an oxygen atom, a sulfur atom, —NH—, —NHSO$_2$— or —NHSO$_2$NH—.

A' represents a single bond or a divalent linking group.

$R_{17}'$ represents —COOH, —COOR$_5$, —CN, a hydroxyl group, an alkoxy group, —CO—NH—$R_6$, —CO—NH—SO$_2$—$R_6$ or a group having a lactone structure.

$R_6$ represents an alkyl group or a cycloalkyl group.

n represents 0 or 1.

In formulae (pI) to (pV), the alkyl group of $R_{12}$ to $R_{25}$ indicates a linear or branched alkyl group having a carbon number of 1 to 4.

The cycloalkyl group of $R_{11}$ to $R_{25}$ and the cycloalkyl group formed by Z together with the carbon atom may be monocyclic or polycyclic. Specific examples thereof include a group having a carbon number of 5 or more and having a monocyclo, bicyclo, tricyclo or tetracyclo structure. The carbon number thereof is preferably from 6 to 30, more preferably from 7 to 25. These cycloalkyl groups each may have a substituent.

Preferred examples of the cycloalkyl group include an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. Among these, more preferred are an adamantyl group, a norbornyl group, a cyclohexyl group, a cyclopentyl group, a tetracyclododecanyl group and a tricyclodecanyl group.

Examples of the substituent which these alkyl group and cycloalkyl group may further have include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). Examples of the substituent which these alkyl group, alkoxy group, alkoxycarbonyl group and the like may further have include a hydroxyl group, a halogen atom and an alkoxy group.

The structures represented by formulae (pI) to (pV) each can be used for the protection of an alkali-soluble group in the resin. Examples of the alkali-soluble group include various groups known in this technical field.

Specific examples thereof include a structure where the hydrogen atom of a carboxylic acid group, a sulfonic acid group, a phenol group or a thiol group is substituted by the structure represented by any one of formulae (pI) to (pV). Among these, preferred is a structure where the hydrogen atom of a carboxylic acid group or a sulfonic acid group is substituted by the structure represented by any one of formulae (pI) to (pV).

The repeating unit having an alkali-soluble group protected by the structure represented by any one of formulae (pI) to (pV) is preferably a repeating unit represented by the following formula (pA):

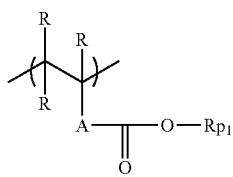

(pA)

In the formula, R represents a hydrogen atom, a halogen atom or a linear or branched alkyl group having a carbon number of 1 to 4, and a plurality of R's may be the same or different.

A represents a single bond, or a sole group or a combination of two or more groups, selected from the group consisting of an alkylene group, an ether group, a thioether group, a carbonyl group, an ester group, an amido group, a sulfonamido group, a urethane group and a urea group. A is preferably a single bond.

$Rp_1$ represents any one group of formulae (pI) to (pV).

The repeating unit represented by formula (pA) is preferably a repeating unit comprising a 2-alkyl-2-adamantyl (meth)acrylate or a dialkyl(1-adamantyl)methyl(meth)acrylate.

Specific examples of the repeating unit represented by formula (pA) are set forth below, but the present invention is not limited thereto.

(In the formulae, Rx represents H, $CH_3$ or $CH_2OH$, and Rxa and Rxa each represents an alkyl group having a carbon number of 1 to 4.)

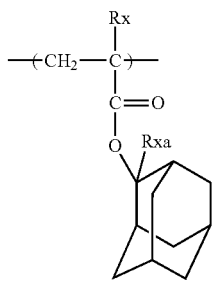

1

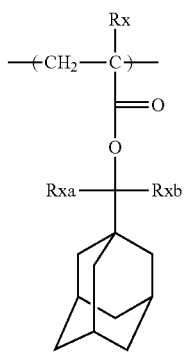

2

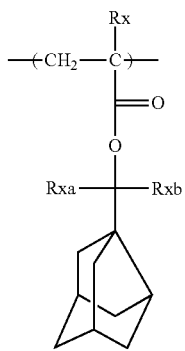

3

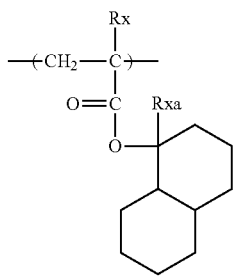

4

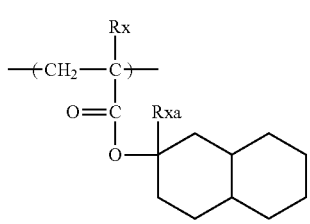

5

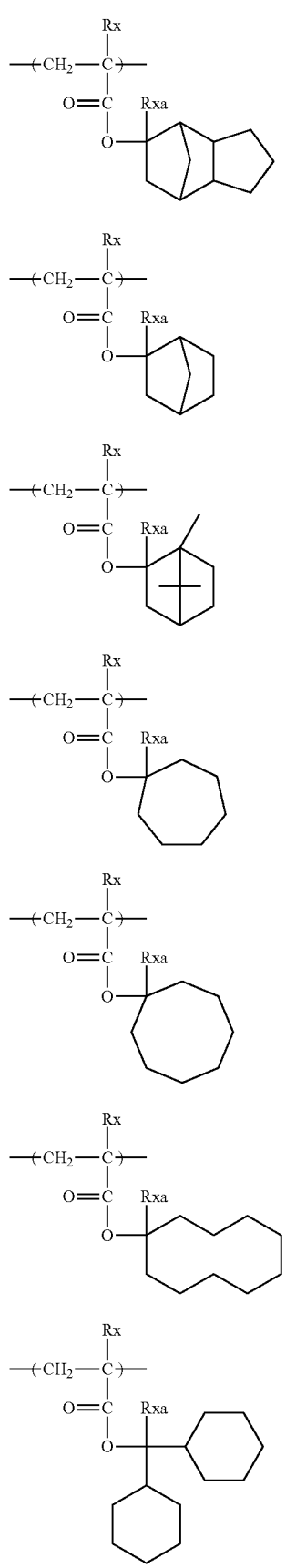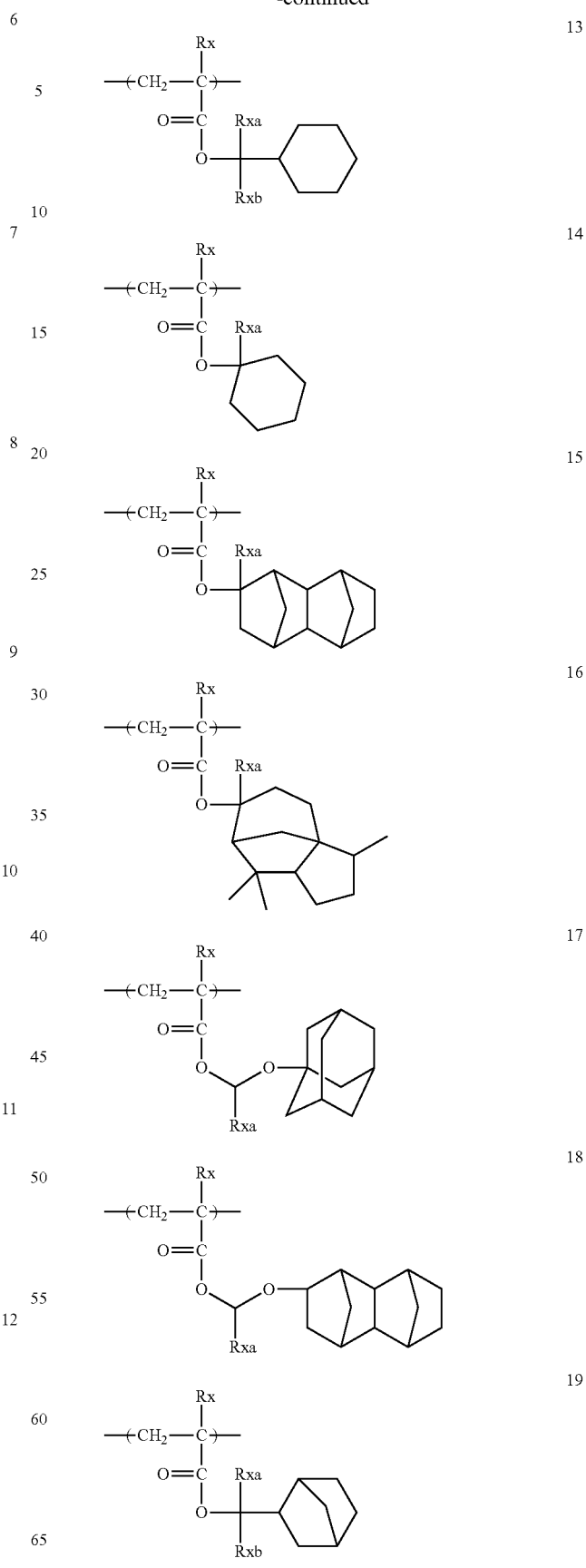

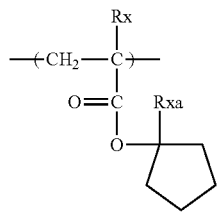

20

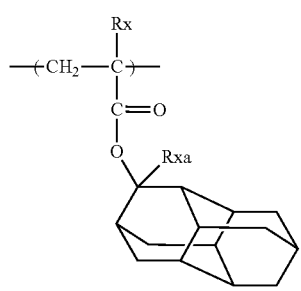

21

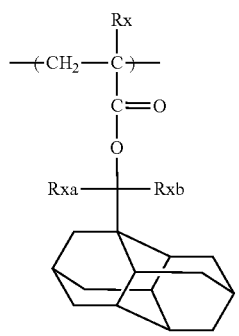

22

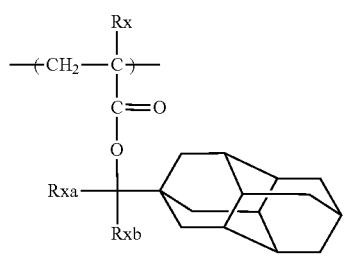

23

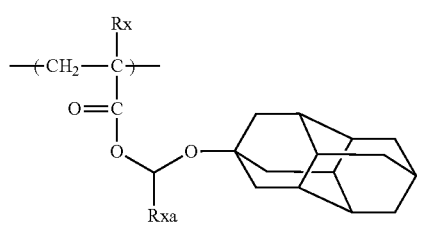

24

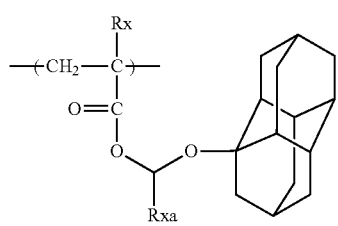

25

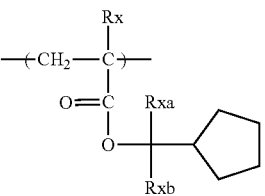

26

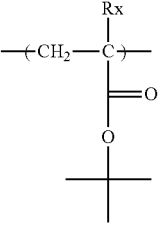

27

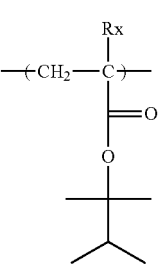

28

Examples of the halogen atom of $R_{11}'$ and $R_{12}'$ in formula (II-AB) include a chlorine atom, a bromine atom, a fluorine atom and an iodine atom.

The alkyl group of $R_{11}'$ and $R_{12}'$ includes a linear or branched alkyl group having a carbon number of 1 to 10.

The atomic group of Z' for forming an alicyclic structure is an atomic group for forming, in the resin, an alicyclic hydrocarbon repeating unit which may have a substituent. In particular, an atomic group for forming a crosslinked alicyclic structure to form a crosslinked alicyclic hydrocarbon repeating unit is preferred.

Examples of the skeleton of the alicyclic hydrocarbon formed are the same as those of the alicyclic hydrocarbon group of $R_{12}$ to $R_{25}$ in formulae (pI) to (pVI).

The alicyclic hydrocarbon skeleton may have a substituent, and examples of the substituent include $R_{13}'$ to $R_{16}'$ in formulae (II-AB1) and (II-AB2).

In the alicyclic hydrocarbon-based acid-decomposable resin for use in the present invention, the group capable of decomposing under the action of an acid may be contained in at least one repeating unit out of the repeating unit having an alicyclic hydrocarbon-containing partial structure represented by any one of formulae (pI) to (pV), the repeating unit represented by formula (II-AB), and the repeating unit comprising a copolymerization component described later.

Various substituents $R_{13}'$ to $R_{16}'$ in formulae (II-AB1) and (II-AB2) may work out to a substituent of an atomic group for forming an alicyclic structure in formula (II-AB) or an atomic group Z for forming a crosslinked alicyclic structure.

Specific examples of the repeating units represented by formulae (II-AB1) and (II-AB2) are set forth below, but the present invention is not limited thereto.

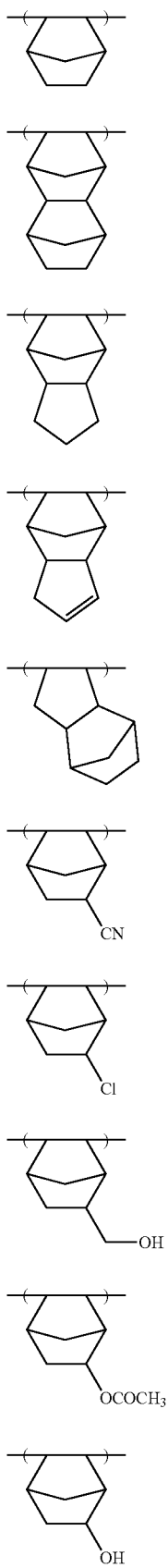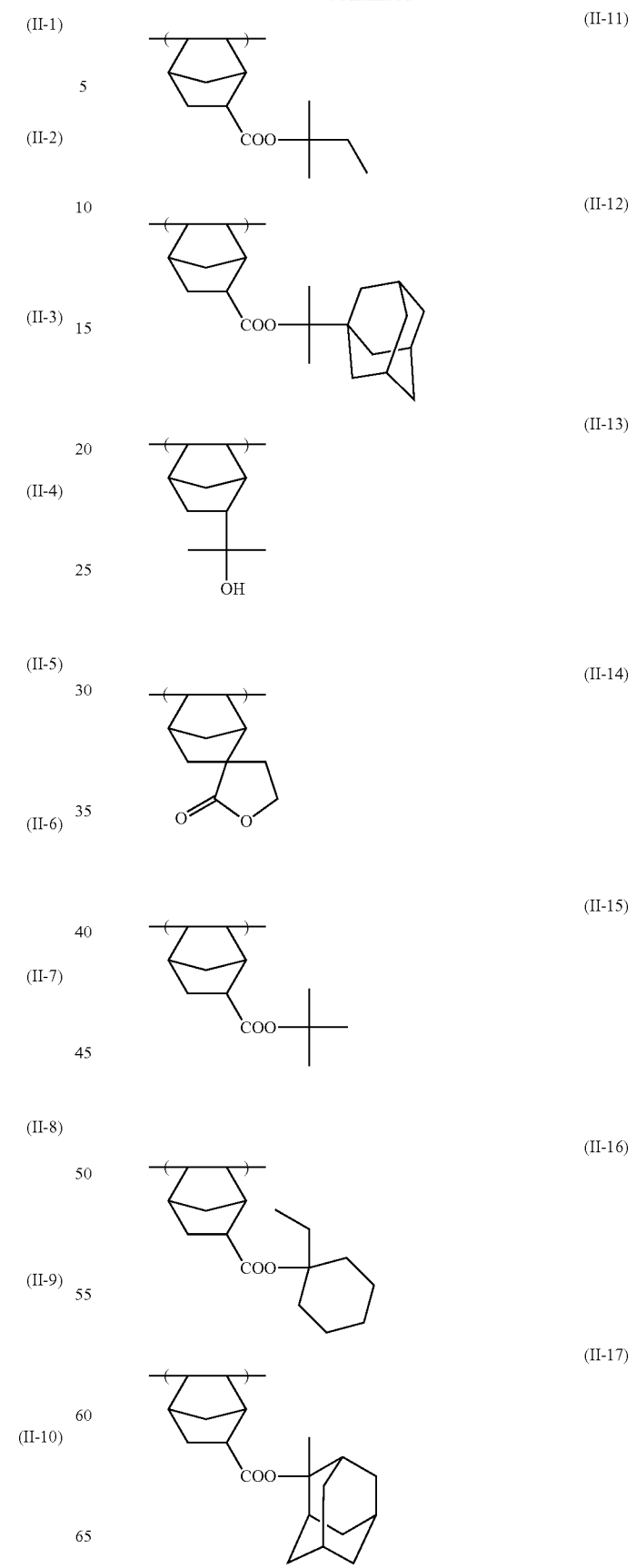

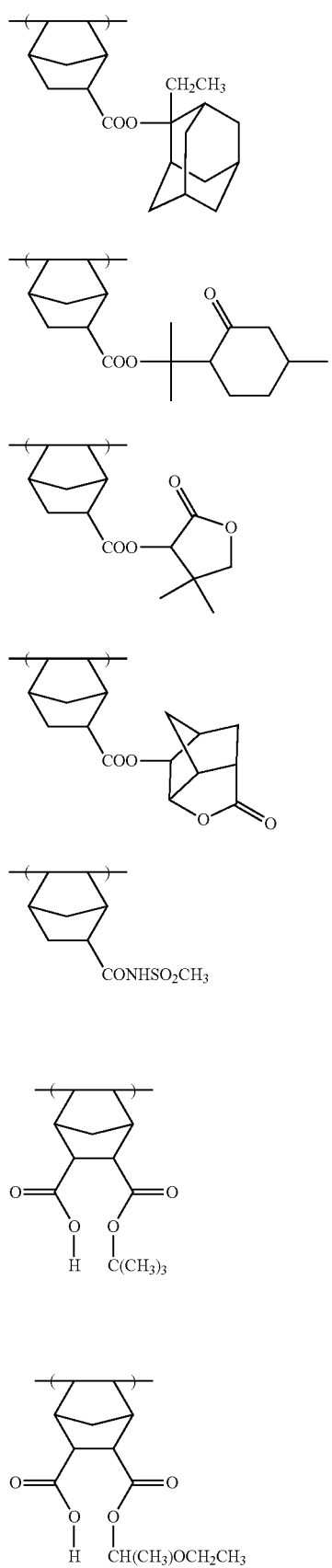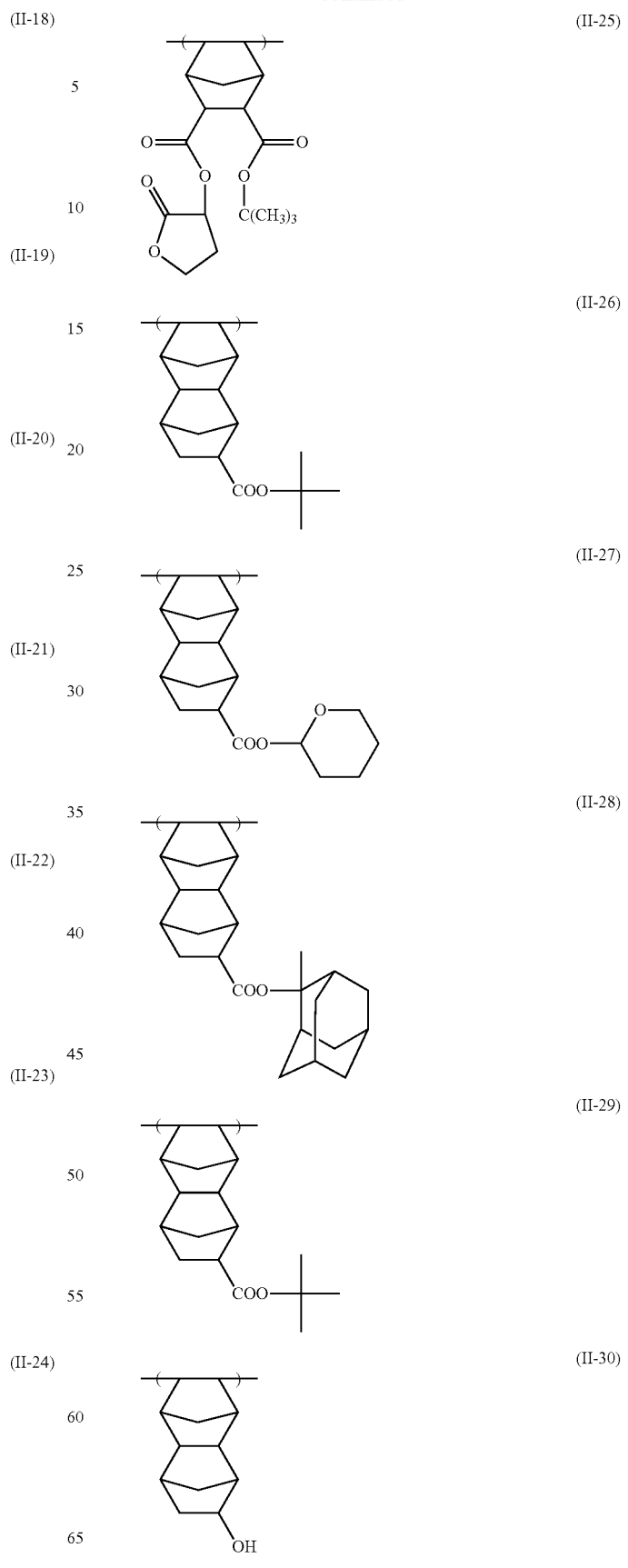

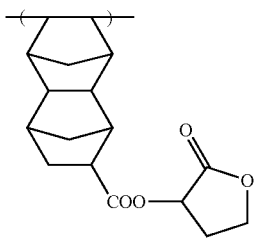
(II-31)

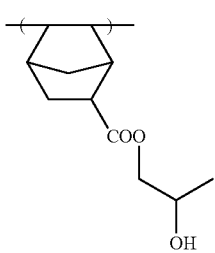
(II-32)

The alicyclic hydrocarbon-based acid-decomposable resin for use in the present invention preferably has a lactone group. As for the lactone group, any group may be used as long as it has a lactone structure, but a group having a 5- to 7-membered ring lactone structure is preferred. The 5- to 7-membered ring lactone structure is preferably condensed with another ring structure in the form of forming a bicyclo or spiro structure. It is more preferred to contain a repeating unit' having' a lactone structure-containing group represented by any one of the following formulae (LC1-1) to (LC1-16). The group having a lactone structure may be bonded directly to the main chain. Among these lactone structures, preferred are the groups represented by formulae (LC1-1), (LC1-4), (LC1-5), (LC1-6), (LC1-13) and (LC1-14). By virtue of using a specific lactone structure, the line edge roughness and the development defect are improved.

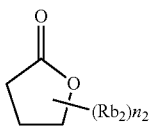
LC1-1

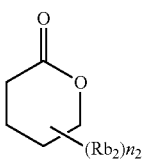
LC1-2

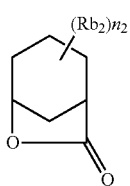
LC1-3

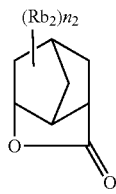
LC1-4

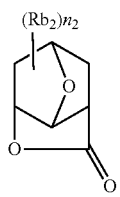
LC1-5

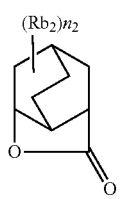
LC1-6

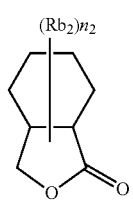
LC1-7

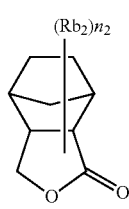
LC1-8

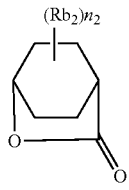
LC1-9

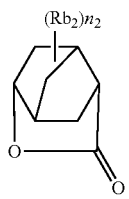
LC1-10

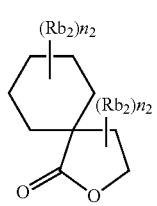
LC1-11

LC1-12
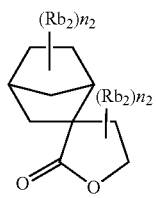

LC1-13
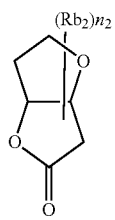

LC1-14
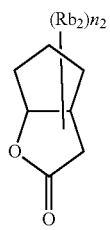

LC1-15
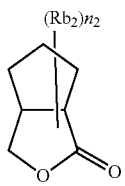

LC1-16
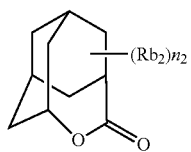

The lactone structure moiety may or may not have a substituent ($Rb_2$). Preferred examples of the substituent ($Rb_2$) include an alkyl group having a carbon number of 1 to 8, a cycloalkyl group having a carbon number of 4 to 7, an alkoxy group having a carbon number of 1 to 8, an alkoxycarbonyl group having a carbon number of 1 to 8, a carboxyl group, a halogen atom, a hydroxyl group, a cyano group and an acid-decomposable group. $n_2$ represents an integer of 0 to 4. When, $n_2$ is an integer of 2 or more, the plurality of $Rb_2$'s may be the same or different and also, the plurality of $Rb_2$'s may combine with each other to form a ring.

Examples of the repeating unit having a lactone structure-containing group represented by any one of formulae (LC1-1) to (LC1-16) include a repeating unit where at least one of $R_{13}'$ to $R_{16}'$ in formula (II-AB1) or (II-AB2) has a group represented by any one of formulae (LC1-1) to (LC1-16) (for example, $R_5$ of —$COOR_5$ is a group represented by any one of formulae (LC1-1) to (LC1-16)), and a repeating unit represented by the following formula (AI):

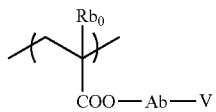
(AI)

In formula (AI), $Rb_0$ represents a hydrogen atom, a halogen atom or an alkyl group having a carbon number of 1 to 4.

Preferred examples of the substituent which the alkyl group of $Rb_0$ may have include a hydroxyl group and a halogen atom.

Examples of the halogen atom of $Rb_0$ include a fluorine atom, a chlorine atom, a bromine atom and an iodine atom.

$Rb_0$ is preferably a hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent group comprising a combination thereof, preferably a single bond or a linking group represented by -$Ab_1$-$CO_2$—. $Ab_1$ is a linear or branched alkylene group or a monocyclic or polycyclic cycloalkylene group, preferably a methylene group, an ethylene group, a cyclohexylene group, an adamantylene group or a norbornylene group.

V represents a group represented by any one of formulae (LC1-1) to (LC1-16).

The repeating unit having a lactone structure usually has an optical isomer, but any optical isomer may be used. One optical isomer may be used alone or a mixture of a plurality of optical isomers may be used. In the case of mainly using one optical isomer, the optical purity (ee) thereof is preferably 90 or more, more preferably 95 or more.

Specific examples of the repeating unit having a lactone structure-containing group are set forth below, but the present invention is not limited thereto.

(In the formulae, Rx is H, $CH_3$, $CH_2OH$ or $CF_3$.)

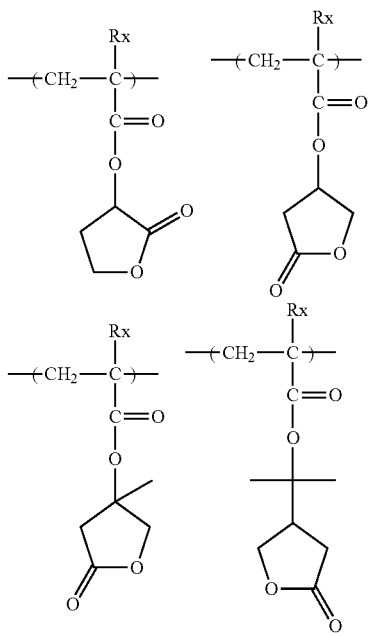

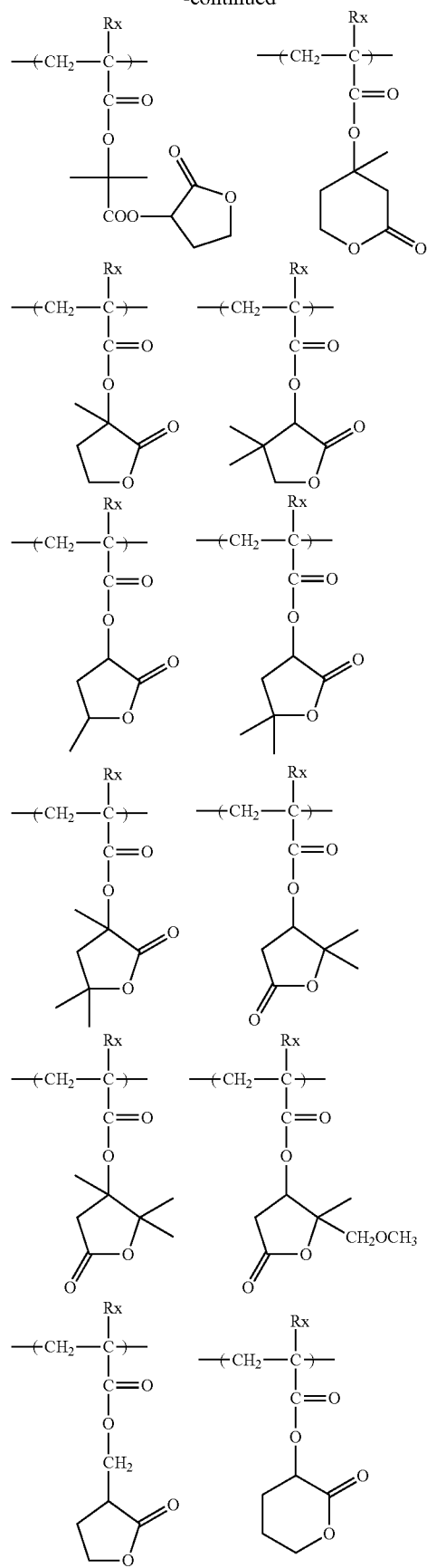
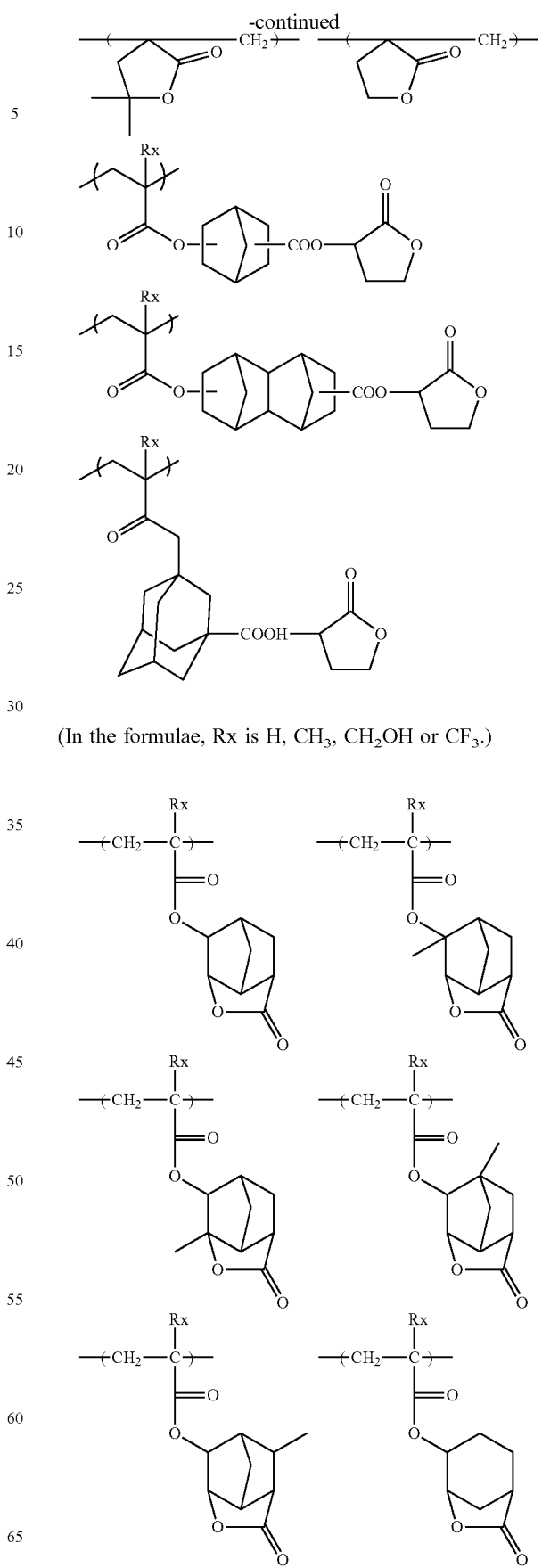
(In the formulae, Rx is H, CH₃, CH₂OH or CF₃.)

-continued
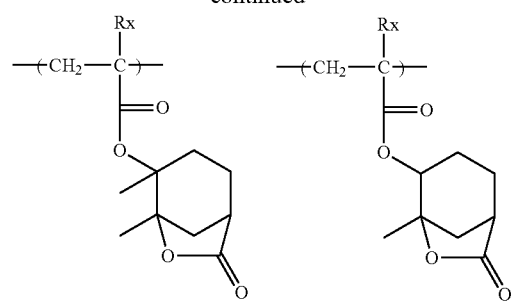
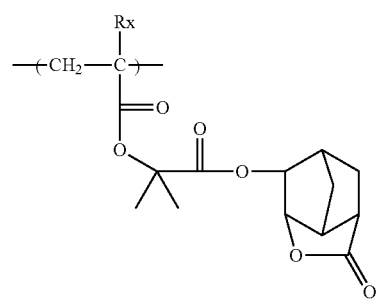
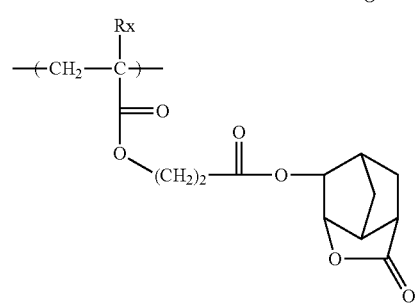
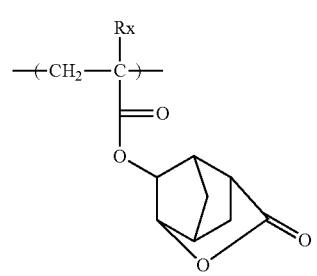
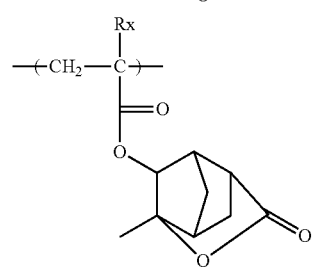
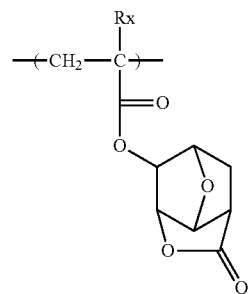
-continued
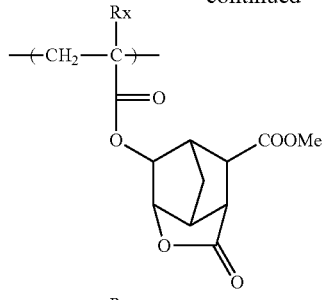
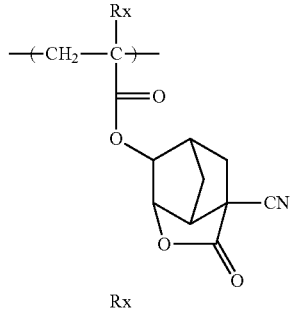
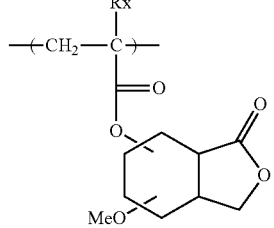
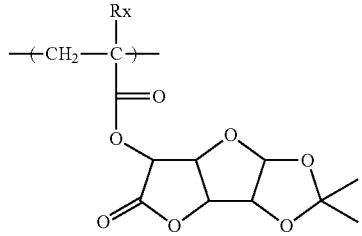
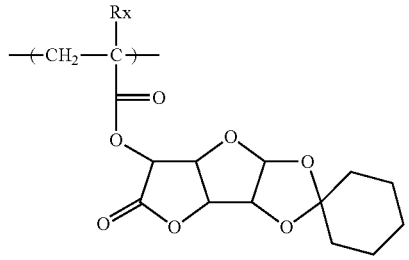
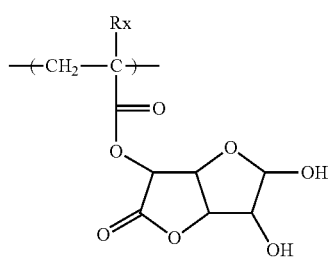

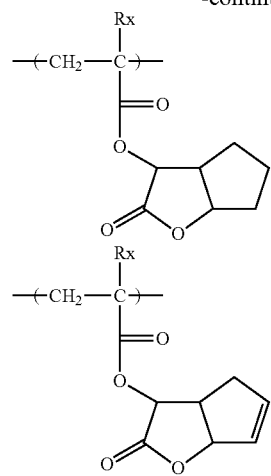
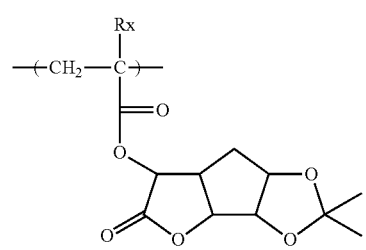
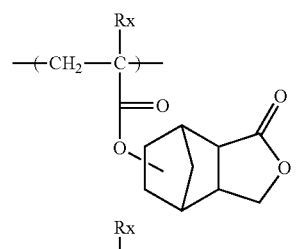
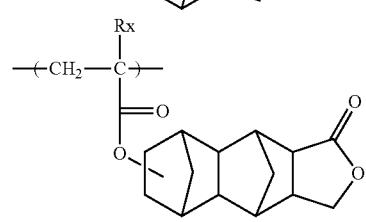
(In the formulae, Rx is H, CH₃, CH₂OH or CF₃.)
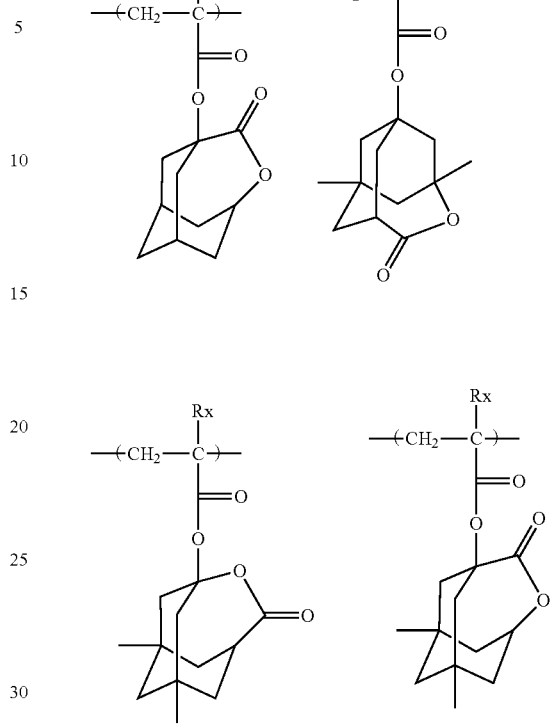
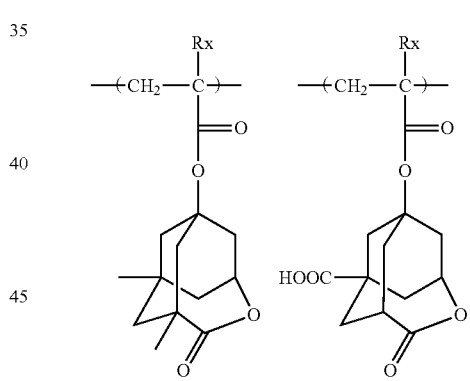
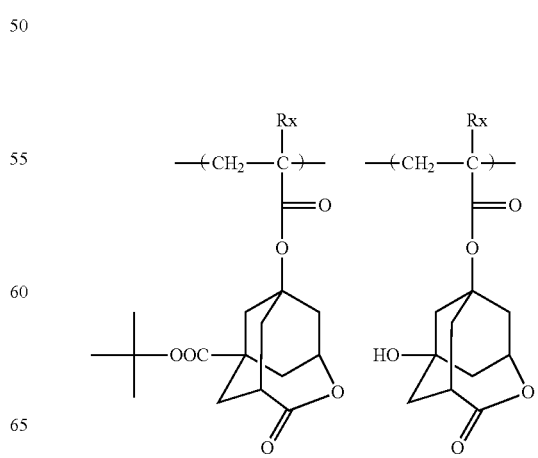

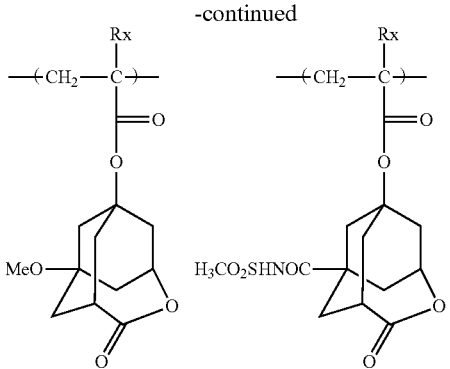

The alicyclic hydrocarbon-based acid-decomposable resin for use in the present invention preferably contains a repeating unit having a polar group-containing organic group, more preferably a repeating unit having an alicyclic hydrocarbon structure substituted by a polar group. By virtue of this repeating unit, the adhesion to substrate and the affinity for developer are enhanced. The alicyclic hydrocarbon structure of the alicyclic hydrocarbon structure substituted by a polar group is preferably an adamantyl group, a diamantyl group or a norbornane group. The polar group is preferably a hydroxyl group or a cyano group.

The alicyclic hydrocarbon structure substituted by a polar group is preferably a partial structure represented by any one of the following formulae (VIIa) to (VIId):

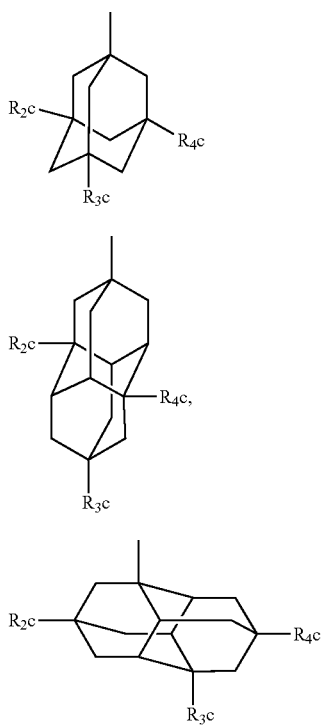

In formulae (VIIa) to (VIIc), $R_{2c}$ to $R_{4c}$ each independently represents a hydrogen atom, a hydroxyl group or a cyano group, provided that at least one of $R_{2c}$ to $R_{4c}$ represents a hydroxyl group or a cyano group. A structure where one or two member(s) out of $R_{2c}$ to $R_{4c}$ is(are) a hydroxyl group with the remaining being a hydrogen atom is preferred.

In formula (VIIa), it is more preferred that two members out of $R_{2c}$ to $R_{4c}$ are a hydroxyl group and the remaining is a hydrogen atom.

Examples of the repeating unit having a group represented by any one of formulae (VIIa) to (VIId) include a repeating unit where at least one of $R_{13}'$ to $R_{16}'$ in formula (II-AB1) or (II-AB2) has a group represented by formula (VII) (for example, $R_5$ of —COOR$_5$ is a group represented by any one of formulae (VIIa) to (VIId)), and repeating units represented by the following formulae (AIIa) to (AIId):

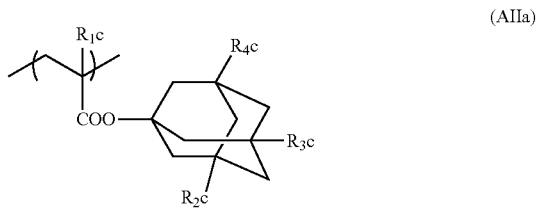

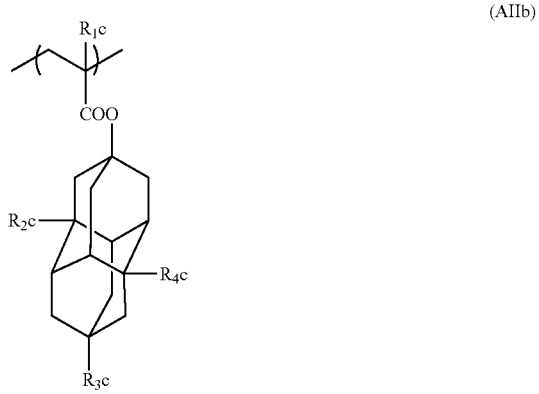

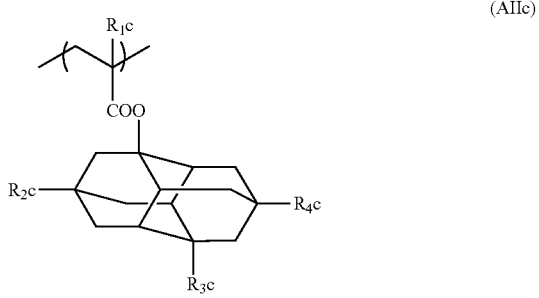

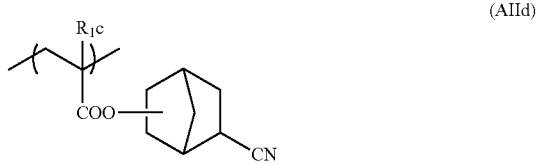

In formulae (AIIa) to (AIId), $R_{1c}$ represents a hydrogen atom, a methyl group, a trifluoromethyl group or a hydroxymethyl group.

$R_{2c}$ to $R_{4c}$ have the same meanings as $R_{2c}$ to $R_{4c}$ in formulae (VIIa) to (VIIc).

Specific examples of the repeating unit having a structure represented by any one of formulae (AIIa) to (AIId) are set forth below, but the present invention is not limited thereto.

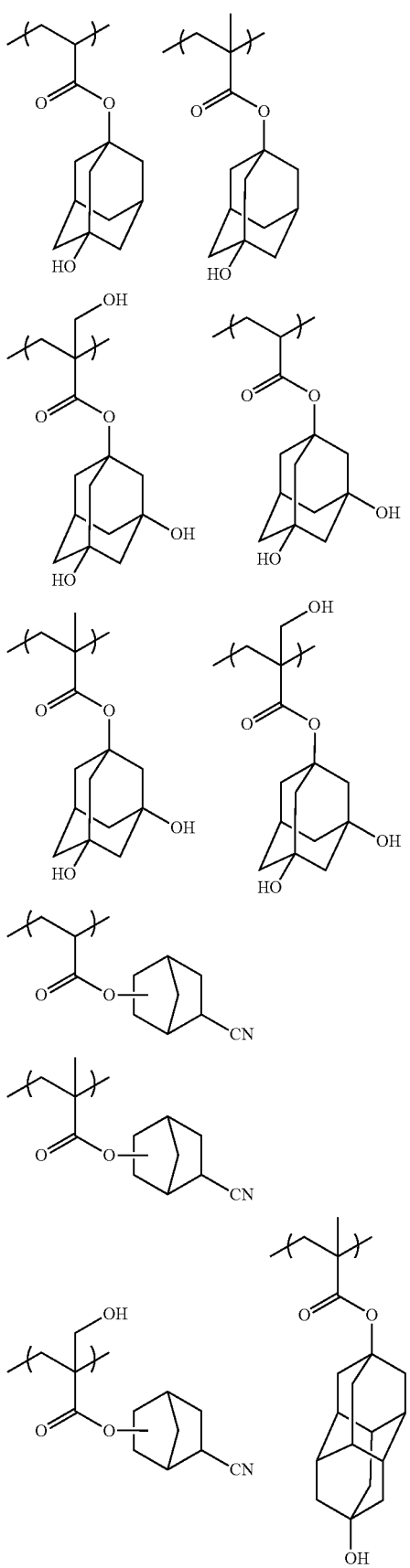

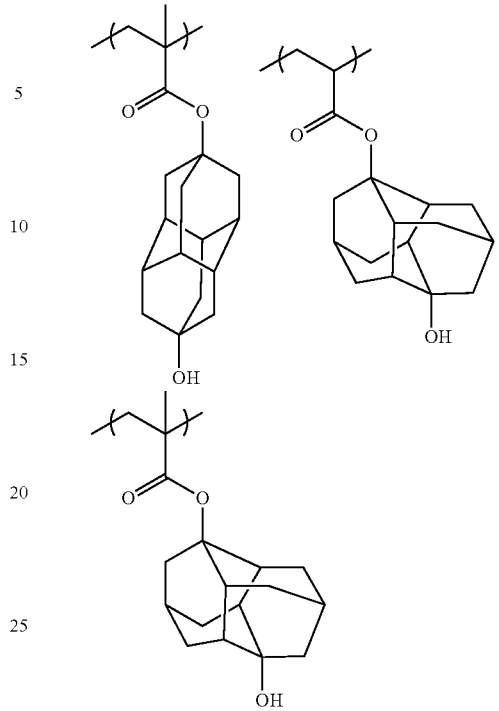

The alicyclic hydrocarbon-based acid-decomposable resin for use in the present invention may contain a repeating unit represented by the following formula (VIII):

(VIII)

In formula (VIII), $Z_2$ represents —O— or —N($R_{41}$)—. $R_{41}$ represents a hydrogen atom, a hydroxyl group, an alkyl group or —OSO$_2$—$R_{42}$. $R_{42}$ represents an alkyl group, a cycloalkyl group or a camphor residue. The alkyl group of $R_{41}$ and $R_{42}$ may be substituted by a halogen atom (preferably fluorine atom) or the like.

Specific examples of the repeating unit represented by formula (VIII) are set forth below, but the present invention is not limited thereto.

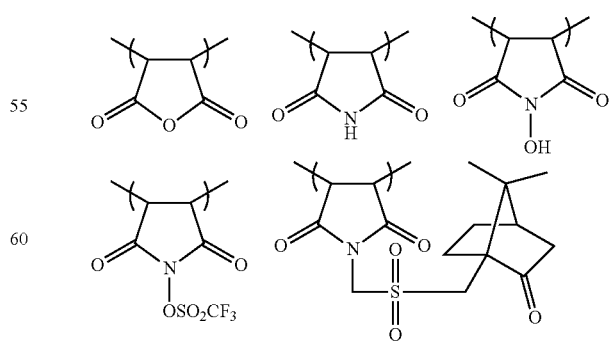

The alicyclic hydrocarbon-based acid-decomposable resin for use in the present invention preferably contains a repeating unit having an alkali-soluble group, more preferably a repeating unit having a carboxyl group. By virtue of containing such a repeating unit, the resolution increases in the usage of forming contact holes. As for the repeating unit having a carboxyl group, a repeating unit where a carboxyl group is directly bonded to the resin main chain, such as repeating unit by an acrylic acid or a methacrylic acid, a repeating unit where a carboxyl group is bonded to the resin main chain through a linking group, and a repeating unit where a carboxyl group is introduced into the terminal of the polymer chain by using a polymerization initiator or chain transfer agent having an alkali-soluble group at the polymerization, all are preferred. The linking group may have a monocyclic or polycyclic hydrocarbon structure. A repeating unit by an acrylic acid or a methacrylic acid is particularly preferred.

The alicyclic hydrocarbon-based acid-decomposable resin for use in the present invention may further contain a repeating unit having from 1 to 3 groups represented by formula (F1). By virtue of this repeating unit, the line edge roughness performance is enhanced.

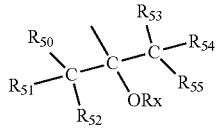
(F1)

In formula (F1), $R_{50}$ to $R_{55}$ each independently represents a hydrogen atom, a fluorine atom or an alkyl group, provided that at least one of $R_{50}$ to $R_{55}$ is a fluorine atom or an alkyl group with at least one hydrogen atom being substituted by a fluorine atom.

Rx represents a hydrogen atom or an organic group (preferably an acid-decomposable protective group, an alkyl group, a cycloalkyl group, an acyl group or an alkoxycarbonyl group).

The alkyl group of $R_{50}$ to $R_{55}$ may be substituted by a halogen atom (e.g., fluorine), a cyano group or the like, and the alkyl group is preferably an alkyl group having a carbon number of 1 to 3, such as methyl group and trifluoromethyl group.

It is preferred that $R_{50}$ to $R_{55}$ all are a fluorine atom.

The organic group represented by Rx is preferably an acid-decomposable protective group or an alkyl, cycloalkyl, acyl, alkylcarbonyl, alkoxycarbonyl, alkoxycarbonylmethyl, alkoxymethyl or 1-alkoxyethyl group which may have a substituent.

The repeating unit having a group represented by formula (F1) is preferably a repeating unit represented by the following formula (F2):

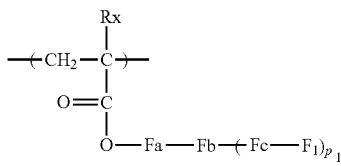
(F2)

In formula (F2), Rx represents a hydrogen atom, a halogen atom or an alkyl group having a carbon number of 1 to 4. Preferred examples of the substituent which the alkyl group of Rx may have include a hydroxyl group and a halogen atom.

Fa represents a single bond or a linear or branched alkylene group, preferably a single bond.

Fb represents a monocyclic or polycyclic hydrocarbon group.

Fc represents a single bond or a linear or branched alkylene group, preferably a single bond or a methylene group.

$F_1$ represents a group represented by formula (F1).

$p_1$ represents a number of 1 to 3.

The cyclic hydrocarbon group in Fb is preferably a cyclopentyl group, a cyclohexyl group or a norbornyl group.

Specific examples of the repeating unit having a structure of formula (F1) are set forth below, but the present invention is not limited thereto.

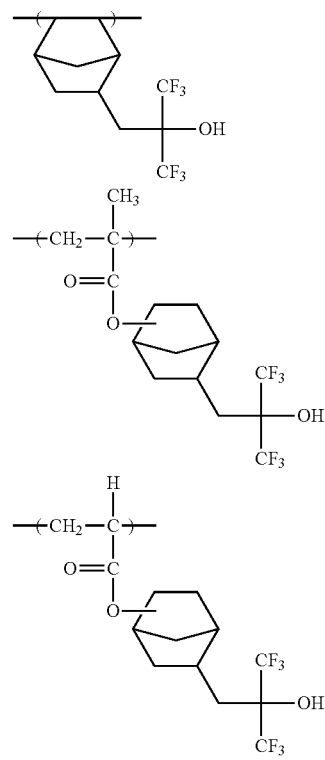

The alicyclic hydrocarbon-based acid-decomposable resin for use in the present invention may further contain a repeating unit having an alicyclic hydrocarbon structure and not exhibiting acid decomposability. By containing such a repeating unit, the dissolving out of low molecular components from the resist film to the immersion liquid at the immersion exposure can be reduced. Examples of this repeating unit include 1-adamantyl(meth)acrylate, tricyclodecanyl(meth)acrylate and cyclohexyl(meth)acrylate.

The alicyclic hydrocarbon-based acid-decomposable resin for use in the present invention may contain, in addition to the above-described repeating units, various repeating structural units for the purpose of controlling dry etching resistance, suitability for standard developer, adhesion to substrate, resist profile and properties generally required of the resist, such as resolving power, heat resistance and sensitivity.

Examples of such a repeating structural unit include, but are not limited to, repeating structural units corresponding to the monomers described below.

By virtue of such a repeating structural unit, the performance required of the alicyclic hydrocarbon-based acid-decomposable resin, particularly, (1) solubility in the coating solvent,
(2) film-forming property (glass transition point),
(3) alkali developability,
(4) film loss (selection of hydrophilic, hydrophobic or alkali-soluble group),
(5) adhesion of unexposed area to substrate,
(6) dry etching resistance and the like, can be subtly controlled.

Examples of the monomer include a compound having one addition-polymerizable unsaturated bond selected from acrylic acid esters, methacrylic acid esters, acrylamides, methacrylamides, allyl compounds, vinyl ethers and vinyl esters.

Other than these, an addition-polymerizable unsaturated compound copolymerizable with the monomers corresponding to the above-described various repeating structural units may be copolymerized.

In the alicyclic hydrocarbon-based acid-decomposable resin, the molar ratio of respective repeating structural units contained is appropriately determined to control the dry etching resistance of resist, suitability for standard developer, adhesion to substrate, resist profile and performances generally required of the resist, such as resolving power, heat resistance and sensitivity.

The preferred embodiment of the alicyclic hydrocarbon-based acid-decomposable resin for use in the present invention includes the followings:

(1) a resin containing a repeating unit having an alicyclic hydrocarbon-containing partial structure represented by any one of formulae (pI) to (pV) (side chain type), preferably containing a (meth)acrylate repeating unit having a structure represented by any one of formulae (pI) to (pV), and (2) a resin containing a repeating unit represented by formula (II-AB) (main chain type).

The embodiment of (2) further includes:

(3) a resin having a repeating unit represented by formula (II-AB), a maleic anhydride derivative and a (meth)acrylate structure (hybrid type).

In the alicyclic hydrocarbon-based acid-decomposable resin, the content of the repeating unit having an acid-decomposable group is preferably from 10 to 60 mol %, more preferably from 20 to 50 mol %, still more preferably from 25 to 40 mol %, based on all repeating structural units.

In the acid-decomposable resin, the content of the repeating unit having an acid-decomposable group is preferably from 10 to 60 mol %, more preferably from 20 to 50 mol %, still more preferably from 25 to 40 mol %, based on all repeating structural units.

In the alicyclic hydrocarbon-based acid-decomposable resin, the content of the repeating unit having an alicyclic hydrocarbon-containing partial structure represented by any one of formulae (pI) to (pV) is preferably from 20 to 70 mol %, more preferably from 20 to 50 mol %, still more preferably from 25 to 40 mol %, based on all repeating structural units.

In the alicyclic hydrocarbon-based acid-decomposable resin, the content of the repeating unit represented by formula (II-AB) is preferably from 10 to 60 mol %, more preferably from 15 to 55 mol %, still more preferably from 20 to 50 mol %, based on all repeating structural units.

In the acid-decomposable resin, the content of the repeating unit having a lactone ring is preferably from 10 to 70 mol %, more preferably from 20 to 60 mol %, still more preferably from 25 to 40 mol %, based on all repeating structural units.

In the acid-decomposable resin, the content of the repeating unit having a polar group-containing organic group is preferably from 1 to 40 mol %, more preferably from 5 to 30 mol %, still more preferably from 5 to 20 mol %, based on all repeating structural units.

The content of the repeating structural unit based on the monomer as the further copolymerization component in the resin can also be appropriately selected according to the desired resist performance but in general, the content thereof is preferably 99 mol % or less, more preferably 90 mol % or less, still more preferably 80 mol % or less, based on the total molar number of the repeating structural unit having an alicyclic hydrocarbon-containing partial structure represented by any one of formulae (pI) to (pV) and the repeating unit represented by formula (II-AB).

In the case of using the positive resist composition of the present invention for exposure with ArF, the resin preferably has no aromatic group in view of transparency to ArF light.

The alicyclic hydrocarbon-based acid-decomposable resin for use in the present invention is preferably a resin where all repeating units comprise a (meth)acrylate-based repeating unit. In this case, the repeating units may be all a methacrylate-based repeating unit, all an acrylate-based repeating unit, or a mixture of methacrylate-based repeating unit/acrylate-based repeating unit, but the content of the acrylate-based repeating unit is preferably 50 mol % or less based on all repeating units.

The alicyclic hydrocarbon-based acid-decomposable resin is preferably a copolymer having at least three kinds of repeating units, that is, a (meth)acrylate-based repeating unit, a (meth)acrylate-based repeating unit having an organic group substituted by either a hydroxyl group or a cyano group, and a (meth)acrylate-based repeating unit having an acid-decomposable group.

The alicyclic hydrocarbon-based acid-decomposable resin for use in the present invention is more preferably a ternary copolymerization polymer comprising from 20 to 50 mol % of the repeating unit having an alicyclic hydrocarbon-containing partial structure represented by any one of formulae (pI) to (pV), from 20 to 50 mol % of the repeating unit having a lactone structure and from 5 to 30% of the repeating unit having an alicyclic hydrocarbon structure substituted by a polar group, or a quaternary copolymerization polymer additionally comprising from 0 to 20% of other repeating units.

The resin is more preferably a ternary copolymerization polymer comprising from 20 to 50 mol % of the repeating unit having an acid-decomposable group represented by any one of the following formulae (ARA-1) to (ARA-5), from 20 to 50 mol % of the repeating unit having a lactone group represented by any one of the following formulae (ARL-1) to (ARL-6), and from 5 to 30 mol % of the repeating unit having an alicyclic hydrocarbon structure substituted by a polar group represented by any one of the following formulae (ARH-1) to (ARH-3), or a quaternary copolymerization polymer further comprising from 5 to 20 mol % of the repeating unit containing a carboxyl group or a structure represented by formula (F1), and the repeating unit having an alicyclic hydrocarbon structure and not exhibiting acid decomposability.

(In the formulae, Rxy$_1$ represents a hydrogen atom or a methyl group, and Rxa$_1$ and Rxb$_1$ each represents a methyl group or an ethyl group)
ARA-1
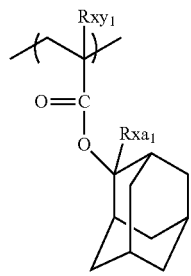
ARA-2
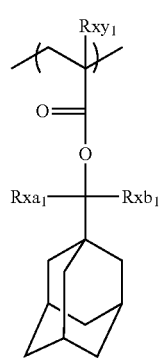
ARA-3
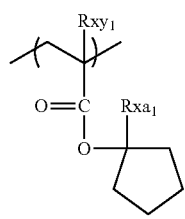
ARA-4
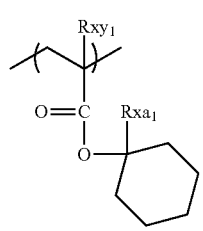
ARA-5
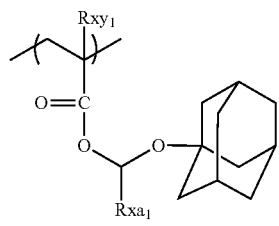
ARL-1
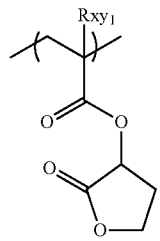
ARL-2
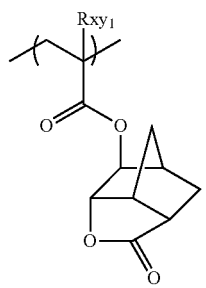
ARL-3
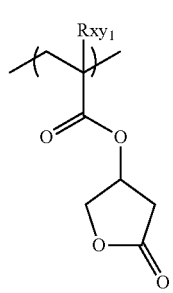
ARL-4
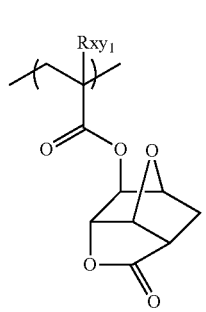
ARL-5
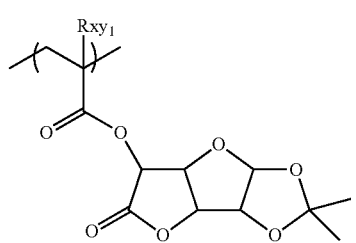
ARL-6
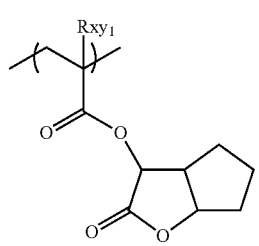

-continued

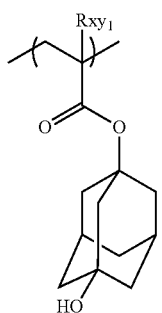

ARH-1

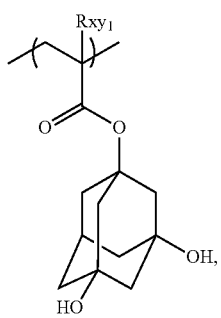

ARH-2

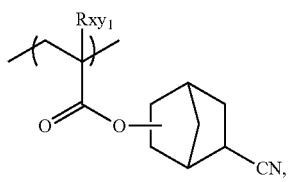

ARH-3

The alicyclic hydrocarbon-based acid-decomposable resin for use in the present invention can be synthesized by an ordinary method (for example, radical polymerization). Examples of the synthesis method in general include a batch polymerization method of dissolving the monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include tetrahydrofuran, 1,4-dioxane, ethers (e.g., diisopropyl ether), ketones (e.g., methyl ethyl ketone, methyl isobutyl ketone), an ester solvent (e.g., ethyl acetate), an amide solvent (e.g., dimethylformamide, diethylacetamide), and a solvent capable of dissolving the composition of the present invention, which is described later, such as propylene glycol monomethyl ether acetate, propylene glycol monomethyl ether and cyclohexanone. The polymerization is more preferably performed by using the same solvent as the solvent used in the resist composition of the present invention. By the use of this solvent, production of particles during storage can be suppressed.

The polymerization reaction is preferably performed in an inert gas atmosphere such as nitrogen and argon. As for the polymerization initiator, the polymerization is started by using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methyl-propionate). The initiator is added additionally or in parts, if desired. After the completion of reaction, the reactant is charged into a solvent, and the desired polymer is recovered by a method such as powder or solid recovery. The reaction concentration is from 5 to 50 mass %, preferably from 10 to 30 mass %, and the reaction temperature is usually from 10 to 150° C., preferably from 30 to 120° C., more preferably from 60 to 100° C. (In this specification, mass ratio is equal to weight ratio.)

The purification may be performed by the same method as that for the resin (C) described later, and a normal method, for example, a liquid-liquid extraction method of applying water washing or combining an appropriate solvent to remove residual monomers or oligomer components, a purification method in a solution sate, such as ultrafiltration of removing by extraction only polymers having a molecular weight lower than a specific molecular weight, a reprecipitation method of adding dropwise the resin solution in a bad solvent to solidify the resin in the bad solvent and thereby remove residual monomers or the like, or a purification method in a solid state, such as washing of the resin slurry with a bad solvent after separation by filtration, may be applied.

The weight average molecular weight of the resin for use in the present invention is preferably from 1,000 to 200,000, more preferably from 3,000 to 20,000, and most preferably from 5,000 to 15,000, in terms of polystyrene by the GPC method. When the weight average molecular weight is from 1,000 to 200,000, the heat resistance, dry etching resistance and developability can be prevented from deterioration and also, the deterioration in the film-forming property due to high viscosity can be prevented.

The dispersity (molecular weight distribution) is usually from 1 to 5, preferably from 1 to 3, more preferably from 1.2 to 3.0, still more preferably from 1.2 to 2.0. As the dispersity is smaller, the resolution and resist profile are more excellent, the side wall of the resist pattern is smoother, and the roughness property is more improved.

In the positive resist composition of the present invention, the amount of all resins for use in the present invention blended in the entire composition is preferably from 50 to 99.9 mass %, more preferably from 60 to 99.0 mass %, based on the entire solid content.

In the present invention, one resin may be used or a plurality of resins may be used in combination.

The alicyclic hydrocarbon-based acid-decomposable resin for use in the present invention preferably contains no fluorine or silicon atom in view of compatibility with the resin (C).

(B) Compound capable of generating an acid upon irradiation with actinic rays or radiation The positive resist composition of the present invention contains a compound capable of generating an acid upon irradiation with actinic rays or radiation (sometimes referred to as a "photoacid generator" or "component (B)").

The photoacid generator may be appropriately selected from a photoinitiator for photocationic polymerization, a photoinitiator for photoradical polymerization, a photo-decoloring agent for coloring matters, a photo-discoloring agent, a known compound used for microresist or the like and capable of generating an acid upon irradiation with actinic rays or radiation, and a mixture thereof.

Examples thereof include a diazonium salt, a phosphonium salt, a sulfonium salt, an iodonium salt, an imidosulfonate, an oxime sulfonate, a diazodisulfone, a disulfone and an o-nitrobenzyl sulfonate.

Also, a compound where such a group or compound capable of generating an acid upon irradiation with actinic rays or radiation is introduced into the main or side chain of the polymer, for example, compounds described in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029, may be used.

Furthermore, compounds capable of generating an acid by the effect of light described, for example, in U.S. Pat. No. 3,779,778 and European Patent 126,712 may also be used.

Among the compounds capable of generating an acid upon irradiation with actinic rays or radiation, preferred are the compounds represented by the following formulae (ZI), (ZII) and (ZIII):

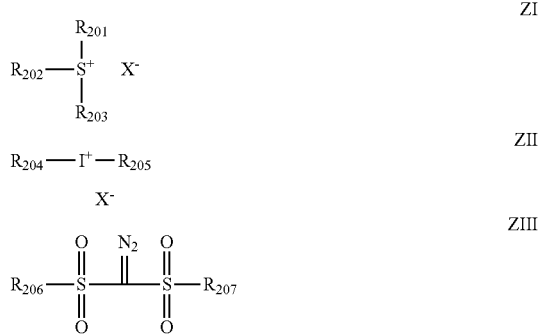

In formula (ZI), $R_{201}$, $R_{202}$ and $R_{203}$ each independently represents an organic group.

$X^-$ represents a non-nucleophilic anion, and preferred examples thereof include sulfonate anion, carboxylate anion, bis(alkylsulfonyl)amide anion, tris(alkylsulfonyl)methide anion, $BF_4^-$, $PF_6^-$ and $SbF_6^-$. The anion is preferably an organic anion containing a carbon atom.

The preferred organic anion includes the organic anions represented by the following formulae:

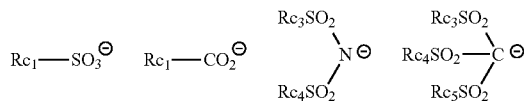

In the formulae, $Rc_1$ represents an organic group.

The organic group of $Rc_1$ includes an organic group having a carbon number of 1 to 30, and preferred examples thereof include an alkyl group which may be substituted, an aryl group, and a group where a plurality of these groups are connected through a single bond or a linking group such as —O—, —$CO_2$—, —S—, —$SO_3$— and —$SO_2N(Rd_1)$-. $Rd_1$ represents a hydrogen atom or an alkyl group.

$Rc_3$, $Rc_4$ and $Rc_5$ each independently represents an organic group. Preferred organic groups of $Rc_3$, $Rc_4$ and $Rc_5$ are the same as the preferred organic groups in $Rc_1$. The organic group is most preferably a perfluoroalkyl group having a carbon number of 1 to 4.

$Rc_3$ and $Rc_4$ may combine to form a ring. The group formed after $Rc_3$ and $Rc_4$ are combined includes an alkylene group and an arylene group, and a perfluoroalkylene group having a carbon number of 2 to 4 is preferred.

The organic group of $Rc_1$ and $Rc_3$ to $Rc_5$ is particularly preferably an alkyl group with the 1-position being substituted by a fluorine atom or a fluoroalkyl group, or a phenyl group substituted by a fluorine atom or a fluoroalkyl group. By virtue of having a fluorine atom or a fluoroalkyl group, the acidity of the acid generated upon irradiation with light increases and the sensitivity is enhanced. Also, when $Rc_3$ and $Rc_4$ are combined to form a ring, the acidity of the acid generated upon irradiation with light increases and the sensitivity is enhanced.

The carbon number of the organic group as $R_{203}$, $R_{202}$ and $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed after two members out of $R_{201}$ to $R_{203}$ are combined include an alkylene group (e.g., butylene, pentylene).

Specific examples of the organic group as $R_{201}$, $R_{202}$ and $R_{203}$ include corresponding groups in the compounds (ZI-1), (ZI-2) and (ZI-3) which are described later.

The compound may be a compound having a plurality of structures represented by formula (ZI). For example, the compound may be a compound having a structure that at least one of $R_{201}$ to $R_{203}$ in the compound represented by formula (ZI) is bonded to at least one of $R_{201}$ to $R_{203}$ in another compound represented by formula (ZI).

The component (ZI) is more preferably a compound (ZI-1), (ZI-2) or (ZI-3) described below.

The compound (ZI-1) is an arylsulfonium compound where at least one of $R_{201}$ to $R_{203}$ in formula (ZI) is an aryl group, that is, a compound having an arylsulfonium as the cation.

In the arylsulfonium compound, $R_{201}$ to $R_{203}$ all may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkyl-sulfonium compound and an aryldicycloalkylsulfonium compound.

The aryl group in the arylsulfonium compound is preferably an aryl group such as phenyl group and naphthyl group, or a heteroaryl group such as indole residue and pyrrole residue, more preferably a phenyl group or an indole residue. In the case where the arylsulfonium compound has two or more aryl groups, these two or more aryl groups may be the same of different.

The alkyl group which is present, if desired, in the arylsulfonium compound is preferably a linear or branched alkyl group having a carbon number of 1 to 15, and examples thereof include a methyl group, an ethyl group, a propyl group, an n-butyl group, a sec-butyl group and a tert-butyl group.

The cycloalkyl group which is present, if desired, in the arylsulfonium compound is preferably a cycloalkyl group having a carbon number of 3 to 15, and examples thereof include a cyclopropyl group, a cyclobutyl group and a cyclohexyl group.

The aryl group, alkyl group and cycloalkyl group of $R_{201}$ to $R_{203}$ each may have, as the substituent, an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 14), an alkoxy group (for example, an alkoxy group having a carbon number of 1 to 15), a halogen atom, a hydroxyl group or a phenylthio group. The substituent is preferably a linear or branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4 or an alkoxy group having a carbon number of 1 to 4. The substituent may be substituted to any one of three members $R_{201}$ to $R_{203}$ or may be substituted to all of these three members. In the case where $R_{201}$ to $R_{203}$ are an aryl group, the substituent is preferably substituted at the p-position of the aryl group.

The compound (ZI-2) is described below. The compound (ZI-2) is a compound where $R_{201}$ to $R_{203}$ in formula (ZI) each independently represents an aromatic ring-free organic group. The aromatic ring as used herein includes an aromatic ring containing a heteroatom.

The aromatic ring-free organic group as $R_{201}$ to $R_{203}$ generally has a carbon number of 1 to 30, preferably from 1 to 20.

$R_{201}$ to $R_{203}$ each is independently preferably an alkyl group, a cycloalkyl group, an allyl group or a vinyl group, more preferably a linear, branched or cyclic 2-oxoalkyl group or an alkoxycarbonylmethyl group, still more preferably a linear or branched 2-oxoalkyl group.

The alkyl group as $R_{201}$ to $R_{203}$ may be either linear or branched and preferably includes a linear or branched alkyl group having a carbon number of 1 to 10 (e.g., methyl, ethyl, propyl, butyl, pentyl). The alkyl group as $R_{201}$ to $R_{203}$ is preferably a linear or branched 2-oxoalkyl group or an alkoxycarbonylmethyl group.

The cycloalkyl group as $R_{201}$ to $R_{203}$ preferably includes a cycloalkyl group having a carbon number of 3 to 10 (e.g., cyclopentyl, cyclohexyl, norbornyl). The cycloalkyl group as $R_{201}$ to $R_{203}$ is preferably a cyclic 2-oxoalkyl group.

The linear, branched or cyclic 2-oxoalkyl group as $R_{201}$ to $R_{203}$ preferably includes a group having >C=O at the 2-position of the above-described alkyl or cycloalkyl group.

The alkoxy group in the alkoxycarbonylmethyl group as $R_{201}$ to $R_{203}$ preferably includes an alkoxy group having a carbon number of 1 to 5 (e.g., methoxy, ethoxy, propoxy, butoxy, pentoxy).

$R_{201}$ to $R_{203}$ each may be further substituted by a halogen atom, an alkoxy group (for example, an alkoxy group having a carbon number of 1 to 5), a hydroxyl group, a cyano group or a nitro group.

The compound (ZI-3) is a compound represented by the following formula (ZI-3), and this is a compound having a phenacylsulfonium salt structure.

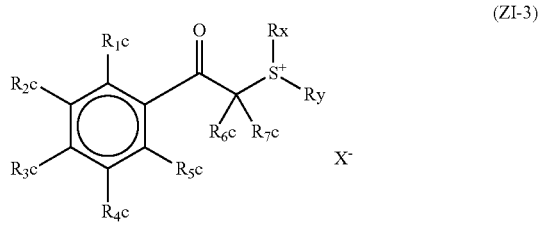

(ZI-3)

In formula (ZI-3), $R_{1c}$ to $R_{5c}$ each independently represents a hydrogen atom, an alkyl group, a cycloalkyl group, an alkoxy group or a halogen atom.

$R_{6c}$ and $R_{7c}$ each independently represents a hydrogen atom, an alkyl group or a cycloalkyl group.

$R_x$ and $R_y$ each independently represents an alkyl group, a cycloalkyl group, an allyl group or a vinyl group.

Any two or more members out of $R_{1c}$ to $R_{7c}$ or a pair of $R_x$ and $R_y$ may combine with each other to form a ring structure, and the ring structure may contain an oxygen atom, a sulfur atom, an ester bond or an amide bond. Examples of the group formed after any two or more members out of $R_{1c}$ to $R_{7c}$ or a pair of $R_x$ and $R_y$ are combined include a butylene group and a pentylene group.

$X^-$ represents a non-nucleophilic anion, and examples thereof are the same as those of the non-nucleophilic anion of $X^-$ in formula (ZI).

The alkyl group as $R_{1c}$ to $R_{7c}$ may be linear or branched and includes, for example, a linear or branched alkyl group having a carbon number of 1 to 20, preferably a linear or branched alkyl group having a carbon number of 1 to 12 (for example, a methyl group, an ethyl group, a linear or branched propyl group, a linear or branched butyl group, and a linear or branched pentyl group).

The cycloalkyl group as $R_{1c}$ to $R_{7c}$ preferably includes a cycloalkyl group having a carbon number of 3 to 8 (e.g., cyclopentyl, cyclohexyl).

The alkoxy group as $R_{1c}$ to $R_{5c}$ may be linear, branched or cyclic and includes, for example, an alkoxy group having a carbon number of 1 to 10, preferably a linear or branched alkoxy group having a carbon number of 1 to 5 (for example, a methoxy group, an ethoxy group, a linear or branched propoxy group, a linear or branched butoxy group, or a linear or branched pentoxy group) or a cyclic alkoxy group having a carbon number of 3 to 8 (e.g., cyclopentyloxy, cyclohexyloxy).

A compound where any one of $R_{1c}$ to $R_{5c}$ is a linear or branched alkyl group, a cycloalkyl group or a linear, branched or cyclic alkoxy group is preferred, and a compound where the sum of carbon numbers of $R_{1c}$ to $R_{5c}$ is from 2 to 15 is more preferred. By virtue of this construction, the solubility in a solvent is more enhanced and generation of particles during storage is suppressed.

Examples of the alkyl group as $R_x$ and $R_y$ are the same as those of the alkyl group as $R_{1c}$ to $R_{7c}$. The alkyl group as $R_x$ and $R_y$ is preferably a linear or branched 2-oxoalkyl group or an alkoxycarbonylmethyl group.

Examples of the cycloalkyl group as $R_x$ and $R_y$ are the same as those of the cycloalkyl group as $R_{1c}$ to $R_{7c}$. The cycloalkyl group as $R_x$ to $R_y$ is preferably a cyclic 2-oxoalkyl group.

Examples of the linear, branched or cyclic 2-oxoalkyl group include a group having >C=O at the 2-position of the alkyl group or cycloalkyl group as $R_{1c}$ to $R_{7c}$.

Examples of the alkoxy group in the alkoxycarbonylmethyl group are the same as those of the alkoxy group as $R_{1c}$ to $R_{5c}$.

$R_x$ and $R_y$ each is preferably an alkyl group having a carbon number of 4 or more, more preferably 6 or more, still more preferably 8 or more.

In formulae (ZII) and (ZIII), $R_{204}$ to $R_{207}$ each independently represents an aryl group, an alkyl group or a cycloalkyl group.

The aryl group of $R_{204}$ to $R_{207}$ is preferably a phenyl group or a naphthyl group, more preferably a phenyl group.

The alkyl group of $R_{204}$ to $R_{207}$ may be linear or branched and preferably includes a linear or branched alkyl group having a carbon number of 1 to 10 (e.g., methyl, ethyl, propyl, butyl, pentyl).

The cycloalkyl group of $R_{204}$ to $R_{207}$ is preferably a cycloalkyl group having a carbon number of 3 to 10 (e.g., cyclopentyl, cyclohexyl, norbornyl).

$R_{204}$ to $R_{207}$ each may have a substituent. Examples of the substituent which $R_{204}$ to $R_{207}$ each may have include an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 15), an alkoxy group (for example, an alkoxy group having a carbon number of 1 to 15), a halogen atom, a hydroxyl group and a phenylthio group.

$X^-$ represents a non-nucleophilic anion, and examples thereof are the same as those of the non-nucleophilic anion of $X^-$ in formula (ZI).

Other examples of the compound capable of generating an acid upon irradiation with actinic rays or radiation include the compounds represented by the following formulae (ZIV), (ZV) and (ZVI):

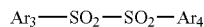
ZIV

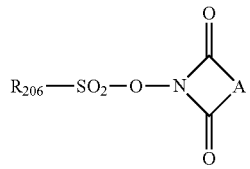
ZV

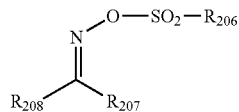
ZVI

In formulae (ZIV) to (ZVI), $Ar_3$ and $Ar_4$ each independently represents an aryl group.

$R_{206}$ represents an alkyl group or an aryl group.

$R_{207}$ and $R_{208}$ each independently represents an alkyl group, an aryl group or an electron-withdrawing group. $R_{207}$ is preferably an aryl group.

$R_{208}$ is preferably an electron-withdrawing group, more preferably a cyano group or a fluoroalkyl group.

A represents an alkylene group, an alkenylene group or an arylene group.

Among the compounds capable of generating an acid upon irradiation with actinic rays or radiation, the compounds represented by formulae (ZI) to (ZIII) are preferred.

The compound (B) is preferably a compound capable of generating a fluorine atom-containing aliphatic sulfonic acid or a fluorine atom-containing benzenesulfonic acid upon irradiation with actinic rays or radiation.

The compound (B) preferably has a triphenylsulfonium structure.

The compound (B) is preferably a triphenylsulfonium salt compound having a fluorine-unsubstituted alkyl or cycloalkyl group in the cation moiety.

Particularly preferred examples out of the compounds capable of generating an acid upon irradiation with actinic rays or radiation are set forth below.

-continued
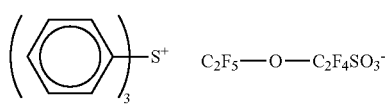 (z11)
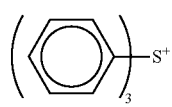 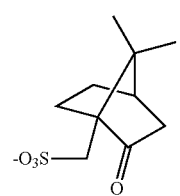 (z12)
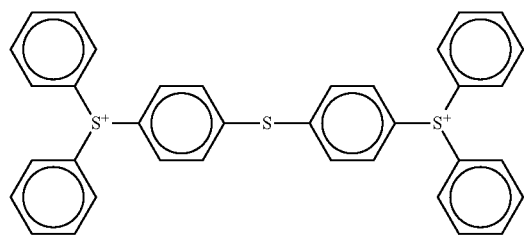
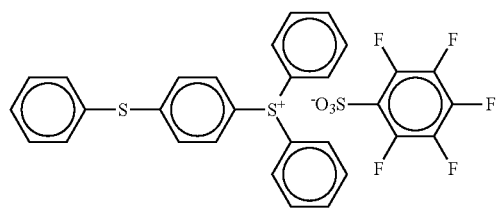 (z13)
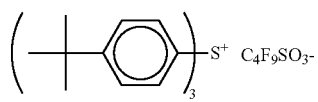 (z14)
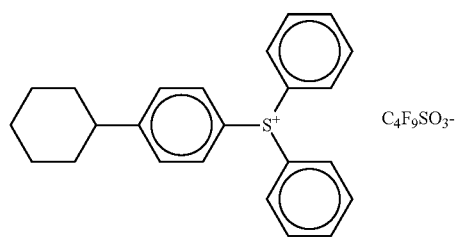 (z15)
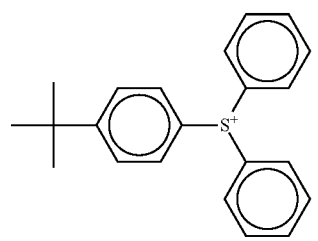 (z16)
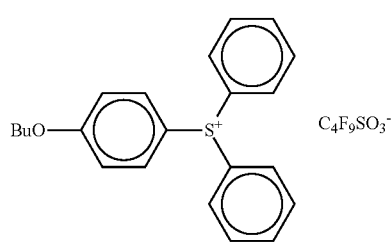 (z17)
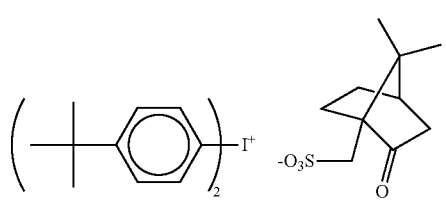 (z18)
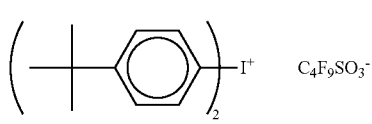 (z19)
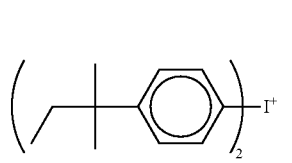 (z20)
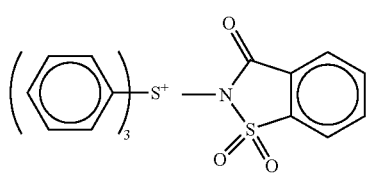 (z21)
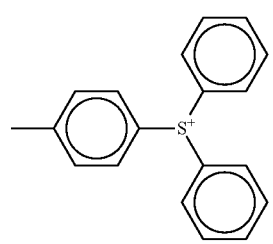 (z22)

-continued
(z24) 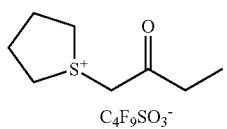
(z25) 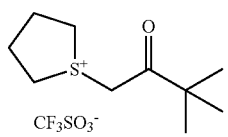
(z26) 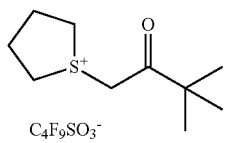
(z27) 
(z28) 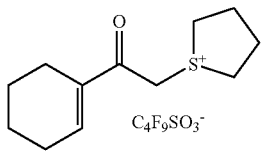
(z29) 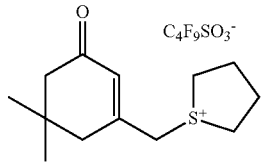
(z30) 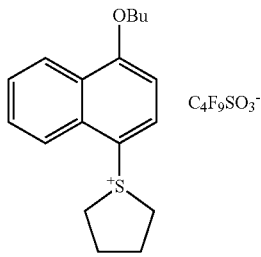
(z31) 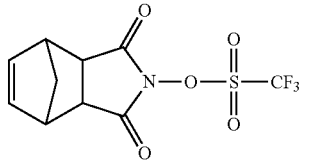
(z32) 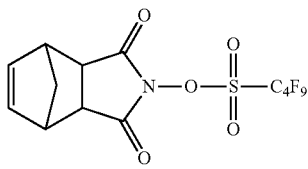
(z33) 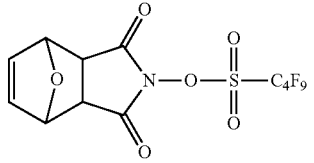
(z34) 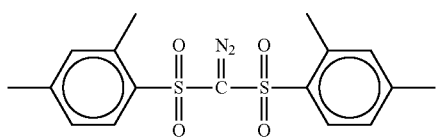
(z35) 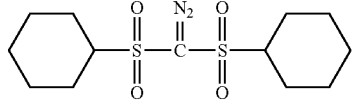
(z36) 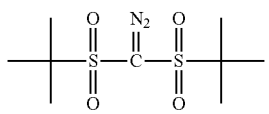
(z37) 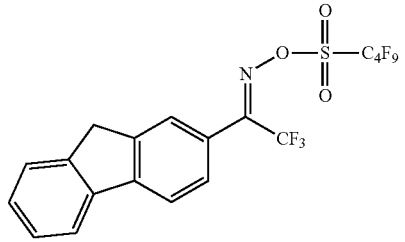
(z38) 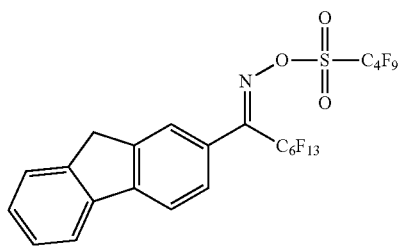
(z39) 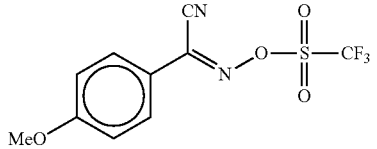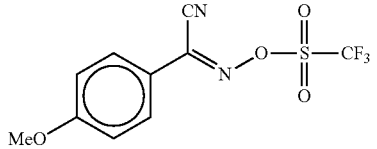

-continued
(z40)
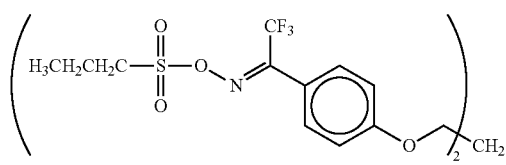
(z41)
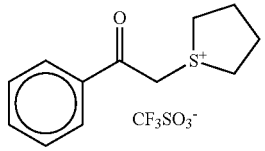
(z42)
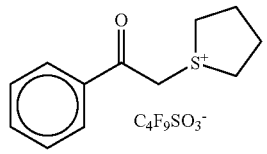
(z43)
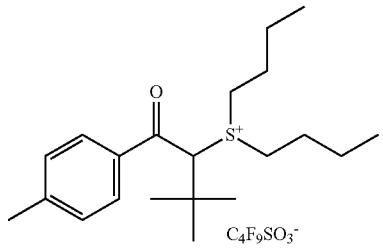
(z44)
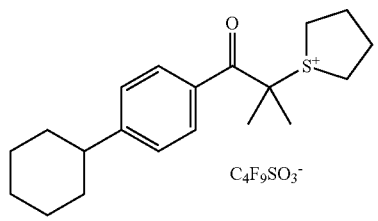
(z45)
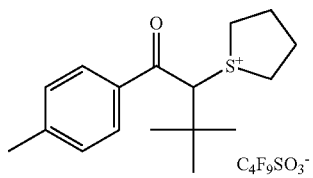
(z46)
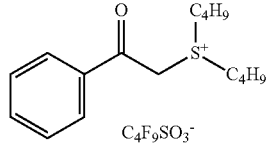
(z47)
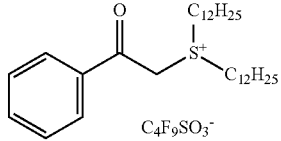
(z48)
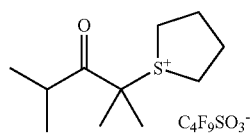
(z49)
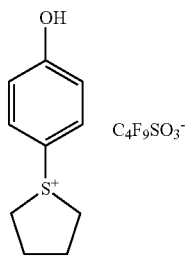
(z50)
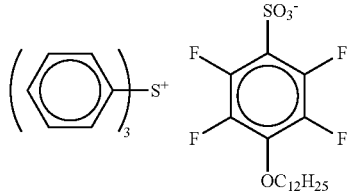
(z51)
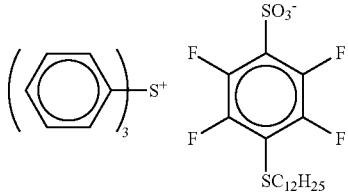
(z52)
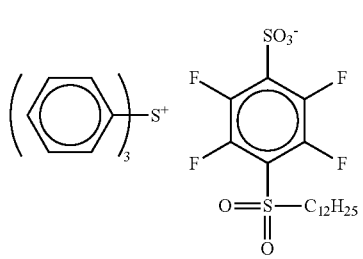
(z53)
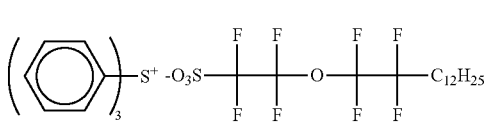

-continued
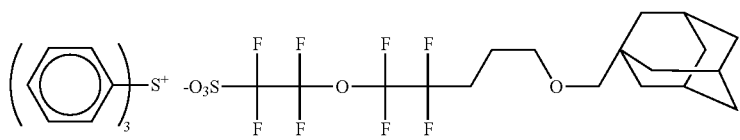
(z54)
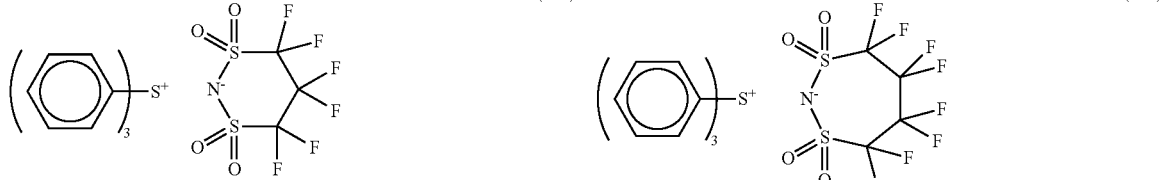
(z55) (z56)
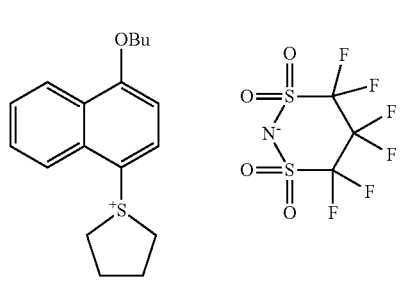
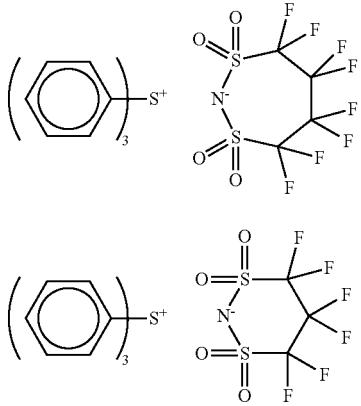
(z57) (z58)
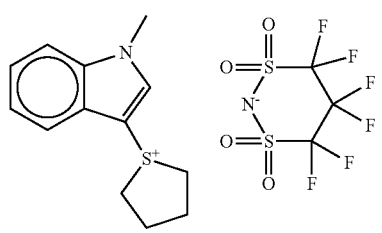
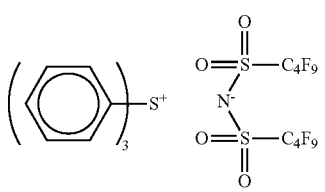
(z59) (z60)
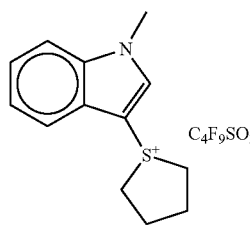
(z61)
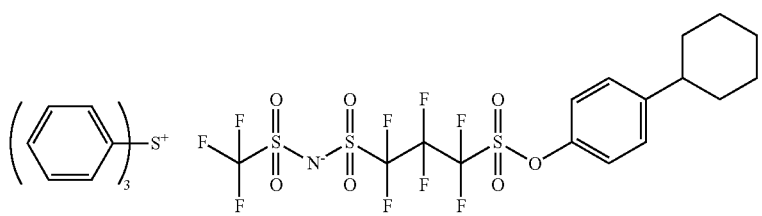
(z62)
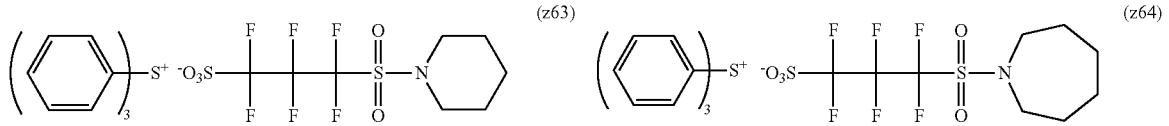
(z63) (z64)
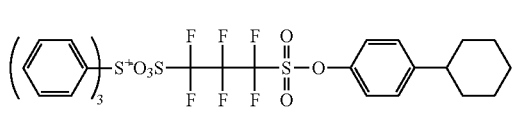
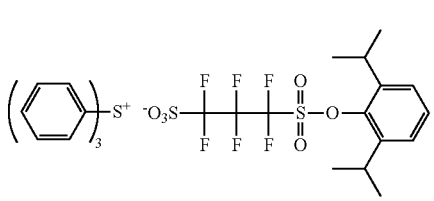
(z65) (z66)

-continued (z67) 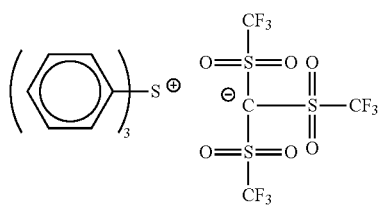 (z68) 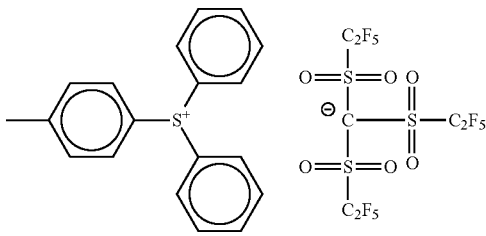

(z69) 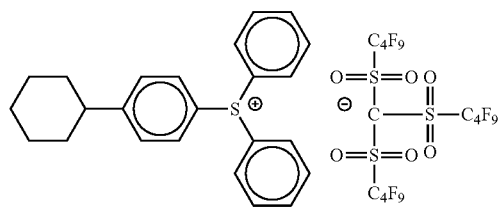 (z70) 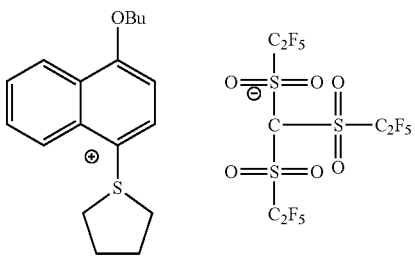

(z71) 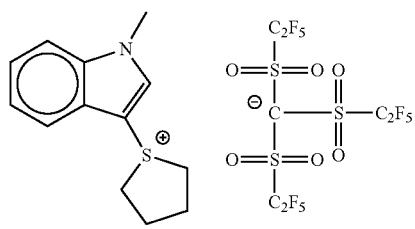 (z72) 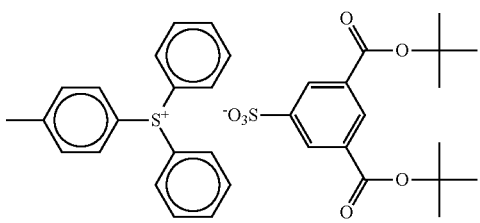

(z73) 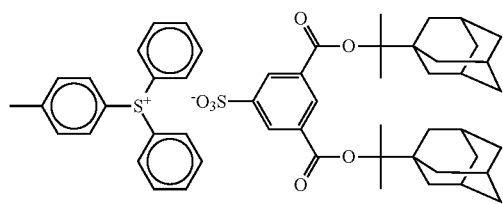 (z74) 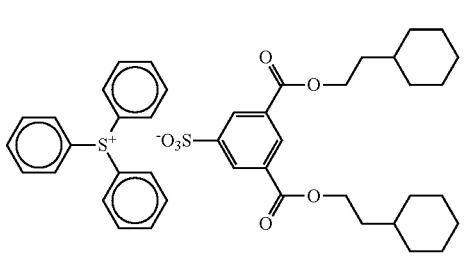

(z75) 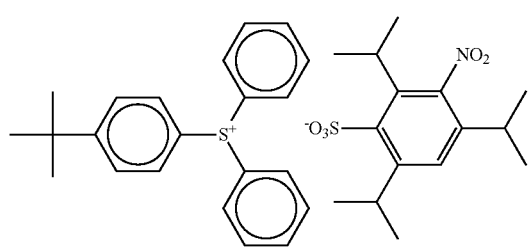 (z76) 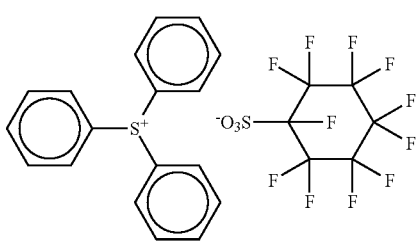

(z77) 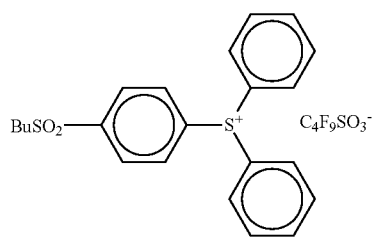 (z78) 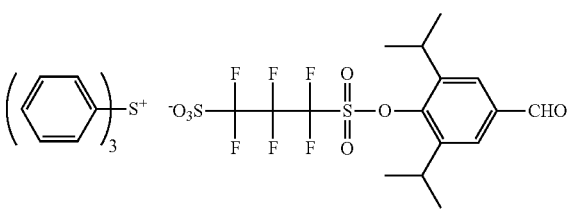

One of these photoacid generators may be used alone, or two or more species thereof may be used in combination. In the case of using two or more species in combination, compounds capable of generating two kinds of organic acids differing in the total atom number except for hydrogen atom by 2 or more are preferably combined.

The content of the photoacid generator is preferably from 0.1 to 20 mass %, more preferably from 0.5 to 10 mass %, still more preferably from 1 to 7 mass %, based on the entire solid content of the positive resist composition.

(C) Resin Having at Least Either a Fluorine Atom or a Silicon Atom

The positive resist composition of the present invention contains a resin (C) having at least either a fluorine atom or a silicon atom.

In the resin (C), the fluorine atom or silicon atom may be present in the main chain of the resin or may be substituted to the side chain.

The resin (C) is preferably a resin having a fluorine atom-containing alkyl group, a fluorine atom-containing cycloalkyl group or a fluorine atom-containing aryl group, as the partial structure having a fluorine atom.

The fluorine atom-containing alkyl group (preferably having a carbon number of 1 to 10, more preferably from 1 to 4) is a linear or branched alkyl group with at least one hydrogen atom being substituted by a fluorine atom and may further have another substituent.

The fluorine atom-containing cycloalkyl group is a monocyclic or polycyclic cycloalkyl group with at least one hydrogen atom being substituted by a fluorine atom and may further have another substituent.

The fluorine atom-containing aryl group is an aryl group (e.g., phenyl, naphthyl) with at least one hydrogen atom being substituted by a fluorine atom and may further have another substituent.

Specific examples of the fluorine atom-containing alkyl group, fluorine atom-containing cycloalkyl group and fluorine atom-containing aryl group are set forth below, but the present invention is not limited thereto.

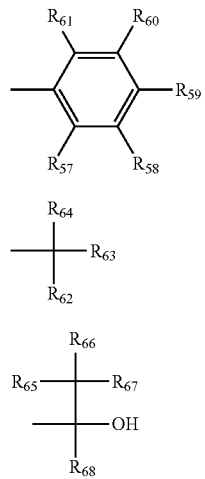

(F2)

(F3)

(F4)

In formulae (F2) to (F4), $R_{57}$ to $R_{68}$ each independently represents a hydrogen atom, a fluorine atom or an alkyl group, provided that at least one of $R_{57}$ to $R_{61}$, at least one of $R_{62}$ to $R_{64}$ and at least one of $R_{65}$ to $R_{68}$ are a fluorine atom or an alkyl group (preferably having a carbon number of 1 to 4) with at least one hydrogen atom being substituted by a fluorine atom. $R_{57}$ to $R_{61}$ and $R_{65}$ to $R_{67}$ all are preferably a fluorine atom. $R_{62}$, $R_{63}$ and $R_{68}$ each is preferably an alkyl group (preferably having a carbon number of 1 to 4) with at least one hydrogen atom being substituted by a fluorine atom, more preferably a perfluoroalkyl group having a carbon number of 1 to 4. $R_{62}$ and $R_{63}$ may combine with each other to form a ring.

Specific examples of the group represented by formula (F2) include p-fluorophenyl group, pentafluorophenyl group and 3,5-di(trifluoromethyl)phenyl group.

Specific examples of the group represented by formula (F3) include trifluoroethyl group, pentafluoropropyl group, pentafluoroethyl group, heptafluorobutyl group, hexafluoroisopropyl group, heptafluoroisopropyl group, hexafluoro(2-methyl)isopropyl group, nonafluorobutyl group, octafluoroisobutyl group, nonafluorohexyl group, nonafluoro-tert-butyl group, perfluoroisopentyl group, perfluorooctyl group, perfluoro(trimethyl)hexyl group, 2,2,3,3-tetrafluorocyclobutyl group and perfluorocyclohexyl group. Among these, preferred are hexafluoroisopropyl group, heptafluoroisopropyl group, hexafluoro(2-methyl)isopropyl group, octafluoroisobutyl group, nonafluoro-tert-butyl group and perfluoroisopentyl group, more preferred are hexafluoroisopropyl group and heptafluoroisopropyl group.

Specific examples of the group represented by formula (F4) include —C(CF$_3$)$_2$OH, —C(C$_2$F$_5$)$_2$OH, —C(CF$_3$)(CH$_3$)OH and —CH(CF$_3$)OH, with —C(CF$_3$)$_2$OH being preferred.

The resin (C) is preferably a resin having an alkyl silyl structure (preferably a trialkylsilyl group) or a cyclic siloxane structure, as the partial structure having a silicon atom.

Specific examples of the alkylsilyl structure and cyclic siloxane structure include the groups represented by the following formulae (CS-1) to (CS-3):

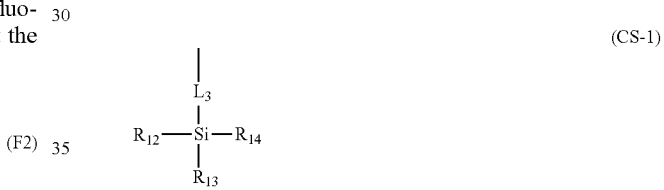

(CS-1)

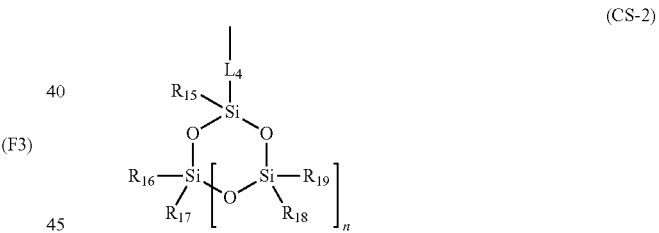

(CS-2)

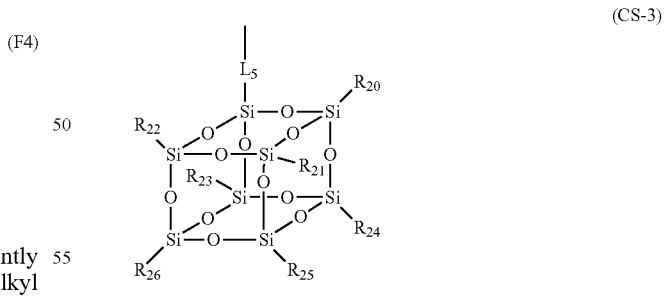

(CS-3)

In formulae (CS-1) to (CS-3), $R_{12}$ to $R_{26}$ each independently represents a linear or branched alkyl group (preferably having a carbon number of 1 to 20) or a cycloalkyl group (preferably having a carbon number of 3 to 20).

$L_3$ to $L_5$ each represents a single bond or a divalent linking group. The divalent linking group is a sole group or a combination of two or more groups, selected from the group consisting of an alkylene group, a phenyl group, an ether group, a thioether group, a carbonyl group, an ester group, an amide group, a urethane group and a urea group.

The resin (C) is a resin containing at least one member selected from the group consisting of repeating units represented by the following formulae (C-I) to (C-V):

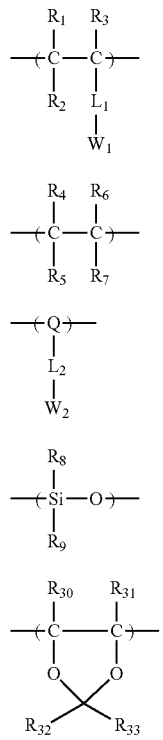

(C-I)

(C-II)

(C-III)

(C-IV)

(C-V)

In formulae (C-I) to (C-V), $R_1$ to $R_3$ each independently represents a hydrogen atom, a fluorine atom, a linear or branched alkyl group having a carbon number of 1 to 4, or a linear or branched fluorinated alkyl group having a carbon number of 1 to 4.

$W_1$ and $W_2$ each represents an organic group having at least either a fluorine atom or a silicon atom.

$R_4$ to $R_7$ each independently represents a hydrogen atom, a fluorine atom, a linear or branched alkyl group having a carbon number of 1 to 4, or a linear or branched fluorinated alkyl group having a carbon number of 1 to 4, provided that at least one of $R_4$ to $R_7$ represents a fluorine atom. $R_4$ and $R_5$, or $R_6$ and $R_7$ may form a ring.

$R_8$ represents a hydrogen atom or a linear or branched alkyl group having a carbon number of 1 to 4.

$R_9$ represents a linear or branched alkyl group having a carbon number of 1 to 4, or a linear or branched fluorinated alkyl group having a carbon number of 1 to 4.

$L_1$ and $L_2$ each represents a single bond or a divalent linking group having the same meaning as that for $L_3$ to $L_5$ above.

Q represents a monocyclic or polycyclic aliphatic group, that is an atomic group for forming an alicyclic structure, containing two bonded carbon atoms (C—C).

$R_{30}$ and $R_{31}$ each independently represents a hydrogen or a fluorine atom.

$R_{32}$ and $R_{33}$ each independently represents an alkyl group, a cycloalkyl group, a fluorinated alkyl group or a fluorinated cycloalkyl group, provided that in the repeating unit represented by the formula (C-V), at least one of $R_{30}$, $R_{31}$, $R_{32}$ and $R_{33}$ has at least one fluorine atom.

The resin (C) preferably has a repeating unit represented by the formula (C-I), and more preferably has any one of the following formulae (C-Ia) to (C-Id):

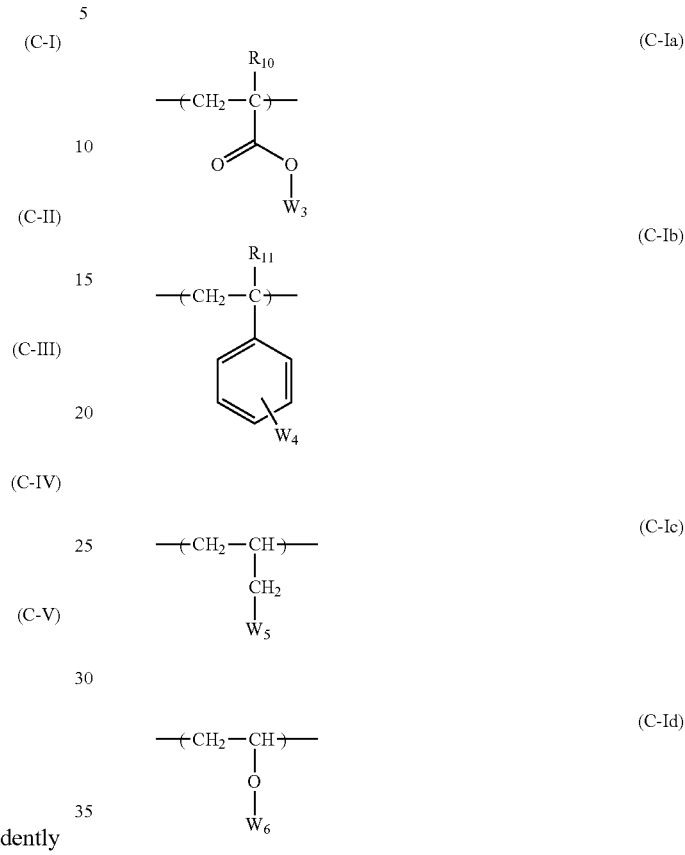

(C-Ia)

(C-Ib)

(C-Ic)

(C-Id)

In formulae (C-Ia) to (C-Id), $R_{10}$ and $R_{11}$ represents a hydrogen atom, a fluorine atom, a linear or branched alkyl group having a carbon number of 1 to 4, or a linear or branched fluorinated alkyl group having a carbon number of 1 to 4.

$W_3$ to $W_6$ each represents an organic group having one or more of at least either a fluorine atom or a silicon atom.

When $W_1$ to $W_6$ are an organic group having a fluorine atom, the organic group is preferably a fluorinated linear or branched alkyl or cycloalkyl group having a carbon number of 1 to 20, or a fluorinated linear, branched or cyclic alkyl ether group having a carbon number of 1 to 20.

Examples of the fluorinated alkyl group of $W_1$ to $W_6$ include a trifluoroethyl group, a pentafluoropropyl group, a hexafluoroisopropyl group, a hexafluoro(2-methyl)isopropyl group, a heptafluorobutyl group, a heptafluoroisopropyl group, an octafluoroisobutyl group, a nonafluorohexyl group, a nonafluoro-tert-butyl group, a perfluoroisopentyl group, a perfluorooctyl group and a perfluoro(trimethyl)hexyl group.

When $W_1$ to $W_6$ are an organic group having a silicon atom, the organic group preferably has an alkylsilyl structure or a cyclic siloxane structure. Specific examples thereof include the groups represented by formulae (CS-1) to (CS-3).

Specific examples of the repeating unit represented by formula (C-I) are set forth below. X represents a hydrogen atom, —$CH_3$, —F or —$CF_3$.

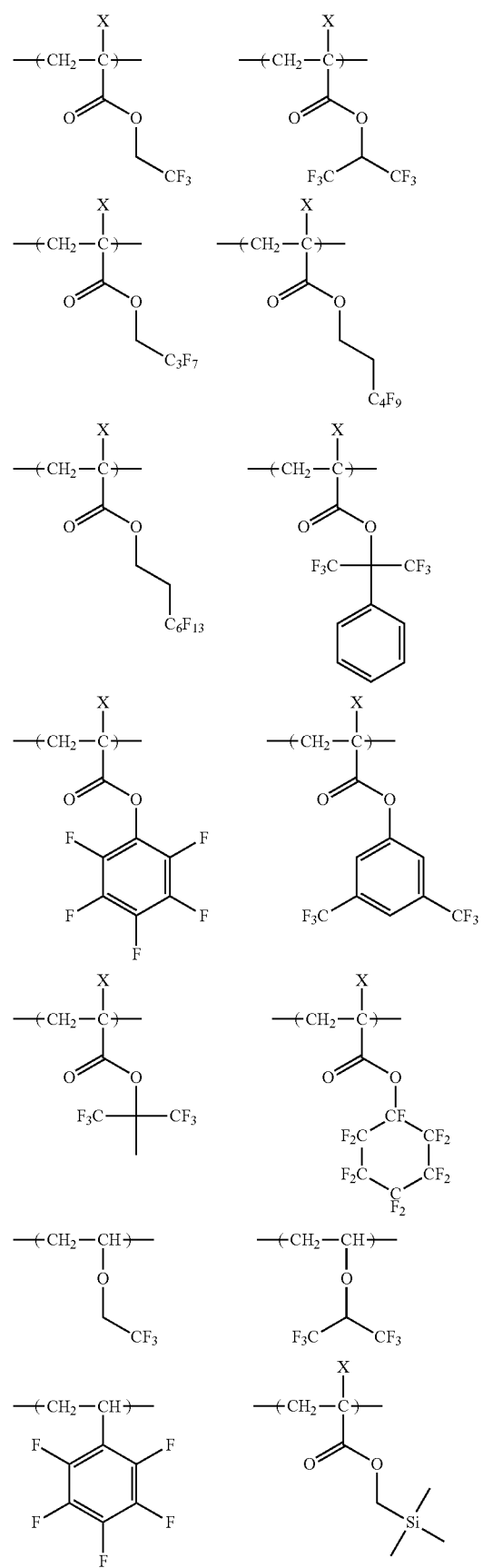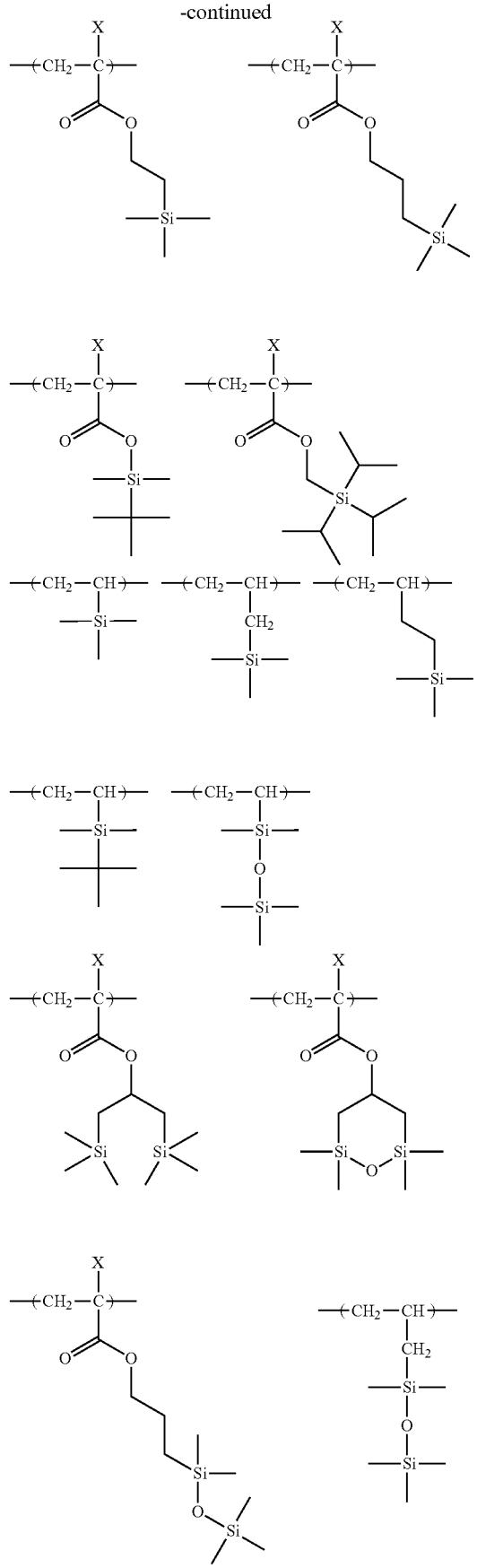

-continued

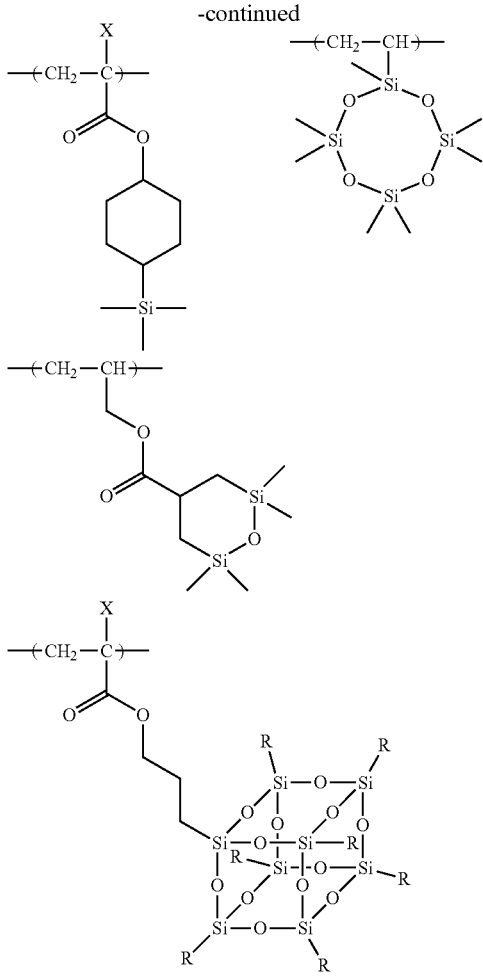

R = CH$_3$, C$_2$H$_5$, C$_3$H$_7$, C$_4$H$_9$

The resin (C) is preferably any one resin selected from the following (C-1) to (C-6):

(C-1) a resin containing (a) a repeating unit having a fluoroalkyl group (preferably having a carbon number of 1 to 4), more preferably containing only the repeating unit (a), (C-2) a resin containing (b) a repeating unit having a trialkylsilyl group or a cyclic siloxane structure, more preferably containing only the repeating unit (b), (C-3) a resin containing (a) a repeating unit having a fluoroalkyl group (preferably having a carbon number of 1 to 4) and (c) a repeating unit having a branched alkyl group (preferably having a carbon number of 4 to 20), a cycloalkyl group (preferably having a carbon number of 4 to 20), a branched alkenyl group (preferably having a carbon number of 4 to 20), a cycloalkenyl group (preferably having a carbon number of 4 to 20) or an aryl group (preferably having a carbon number of 4 to 20), more preferably a copolymerization resin of the repeating unit (a) and the repeating unit (c), (C-4) a resin containing (b) a repeating unit having a trialkylsilyl group or a cyclic siloxane structure and (c) a, repeating unit having a branched alkyl group (preferably having a carbon number of 4 to 20), a cycloalkyl group (preferably having a carbon number of 4 to 20), a branched alkenyl group (preferably having a carbon number of 4 to 20), a cycloalkenyl group (preferably having a carbon number of 4 to 20) or an aryl group (preferably having a carbon number of 4 to 20), more preferably a copolymerization resin of the repeating unit (b) and the repeating unit (c), (C-5) a resin containing (a) a repeating unit having a fluoroalkyl group (preferably having a carbon number of 1 to 4) and (b) a repeating unit having a trialkylsilyl group or a cyclic siloxane structure, more preferably a copolymerization resin of the repeating unit (a) and the repeating unit (b), and (C-6) a resin containing (a) a repeating unit having a fluoroalkyl group (preferably having a carbon number of 1 to 4), (b) a repeating unit having a trialkylsilyl group or a cyclic siloxane structure, and (c) a repeating unit having a branched alkyl group (preferably having a carbon number of 4 to 20), a cycloalkyl group (preferably having a carbon number of 4 to 20), a branched alkenyl group (preferably having a carbon number of 4 to 20), a cycloalkenyl group (preferably having a carbon number of 4 to 20) or an aryl group (preferably having a carbon number of 4 to 20), more preferably a copolymerization resin of the repeating unit (a), the repeating unit (b) and the repeating unit (c).

As for the repeating unit (c) having a branched alkyl group, a cycloalkyl group, a branched alkenyl group, a cycloalkenyl group or an aryl group in the resins (C-3), (C-4) and (C-6), in view of hydrophilicity/hydrophobicity, interaction and the like, an appropriate functional group can be introduced, but from the standpoint of the followability for the immersion liquid receding contact angle, a functional group having no polar group is preferred.

In the resins (C-3), (C-4) and (C-6), the content of the repeating unit (a) having a fluoroalkyl group and/or the repeating unit (b) having a trialkylsilyl group or a cyclic siloxane structure is preferably from 20 to 99 mol %.

The resin (C) is preferably a resin having a repeating unit represented by the following formula (Ia):

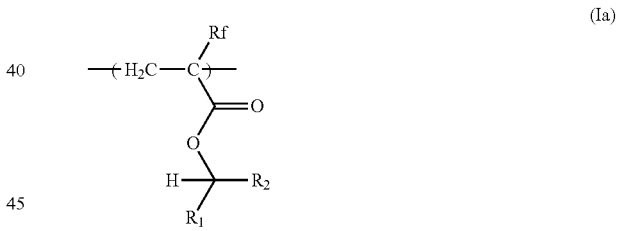

(Ia)

In formula (Ia), Rf represents a fluorine atom or an alkyl group with at least one hydrogen atom being substituted by a fluorine atom.

R$_1$ represents an alkyl group.

R$_2$ represents a hydrogen atom or an alkyl group.

In formula (Ia), the alkyl group with at least one hydrogen atom being substituted by a fluorine atom of Rf is preferably an alkyl group having a carbon number of 1 to 3, more preferably a trifluoromethyl group.

The alkyl group of R$_1$ is preferably a linear or branched alkyl group having a carbon number of 3 to 10, more preferably a branched alkyl group having a carbon number of 3 to 10.

The alkyl group of R$_2$ is preferably a linear or branched alkyl group having a carbon number of 1 to 10, and more preferably a linear or branched alkyl group having a carbon number of 3 to 10.

Specific examples of the repeating unit represented by formula (Ia) are set forth below, but the present invention is not limited thereto.

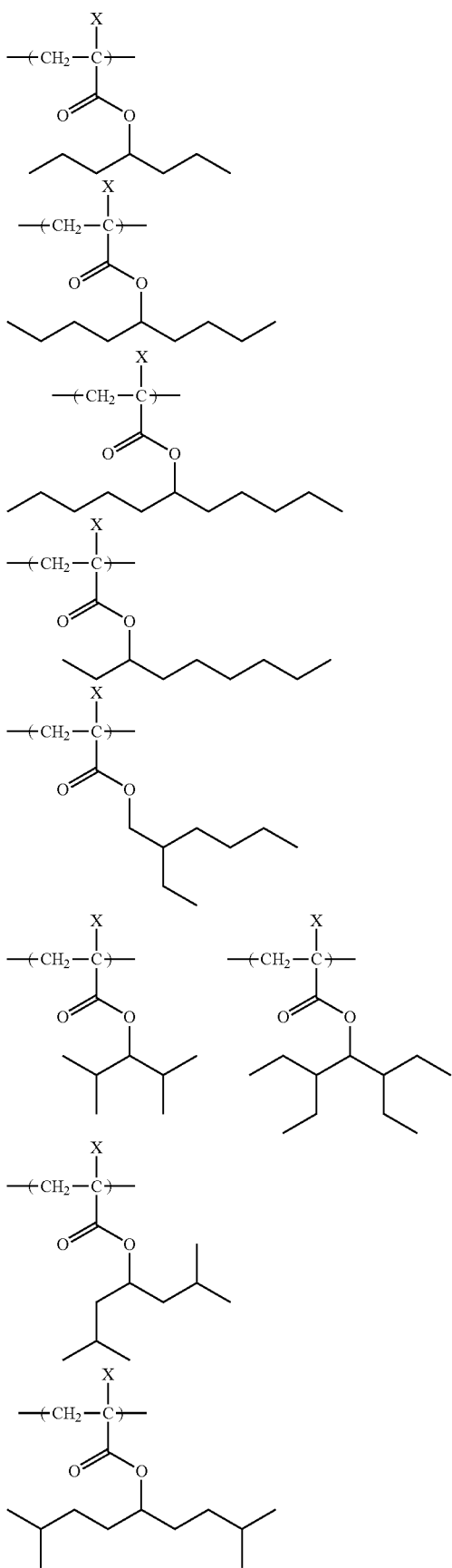

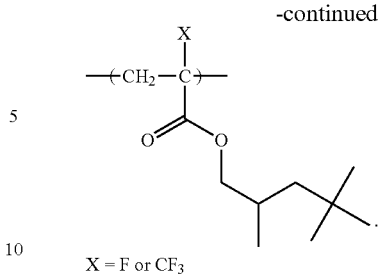

X = F or CF₃

The repeating unit represented by formula (Ia) can be formed by polymerizing a compound represented by the following formula (I):

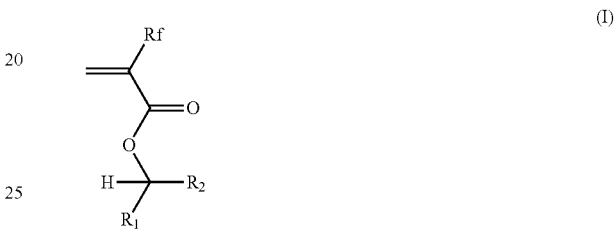

In formula (I), Rf represents a fluorine atom or an alkyl group with at least one hydrogen atom being substituted by a fluorine atom.

$R_1$ represents an alkyl group.

$R_2$ represents a hydrogen atom or an alkyl group.

Rf, $R_1$ and $R_2$ in formula (I) have the same meanings as Rf, $R_1$ and $R_2$ in formula (Ia).

The compound represented by formula (I) is a novel compound.

As for the compound represented by formula (I), a commercially available product or a compound synthesized may be used. In the case of synthesizing the compound, this can be attained by chloriding a 2-trifluoromethyl methacrylic acid and then esterifying the acid chloride.

The resin (C) containing a repeating unit represented by formula (Ia) preferably further contains a repeating unit represented by the following formula (III):

In formula (III), $R_4$ represents an alkyl group, a cycloalkyl group, an alkenyl group, a cycloalkenyl group, a trialkylsilyl group or a group having a cyclic siloxane structure.

$L_6$ represents a single bond or a divalent linking group.

In formula (III), the alkyl group of $R_4$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The trialkylsilyl group is preferably a trialkylsilyl group having a carbon number of 3 to 20.

The group having a cyclic siloxane structure is preferably a group containing a cyclic siloxane structure having a carbon number of 3 to 20.

The divalent linking group of $L_6$ is preferably an alkylene group (preferably having a carbon number of 1 to 5) or an oxy group.

Specific examples of the resin (C) having a repeating unit represented by formula (Ia) are set forth below, but the present invention is not limited thereto.

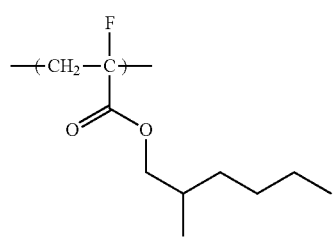

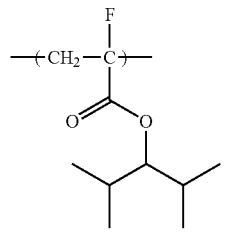 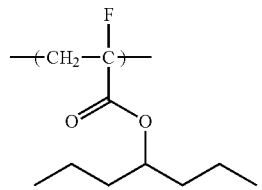

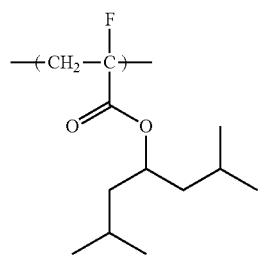

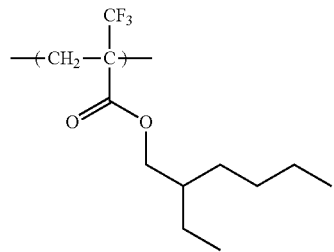 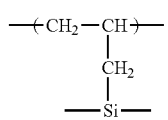

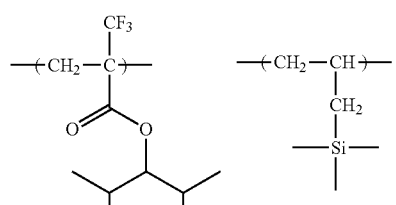

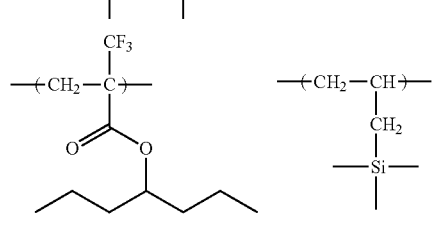

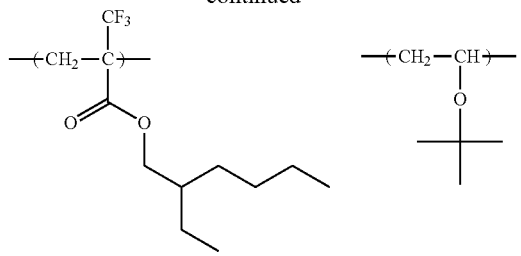

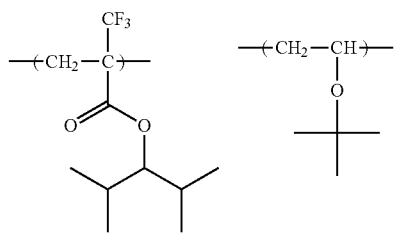

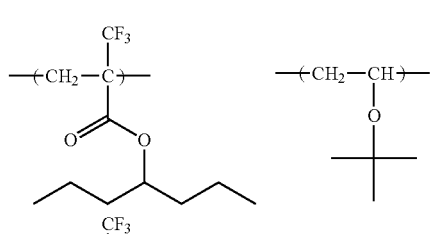

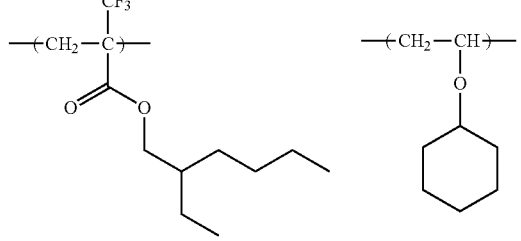

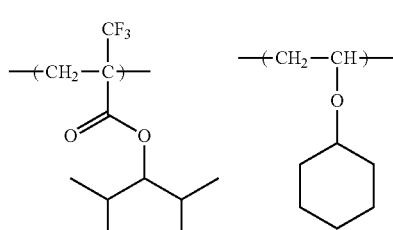

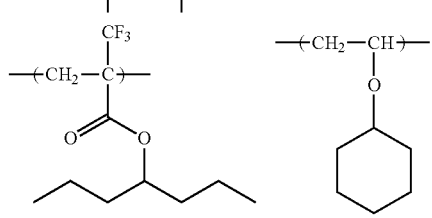

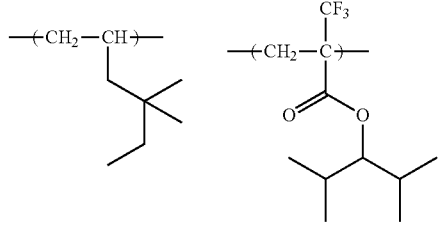

71
-continued
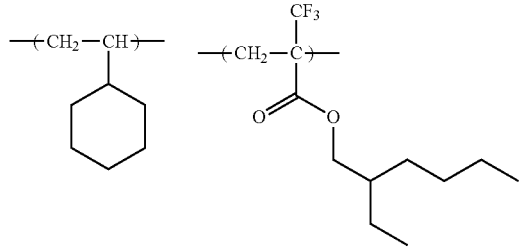
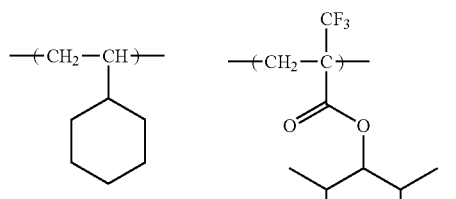
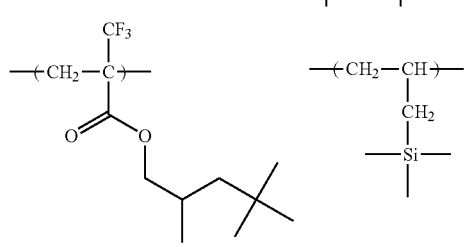
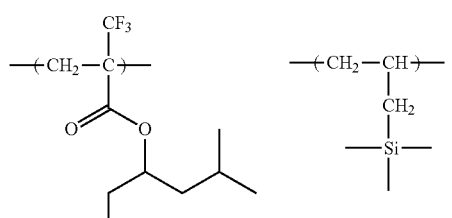
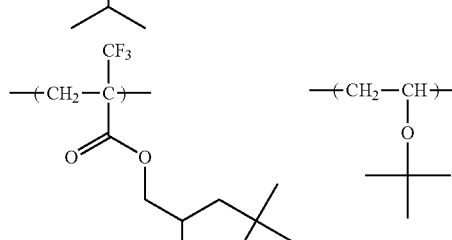
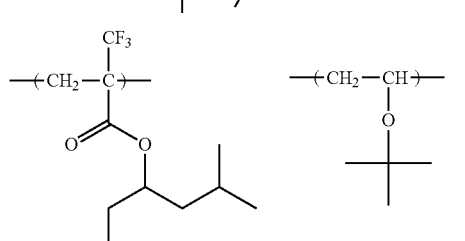
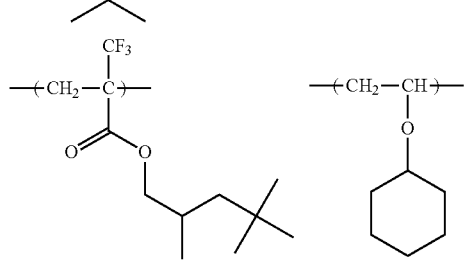
72
-continued
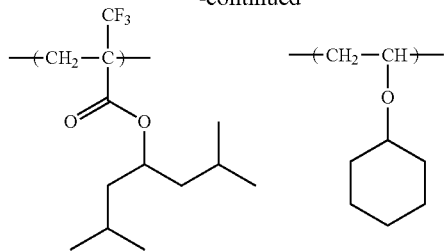
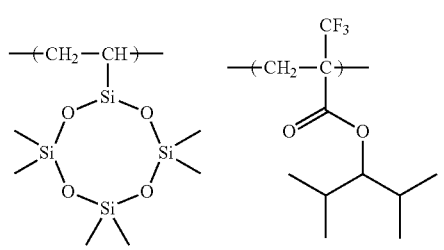
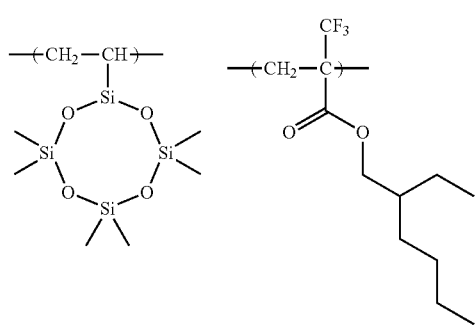
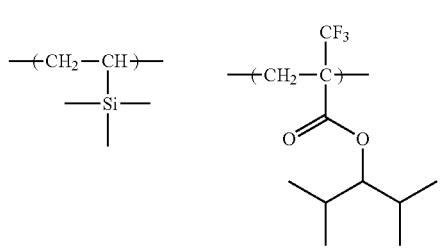
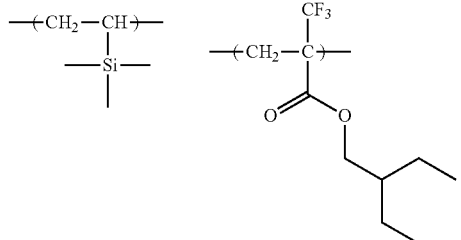
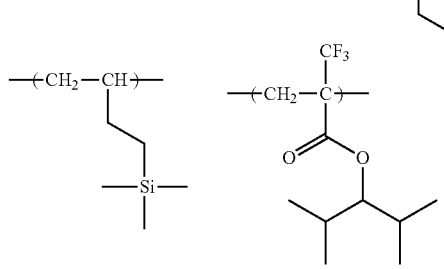

-continued

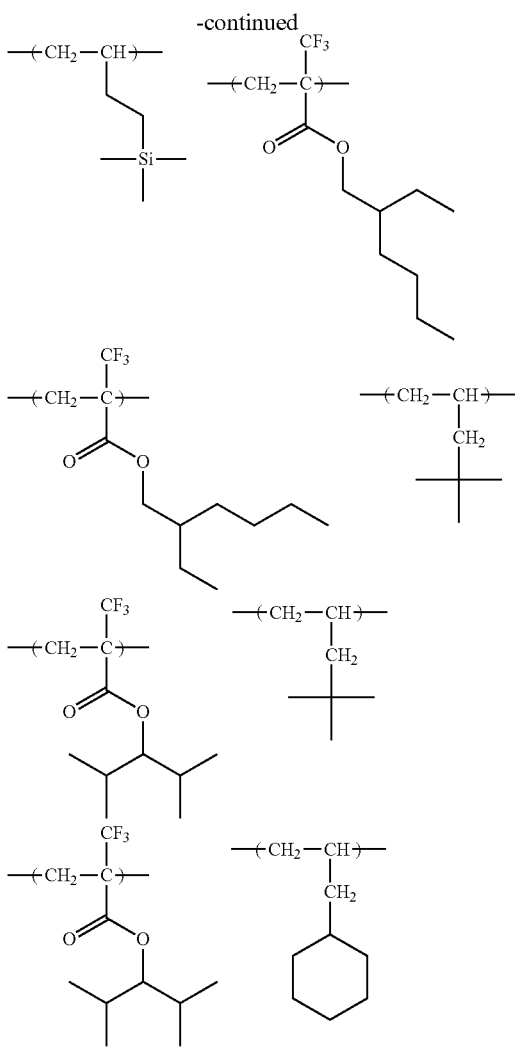

The resin (C) is preferably a resin containing a repeating unit represented by the following formula (II) and a repeating unit represented by the following formula (III):

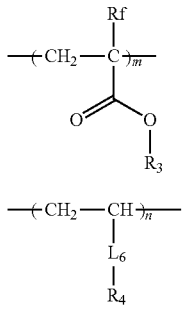

In formulae (II) and (III), Rf represents a fluorine atom or an alkyl group with at least one hydrogen atom being substituted by a fluorine atom.

$R_3$ represents an alkyl group, a cycloalkyl group, an alkenyl group or a cycloalkenyl group, or a group formed after two or more of these groups are combined.

$R_4$ represents an alkyl group, a cycloalkyl group, an alkenyl group, a cycloalkenyl group, a trialkylsilyl group or a group having a cyclic siloxane structure, or a group formed after two or more of these groups are combined.

In each of the alkyl group, cycloalkyl group, alkenyl group, cycloalkenyl group and trialkylsilyl group of $R_3$ and $R_4$, an appropriate functional group can be introduced. However, in view of followability of the immersion liquid, the functional group is preferably free of a polar group and more preferably unsubstituted.

$L_6$ represents a single bond or a divalent linking group.

0<m<100.

0<n<100.

In formula (II), Rf has the same meaning as Rf in formula (Ia).

The alkyl group of $R_3$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

$L_6$ represents preferably a single bond, a methylene group, an ethylene group or an ether group.

m=30 to 70 and n=30 to 70 are preferred, and m=40 to 60 and n=40 to 60 are more preferred.

Specific examples of the resin (C) containing a repeating unit represented by formula (II) and a repeating unit represented by formula (III) are set forth below, but the present invention is not limited thereto.

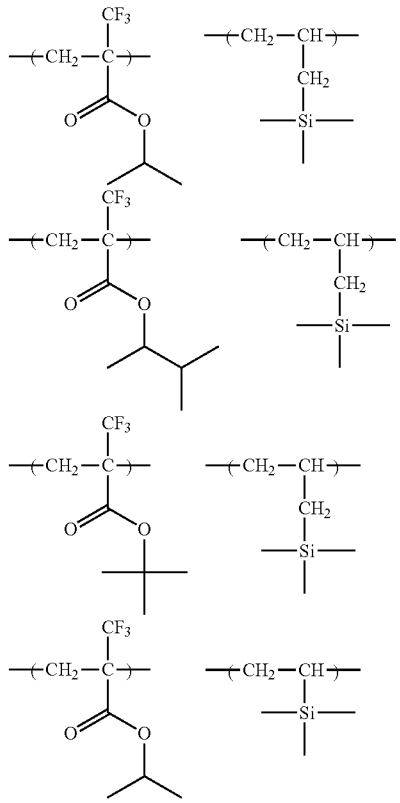

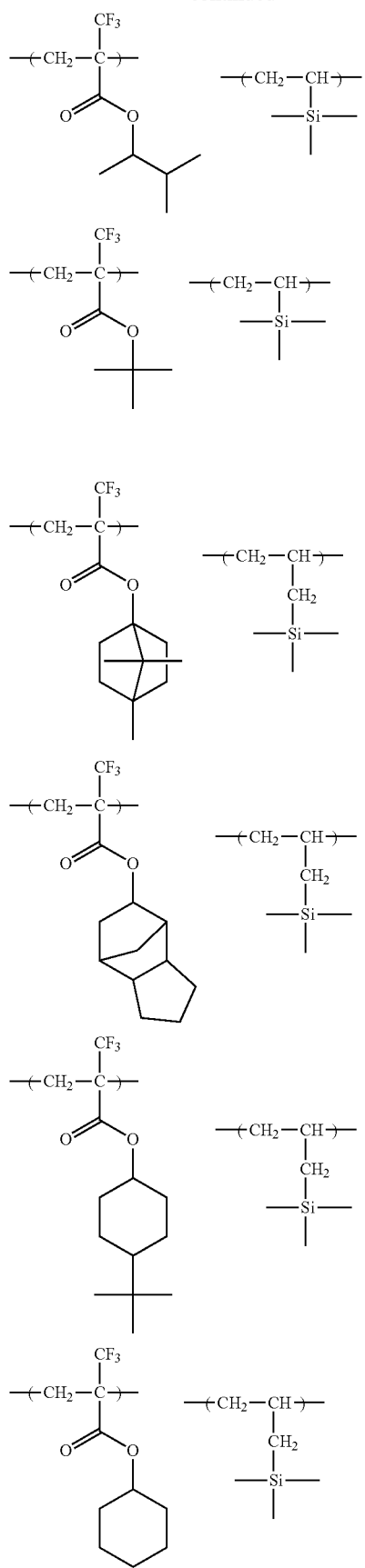
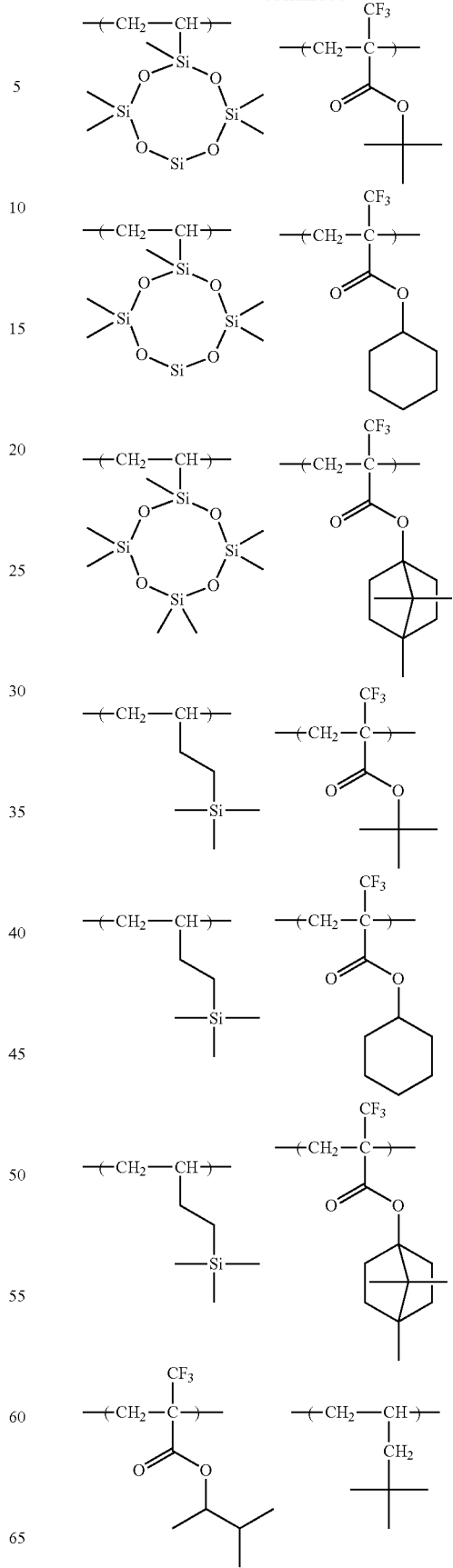

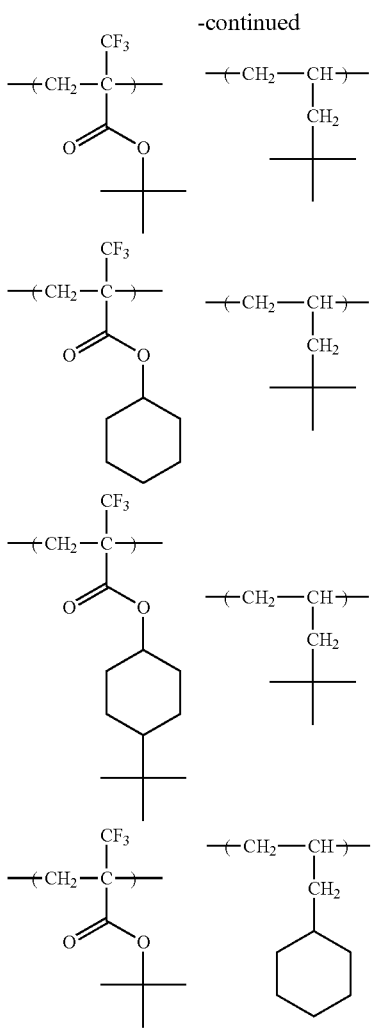

The resin (C) may contain a repeating unit represented by the following formula (VIII):

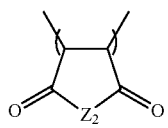

(VIII)

In formula (VIII), $Z_2$ represents —O— or —N($R_{41}$)—. $R_{41}$ represents a hydrogen atom, a hydroxyl group, an alkyl group or —OSO$_2$—$R_{42}$. $R_{42}$ represents an alkyl group, a cycloalkyl group or a camphor residue. The alkyl group of $R_{41}$ and $R_{42}$ may be substituted by a halogen atom (preferably fluorine atom) or the like.

The resin (C) is preferably solid at ordinary temperature (25° C.). Furthermore, the glass transition temperature (Tg) is preferably from 50 to 200° C., more preferably from 80 to 160° C.

When the resin is solid at 25° C., this means that the melting point is 25° C. or more.

The glass transition temperature (Tg) can be measured by a scanning calorimeter (Differential Scanning calorimeter). For example, after once elevating the temperature of the sample and then cooling it, the value by which the specific volume is changed when the temperature of the sample is again elevated at 5° C./min is analyzed, whereby the glass transition temperature can be measured.

The resin (C) is preferably stable to an acid and insoluble in an alkali developer.

In view of followability of the immersion liquid, the resin (C) is preferably free of (x) an alkali-soluble group, (y) a group which decomposes under the action of an alkali (alkali developer) to increase the solubility in an alkali developer and (z) a group which decomposes under the action of an acid to increase the solubility in a developer.

In the resin (C), the total amount of repeating units having an alkali-soluble group or a group of which solubility in a developer increases under the action of an acid or an alkali is preferably 20 mol % or less, more preferably from 0 to 10 mol %, still more preferably from 0 to 5 mol %, based on all repeating units constituting the resin (C).

Also, unlike a surfactant generally used for resists, the resin (C) does not contain an ionic bond or a hydrophilic group such as (poly(oxyalkylene)) group. The followability of the immersion liquid tends to decrease if the resin (C) contains a hydrophilic polar group, and therefore, it is more preferred to not contain a polar group selected from a hydroxyl group, alkylene glycols and a sulfone group. Furthermore, an ether group bonded to the carbon atom of the main chain through a linking group gives rise to increase in the hydrophilicity and deterioration in the followability of immersion liquid and therefore, such an ether group is preferably not contained. On the other hand, an ether group bonded directly to the carbon atom of the main chain as in formula (III) is preferred, because activity as a hydrophobic group is sometimes expressed.

Examples of (x) the alkali-soluble group include groups having a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl) methylene group, a bis(alkylsulfonyl)-imide group, a tris(alkylcarbonyl)methylene group or a tris(alkylsulfonyl)methylene group.

Examples of (y) the group capable of decomposing under the action of an alkali (alkali developer) to increase the solubility in an alkali developer include a lactone group, an ester group, a sulfonamide group, an acid anhydride and an acid imide group.

Examples of the (z) group capable of decomposing under the action of an acid to increase the solubility in a developer include the same groups as those of the acid-decomposable group in the acid-decomposable resin (A).

However, the repeating unit represented by the following formula (pA-C) is not or scarcely decomposed under the action of an acid as compared with the acid-decomposable group of the resin (A) and is regarded as substantially non-acid-decomposable.

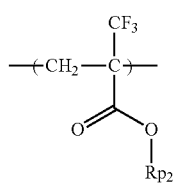

(pA-c)

In formula (pA-c), $Rp_2$ represents a hydrocarbon group having a tertiary carbon atom bonded to the oxygen atom in the formula.

In the case where the resin (C) contains a silicon atom, the silicon atom content is preferably from 2 to 50 mass %, more preferably from 2 to 30 mass %, based on the molecular weight of the resin (C). Also, the silicon atom-containing repeating unit preferably occupies from 10 to 100 mass %, more preferably from 20 to 100 mass %, in the resin (C).

In the case where the resin (C) contains a fluorine atom, the fluorine atom content is preferably from 5 to 80 mass %, more preferably from 10 to 80 mass %, based on the molecular weight of the resin (C). Also, the fluorine atom-containing repeating unit preferably occupies from 10 to 100 mass %, more preferably from 30 to 100 mass %, in the resin (C).

The standard polystyrene-reduced weight average molecular of the resin (C) is preferably from 1,000 to 100,000, more preferably from 1,000 to 50,000, still more preferably from 2,000 to 15,000, particularly more preferably from 3,000 to 15,000.

The residual monomer amount in the resin (C) is preferably from 0 to 10 mass %, more preferably from 0 to 5 mass %, still more preferably from 0 to 1 mass %. Also, in view of the resolution, resist profile and side wall, roughness or the like of the resist pattern, the molecular weight distribution (Mw/Mn, also called dispersity) is preferably from 1 to 5, more preferably from 1 to 3, still more preferably from 1 to 1.5.

The amount added of the resin (C) in the positive resist composition is preferably from 0.1 to 20 mass %, and more preferably from 0.1 to 10 mass %, based on the entire solid content of the resist composition. Furthermore, from 0.1 to 5 mass % is preferred, from 0.2 to 3.0 mass % is more preferred, and from 0.3 to 2.0 mass % is still more preferred.

Similarly to the acid-decomposable resin (A), it is preferred that the resin (C) has of course less impurities such as metal and also, the content of the residual monomer or oligomer component is not more than a specific value, for example, 0.1 mass % by HPLC. When these conditions are satisfied, not only the resist can be improved in the sensitivity, resolution, process stability, pattern profile and the like but also a resist ensuring that in-liquid foreign matter, sensitivity and the like are not changed in aging can be obtained.

The resin (C) may be a commercially available product of various types or may be synthesize by an ordinary method (for example, radical polymerization)). Examples of the synthesis method in general include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include tetrahydrofuran, 1,4-dioxane, ethers (e.g., diisopropyl ether), ketones (e.g., methyl ethyl ketone, methyl isobutyl ketone), an ester solvent (e.g., ethyl acetate), an amide solvent (e.g., dimethylformamide, diethylacetamide), and a solvent capable of dissolving the composition of the present invention, which is described later, such as propylene glycol monomethyl ether acetate, propylene glycol monomethyl ether and cyclohexanone. The polymerization is preferably performed by using the same solvent as the solvent used in the resist composition of the present invention. By the use of this solvent, generation of particles during storage can be suppressed.

The polymerization reaction is preferably performed in an inert gas atmosphere such as nitrogen and argon. As for the polymerization initiator, the polymerization is started by using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methyl-propionate). A chain transfer agent can be used according to need. The reaction concentration is usually from 5 to 50 mass %, preferably from 20 to 50 mass %, and more preferably from 30 to 50 mass %. The reaction temperature is usually from 10 to 150° C., preferably from 30 to 120° C., more preferably from 60 to 100° C.

After the completion of reaction, the reactant is allowed to cool to room temperature and purified. The purification may be performed by a normal method, for example, a liquid-liquid extraction method of applying water washing or combining an appropriate solvent to remove residual monomers or oligomer components; a purification method in a solution sate, such as ultrafiltration of removing by extraction only polymers having a molecular weight lower than a specific molecular weight; a reprecipitation method of adding dropwise the resin solution in a bad solvent to solidify the resin in the bad solvent and thereby remove residual monomers or the like; and a purification method in a solid state, such as washing of the resin with a bad solvent after separation by filtration. For example, the resin is precipitated as a solid through contact with a solvent in which the resin is sparingly soluble or insoluble (bad solvent) and which is in a volume amount of 10 times or less, preferably from 10 to 5 times, the reaction solution.

The solvent used at the operation of precipitation or reprecipitation from the polymer solution (precipitation or reprecipitation solvent) may be sufficient if it is a bad solvent to the polymer, and may be appropriately selected from, for example, a hydrocarbon (e.g., an aliphatic hydrocarbon such as pentane, hexane, heptane and octane; an alicyclic hydrocarbon such as cyclohexane and methylcyclohexane; an aromatic hydrocarbon such as benzene, toluene and xylene), a halogenated hydrocarbon (e.g., a halogenated aliphatic hydrocarbon such as methylene chloride, chloroform and carbon tetrachloride; a halogenated aromatic hydrocarbon such as chlorobenzene and dichlorobenzene), a nitro compound (e.g., nitromethane, nitroethane), a nitrile (e.g., acetonitrile, benzonitrile), an ether (e.g., a chain ether such as diethyl ether, diisopropyl ether, dimethoxyethane), a ketone (e.g., acetone, methyl ethyl ketone, diisobutyl ketone), an ester (e.g., ethyl acetate, butyl acetate), a carbonate (e.g., dimethyl carbonate, diethyl carbonate, ethylene carbonate, propylene carbonate), an alcohol (e.g., methanol, ethanol, propanol, isopropyl alcohol, butanol), a carboxylic acid (e.g., acetic acid), water, and a mixed solvent containing such a solvent. Among these, the precipitation or reprecipitation solvent is preferably a solvent containing at least an alcohol (particularly methanol or the like) or water. In such a solvent containing at least a hydrocarbon, the ratio of the alcohol (particularly, methanol or the like) to other solvents (for example, an ester such as ethyl acetate, and ethers such as tetrahydrofuran) is, for example, the former/the latter (volume ratio, at 25° C.)=from 10/90 to 99/1, preferably the former/the latter (volume ratio, at 25° C.)=from 30/70 to 98/2, more preferably the former/the latter (volume ratio, at 25° C.)=from 50/50 to 97/3.

The amount of the precipitation or reprecipitation solvent used may be appropriately selected by taking into account the efficiency, yield and the like, but in general, the amount used is from 100 to 10,000 parts by mass, preferably from 200 to 2,000 parts by mass, more preferably from 300 to 1,000 parts by mass, per 100 parts by mass of the polymer solution.

The nozzle bore diameter at the time of feeding the polymer solution into a precipitation or reprecipitation solvent (bad solvent) is preferably 4 mmϕ or less (for example, from 0.2 to 4 mmϕ, and the feeding rate (dropping rate) of the polymer solution into the bad solvent is, for example, in terms of a linear velocity, from 0.1 to 10 msec, preferably from 0.3 to 5 msec.

The precipitation or reprecipitation operation is preferably performed under stirring. Examples of the stirring blade which can be used for the stirring include a disc turbine, a fan turbine (including paddle), a curved vane turbine, an arrow feather turbine, a Pfaudler type, a bull margin type, an angled vane fan turbine, a propeller, a multistage type, an anchor type (or horseshoe type), a gate type, a double ribbon type and a screw type. The stirring is preferably further performed for 10 minutes or more, more preferably 20 minutes or more, after the completion of feeding of the polymer solution. If the stirring time is short, the monomer content in the polymer particle may not be sufficiently reduced. The mixing and stirring of the polymer solution and the bad solvent may also be performed by using a line mixer instead of the stirring-blade.

The temperature at the precipitation or reprecipitation may be appropriately selected by taking into account the efficiency or operability, but the temperature is usually on the order of 0 to 50° C., preferably in the vicinity of room temperature (for example, approximately from 20 to 35° C.). The precipitation or reprecipitation operation may be performed by using a commonly employed mixing vessel such as stirring tank according to a known method such as batch system and continuous system.

The precipitated or reprecipitated particulate polymer is usually subjected to commonly employed solid-liquid separation such as filtration and centrifugation, then dried and used. The filtration is performed by using a solvent-resistant filter element preferably under applied pressure. The drying is performed under atmospheric pressure or reduced pressure (preferably under reduced pressure) at a temperature of approximately from 30 to 100° C., preferably on the order of 30 to 50° C.

Incidentally, after the resin is once precipitated and separated, the resin may be again dissolved in a solvent and then put into contact with a solvent in which the resin is sparingly soluble or insoluble.

More specifically, the method may be a method comprising, after the completion of radical polymerization reaction, precipitating a resin by bringing the polymer into contact with a solvent in which the polymer is sparingly soluble or insoluble (step a), separating the resin from the solution (step b), anew dissolving the resin in a solvent to prepare a resin solution A (step c), precipitating a resin solid by bringing the resin solution A into contact with a solvent in which the resin is sparingly soluble or insoluble and which is in a volume amount of less than 10 times (preferably a volume amount of 5 times or less) the resin solution A (step d), and separating the precipitated resin (step e).

As for the solvent used for the preparation of the resin solution A, the same solvent as the solvent for dissolving the monomer at the polymerization reaction may be used, and the solvent may be the same as or different from the solvent used for the polymerization reaction.

(D) Solvent

Examples of the solvent which can be used for dissolving respective components described above to prepare a positive resist composition include an organic solvent such as alkylene glycol monoalkyl ether carboxylate, alkylene glycol monoalkyl ether, alkyl lactate, alkyl alkoxypropionate, cyclic lactone having a carbon number of 4 to 10, monoketone compound having a carbon number of 4 to 10 which may contain a ring, alkylene carbonate, alkyl alkoxyacetate and alkyl pyruvate.

Preferred examples of the alkylene glycol monoalkyl ether carboxylate include propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

Preferred examples of the alkylene glycol monoalkyl ether include propylene glycol monomethyl ether, propylene glycol monoethyl ether, propylene glycol monopropyl ether, propylene glycol monobutyl ether, ethylene glycol monomethyl ether and ethylene glycol monoethyl ether.

Preferred examples of the alkyl lactate include methyl lactate, ethyl lactate, propyl lactate and butyl lactate.

Preferred examples of the alkyl alkoxypropionate include ethyl 3-ethoxypropionate, methyl 3-methoxypropionate, methyl 3-ethoxypropionate and ethyl 3-methoxypropionate.

Preferred examples of the cyclic lactone having a carbon number of 4 to 10 include β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

Preferred examples of the monoketone compound having a carbon number of 4 to 10 which may contain a ring include 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

Preferred examples of the alkylene carbonate include propylene carbonate, vinylene carbonate, ethylene carbonate and butylene carbonate.

Preferred examples of the alkyl alkoxyacetate include 2-methoxyethyl acetate, 2-ethoxyethyl acetate, 2-(2-ethoxyethoxyl)ethyl acetate, 3-methoxy-3-methylbutyl acetate and 1-methoxy-2-propyl acetate.

Preferred examples of the alkyl pyruvate include methyl pyruvate, ethyl pyruvate and propyl pyruvate.

The solvent which can be preferably used includes a solvent having a boiling point of 130° C. or more at ordinary temperature and atmospheric pressure, and specific examples thereof include cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, 2-ethoxyethyl acetate, 2-(2-ethoxyethoxyl)ethyl acetate and propylene carbonate.

In the present invention, one of these solvents may be used alone, or two or more species thereof may be used in combination.

In the present invention, a mixed solvent prepared by mixing a solvent containing a hydroxyl group in the structure and a solvent not containing a hydroxyl group may be used as the organic solvent.

Examples of the solvent containing a hydroxyl group include ethylene glycol, ethylene glycol monomethyl ether ethylene glycol monoethyl ether, propylene glycol, propylene glycol monomethyl ether, propylene glycol monoethyl ether and ethyl lactate. Among these, propylene glycol monomethyl ether and ethyl lactate are preferred.

Examples of the solvent not containing a hydroxyl group include propylene glycol monomethyl ether acetate, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone and butyl acetate are preferred, and propylene glycol monomethyl ether acetate, ethyl ethoxypropionate and 2-heptanone are most preferred.

The mixing ratio (by mass) of the solvent containing a hydroxyl group and the solvent not containing a hydroxyl group is from 1/99 to 99/1, preferably from 10/90 to 90/10, more preferably from 20/80 to 60/40. A mixed solvent in which the solvent not containing a hydroxyl group is contained in an amount of 50 mass % or more is preferred in view of coating uniformity.

The solvent is preferably a mixed solvent of two or more species including propylene glycol monomethyl acetate.

(E) Basic Compound

The positive resist composition of the present invention preferably comprises (E) a basic compound for reducing the change of performance in aging from exposure until heating.

Preferred examples of the basic compound include compounds having a structure represented by any one of the following formulae (A) to (E):

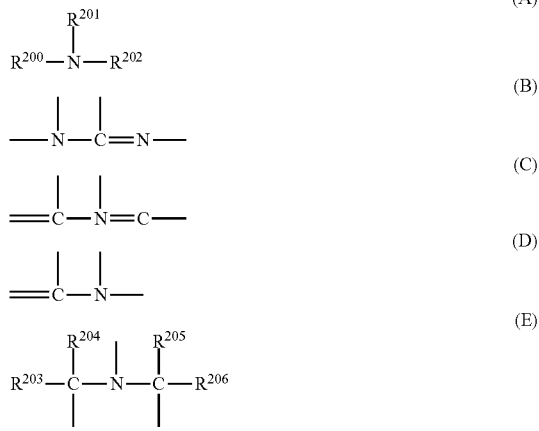

In formulae (A) to (E), $R^{200}$, $R^{201}$ and $R^{202}$, which may be the same or different, each represents a hydrogen atom, an alkyl group (preferably having a carbon number of 1 to 20), a cycloalkyl group (preferably having a carbon number of 3 to 20) or an aryl group (having a carbon number of 6 to 20), and $R^{201}$ and $R^{202}$ may combine with each other to form a ring.

As for the alkyl group, the alkyl group having a substituent is preferably an aminoalkyl group having a carbon number of 1 to 20, a hydroxyalkyl group having a carbon number of 1 to 20, or a cyanoalkyl group having a carbon number of 1 to 20.

$R^{203}$, $R^{204}$, $R^{205}$, and $R^{206}$, which may be the same or different, each represents an alkyl group having a carbon number of 1 to 20.

The alkyl group in these formulae (A) to (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include triarylsulfonium hydroxide, phenacylsulfonium hydroxide and sulfonium hydroxide having a 2-oxoalkyl group, specifically, triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. Examples of the compound having an onium carboxylate structure include a compound where the anion moiety of the compound having an onium hydroxide structure is converted into a carboxylate, such as acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline, N,N-dimethylaniline, N,N-dibutylaniline and N,N-dihexylaniline. Examples of the alkylamine derivative having a hydroxyl group and/or an ether bond include ethanolamine, diethanolamine, triethanolamine and tris(methoxyethoxyethyl)amine. Examples of the aniline derivative having a hydroxyl group and/or an ether bond include N,N-bis(hydroxyethyl)aniline.

One of these basic compounds is used alone, or two or more species thereof are used in combination.

The amount of the basic compound used is usually from 0.001 to 10 mass %, preferably from 0.01 to 5 mass %, based on the solid content of the positive resist composition.

The ratio of the acid generator and the basic compound used in the composition is preferably acid generator/basic compound (by mol)=from 2.5 to 300. That is, the molar ratio is preferably 2.5 or more in view of sensitivity and resolution and preferably 300 or less from the standpoint of suppressing the reduction in resolution due to thickening of the resist pattern in aging after exposure until heat treatment. The acid generator/basic compound (by mol) is more preferably from 5.0 to 200, still more preferably from 7.0 to 150.

(F) Surfactant

The positive resist composition of the present invention preferably further comprises (F) a surfactant, more preferably any one fluorine-containing and/or silicon-containing surfactant (a fluorine-containing surfactant, a silicon-containing surfactant or a surfactant containing both a fluorine atom and a silicon atom) or two or more species thereof.

When the positive resist composition of the present invention contains the (F) surfactant, a resist pattern with good sensitivity, resolution and adhesion as well as less development defects can be obtained when an exposure light source of 250 nm or less, particularly 220 nm or less, is used.

Examples of the fluorine-containing and/or silicon-containing surfactant include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include a fluorine-containing surfactant and a silicon-containing surfactant, such as EFtop EF301 and EF303 (produced by Shin-Akita Kasei K. K.); Florad FC430, 431 and 4430 (produced by Sumitomo 3M Inc.); Megafac F171, F173, F176, F189, F113, F110, F177, F120 and R08 (produced by Dainippon Ink & Chemicals, Inc.); Surflon S-382, SC101, 102, 103, 104, 105 and 106 (produced by Asahi Glass Co., Ltd.); Troysol S-366 (produced by Troy Chemical); GF-300 and GF-150 (produced by Toagosei Chemical Industry Co., Ltd.); Surflon S-393 (produced by Seimi Chemical Co., Ltd.); Eftop EF121, EF122A, EF122B, RF122C, EF125M, EF135M, EF351, 352, EF801, EF802 and EF601 (produced by JEMCO Inc.); PF636, PF656, PF6320 and PF6520 (produced by OMNOVA); and FTX-204D, 208G, 218G, 230G, 204D, 208D, 212D, 218 and 222D (produced by NEOS Co., Ltd.). In addition, polysiloxane polymer KP-341 (produced by Shin-Etsu Chemical Co., Ltd.) may also be used as the silicon-containing surfactant.

Other than those known surfactants, a surfactant using a polymer having a fluoro-aliphatic group derived from a fluoro-aliphatic compound which is produced by a telomerization process (also called a telomer process) or an oligomerization process (also called an oligomer process), may be used. The fluoro-aliphatic compound can be synthesized by the method described in JP-A-2002-90991.

The polymer having a fluoro-aliphatic group is preferably a copolymer of a fluoro-aliphatic group-containing monomer with a (poly(oxyalkylene)) acrylate and/or a (poly(oxyalkylene)) methacrylate, and the polymer may have an irregular distribution or may be a block copolymer. Examples of the poly(oxyalkylene) group include a poly(oxyethylene) group, a poly(oxypropylene) group and a poly(oxybutylene) group. This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer and a (poly(oxyalkylene)) acrylate (or methacrylate) is not limited only to a binary copolymer but may also be a ternary or greater copolymer obtained by simultaneously copolymerizing two or more different fluoro-aliphatic group-containing monomers or two or more different (poly(oxyalkylene)) acrylates (or methacrylates).

Examples thereof include, as the commercially available surfactant, Megafac F178, F-470, F-473, F-475, F-476 and F-472 (produced by Dainippon Ink &. Chemicals, Inc.) and further include a copolymer of an acrylate (or methacrylate) having a $C_6F_{13}$ group with a (poly(oxyalkylene)) acrylate (or methacrylate), and a copolymer of an acrylate (or methacrylate) having a $C_3F_7$ group with a (poly(oxyethylene)) acrylate (or methacrylate) and a (poly(oxypropylene)) acrylate (or methacrylate).

In the present invention, a surfactant other than the fluorine-containing and/or silicon-containing surfactant may also be used. Specific examples thereof include a nonionic surfactant such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkylallyl ethers (e.g., polyoxyethylene octylphenol ether, polyoxyethylene nonylphenol ether), polyoxyethylene.polyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate) and polyoxyethylene sorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate).

One of these surfactants may be used alone, or several species thereof may be used in combination.

The amount of the (F) surfactant used is preferably from 0.01 to 10 mass %, more preferably from 0.1 to 5 mass %, based on the entire amount of the positive resist composition (excluding the solvent).

(G) Onium Carboxylate

The positive resist composition of the present invention may comprise (G) an onium carboxylate. Examples of the onium carboxylate include sulfonium carboxylate, iodonium carboxylate and ammonium carboxylate. In particular, the (G) onium carboxylate is preferably an iodonium salt or a sulfonium salt. Furthermore, the carboxylate residue of the (H) onium carboxylate for use in the present invention preferably contains no aromatic group and no carbon-carbon double bond. The anion moiety is preferably a linear, branched, monocyclic or polycyclic alkylcarboxylate anion having a carbon number of 1 to 30, more preferably an anion of the carboxylic acid with the alkyl group being partially or entirely fluorine-substituted. The alkyl chain may contain an oxygen atom. By virtue of such a construction, the transparency to light of 220 nm or less is ensured, the sensitivity and the resolution are enhanced, and the defocus latitude depended on line pitch and the exposure margin are improved.

Examples of the anion of a fluorine-substituted carboxylic acid include anions of fluoroacetic acid, difluoroacetic acid, trifluoroacetic acid, pentafluoropropionic acid, heptafluorobutyric acid, nonafluoropentanoic acid, perfluorododecanoic acid, perfluoro-tridecanoic acid, perfluorocyclohexanecarboxylic acid and 2,2-bistrifluoromethylpropionic acid.

These (G) onium carboxylates can be synthesized by reacting a sulfonium, iodonium or ammonium hydroxide and a carboxylic acid with silver oxide in an appropriate solvent.

The content of the (G) onium carboxylate in the composition is generally from 0.1 to 20 mass %, preferably from 0.5 to 10 mass %, more preferably from 1 to 7 mass %, based on the entire solid content of the composition.

(H) Other Additives

The positive resist composition of the present invention may further contain, for example, a dye, a plasticizer, a photosensitizer, a light absorbent, an alkali-soluble resin, a dissolution inhibitor, and a compound for accelerating dissolution in a developer (for example, a phenol compound having a molecular weight of 1,000 or less, or a carboxyl group-containing alicyclic or aliphatic compound), if desired.

The phenol compound having a molecular weight of 1,000 or less can be easily synthesized by one skilled in the art with reference to the methods described, for example, in JP-A-4-122938, JP-A-2-28531, U.S. Pat. No. 4,916,210 and European Patent 219294.

Specific examples of the carboxyl group-containing alicyclic or aliphatic compound include, but are not limited to, a carboxylic acid derivative having a steroid structure, such as cholic acid, deoxycholic acid and lithocholic acid, an adamantanecarboxylic acid derivative, an adamantanedicarboxylic acid, a cyclohexanecarboxylic acid and a cyclohexanedicarboxylic acid.

(I) Pattern Forming Method

The positive resist composition of the present invention is preferably used in a film thickness of 30 to 500 nm, more preferably from 30 to 250 nm, and still more preferably from 30 to 200 nm, from the standpoint of enhancing the resolving power. Such a film thickness can be obtained by setting the solid content concentration in the positive resist composition to an appropriate range and thereby giving an appropriate viscosity to enhance the coatability and film-forming property.

The entire solid content concentration in the positive resist composition is generally from 1 to 10 mass %, preferably from 1 to 8.0 mass %, more preferably from 1.0 to 6.0 mass %.

The positive resist composition of the present invention is used by dissolving the components described above in a predetermined organic solvent, preferably in the above-described mixed solvent, filtering the solution, and coating it on a predetermined support as follows. The filter used for filtering is preferably a filter made of polytetrafluoroethylene, polyethylene or nylon and having a pore size of 0.1 micron or less, more preferably 0.05 microns or less, still more preferably 0.03 microns or less.

For example, the positive resist composition is coated on a substrate (e.g., silicon/silicon dioxide-coated substrate) as used in the production of a precision integrated circuit device, by an appropriate coating method such as spinner or coater, and then dried to form a photosensitive film. Incidentally, a known antireflection film may be previously provided by coating.

The photosensitive film is irradiated with actinic rays or radiation through a predetermined mask, preferably baked (heated), then developed and rinsed, whereby a good resist pattern can be obtained.

Examples of the actinic rays or radiation include infrared light, visible light, ultraviolet light, far ultraviolet light, X-ray and electron beam, but the radiation is preferably far ultraviolet light at a wavelength of 250 nm or less, more preferably 220 nm or less, still more preferably from 1 to 200 nm. Specific examples thereof include KrF excimer laser light (248 nm), ArF excimer laser light (193 nm), $F_2$ excimer laser light (157 nm), X-ray and electron beam. ArF excimer laser light, $F_2$ excimer laser light, EUV (13 nm) and electron beam are preferred.

Before forming the resist film, an antireflection film may be previously provided by coating on the substrate.

The antireflection film used may be either an inorganic film type such as titanium, titanium dioxide, titanium nitride, chromium oxide, carbon and amorphous silicon, or an organic film type comprising a light absorbent and a polymer material. Also, the organic antireflection film may be a commercially available organic antireflection film such as DUV30 Series and DUV-40 Series produced by Brewer Science, Inc., and AR-2, AR-3 and AR-5 produced by Shipley Co., Ltd.

In the development step, an alkali developer is used as follows. The alkali developer which can be used for the resist composition is an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimetylethanolamine and triethanolamine, quaternary ammonium salts such as tetramethylammonium hydroxide and tetraethylammonium hydroxide, and cyclic amines such as pyrrole and piperidine.

Furthermore, this alkali developer may be used after adding thereto alcohols and a surfactant each in an appropriate amount.

The alkali concentration of the alkali developer is usually from 0.1 to 20 mass %.

The pH of the alkali developer is usually from 10.0 to 15.0.

Also, the above-described alkaline aqueous solution may be used after adding thereto alcohols and a surfactant each in an appropriate amount.

As for the rinsing solution, pure water is used, and the pure water may be used after adding thereto a surfactant in an appropriate amount.

After the development or rinsing, the developer or rinsing solution adhering on the pattern may removed by a supercritical fluid.

The development or rinsing treatment may be performed by forming a puddle or may be performed by a puddleless process.

In the case of immersion exposure, a rinsing step may be provided before and after the exposure.

The exposure may be performed by filling a liquid (immersion medium) having a refractive index higher than that of air between the resist film and a lens at the irradiation with actinic rays or radiation (immersion exposure). By this exposure, the resolution can be enhanced. The immersion medium used may be any liquid as long as it has a refractive index higher than that of air, but pure water is preferred. Also, in order to prevent the immersion medium and the photosensitive film from coming into direct contact at the immersion exposure, an overcoat layer may be further provided on the photosensitive film. In this case, the composition can be restrained from dissolving out into the immersion medium from the photosensitive film and the development defects can be reduced.

The immersion liquid used in the immersion exposure is described below.

The immersion liquid is preferably a liquid transparent to light at the exposure wavelength and having a small temperature coefficient of refractive index as much as possible so as to minimize the distortion of an optical image projected on the resist. Particularly, when the exposure light source is an ArF excimer laser (wavelength: 193 nm), water is preferably used in view of easy availability and easy handleability, in addition to the above-described aspects.

Furthermore, a medium having a refractive index of 1.5 or more can also be used because the refractive index can be more enhanced. This medium may be either an aqueous solution or an organic solvent.

In the case of using water as the immersion liquid, for the purpose of decreasing the surface tension of water and increasing the surface activity, an additive (liquid) which does not dissolve the resist layer on a wafer and at the same time, gives only a negligible effect on the optical coat at the undersurface of the lens element, may be added in a small ratio. The additive is preferably an aliphatic alcohol having a refractive index nearly equal to that of water, and specific examples thereof include methyl alcohol, ethyl alcohol and isopropyl alcohol. By adding an alcohol having a refractive index nearly equal to that of water, even when the alcohol component in water is evaporated and its content concentration is changed, the change in the refractive index of the entire liquid can be advantageously made very small. On the other hand, if a substance opaque to light at 193 nm or an impurity greatly differing in the refractive index from water is mingled, this incurs distortion of the optical image projected on the resist. Therefore, the water used is preferably distilled water. Pure water after further filtration through an ion exchange filter or the like may also be used.

The electrical resistance of water is preferably 18.3 MΩcm or more, and TOC (organic material concentration) is preferably 20 ppb or less. Also, the water is preferably subjected to a deaeration treatment.

The lithography performance can be enhanced by increasing the refractive index of the immersion liquid. From such an aspect, an additive for increasing the refractive index may be added to water, or heavy water ($D_2O$) may be used in place of water.

When the positive resist composition of the present invention is applied, the resin (C) contained in the resist is unevenly distributed to the surface and therefore, the contact angle (particularly receding contact angle) on the film surface can be enhanced. When formed as a resist film, the receding contact angle of water for the resist film is preferably 65° or more, more preferably 70° or more. The receding contact angle of a film formed by dissolving only the resin (C) in a solvent and coating the solution is preferably from 70 to 110°. The receding contact angle of the resist film is adjusted to 60 to 80° by controlling the amount of the resin (C) added.

The receding contact angle here is a receding contact angle at ordinary temperature and atmospheric pressure. The receding contact angle is a contact angle on the receding end of a liquid droplet when the liquid droplet starts sliding down after the resist film is inclined.

In order to prevent the resist film from directly contacting with the immersion liquid, an immersion liquid sparingly soluble film (hereinafter, sometimes referred to as a "topcoat") may be provided between the immersion liquid and the resist film formed of the positive resist composition of the present invention. The functions required of the topcoat are suitability for coating on the resist upper layer part, transparency to radiation particularly at 193 nm, and low solubility in the immersion liquid. It is preferred that the topcoat does not intermix with the resist and can be uniformly coated on the resist upper layer.

In view of transparency to light at 193 nm, the topcoat preferably comprises an aromatic-free polymer, and specific examples thereof include a hydrocarbon polymer, an acrylic acid ester polymer, a polymethacrylic acid, a polyacrylic acid, a polyvinyl ether, a silicon-containing polymer and a fluorine-containing polymer. If impurities dissolve out into the immersion liquid from the topcoat, the optical lens is contaminated. In this viewpoint, the residual monomer components of the polymer are preferably less contained in the topcoat.

On peeling off the topcoat, a developer may be used or a releasing agent may be separately used. The releasing agent is preferably a solvent less permeating into the resist. From the standpoint that the peeling step can be performed simultaneously with the resist development step, the topcoat is preferably peelable with an alkali developer and in the light of peeling with an alkali developer, the topcoat is preferably acidic, but in view of non-intermixing with the resist, the topcoat may be neutral or alkaline.

With no difference in the refractive index between the topcoat and the immersion liquid, the resolving power is enhanced. At the exposure with an ArF excimer laser (wavelength: 193 nm), when water is used as the immersion liquid, the topcoat for ArF immersion exposure preferably has a refractive index close to the refractive index of the immersion liquid. From the standpoint of approximating the refractive index to that of the immersion liquid, the topcoat preferably contains a fluorine atom. Also, in view of transparency and refractive index, the topcoat is preferably a thin film.

The topcoat is preferably free of intermixing with the resist and further with the immersion liquid. From this standpoint, when the immersion liquid is water, the topcoat solvent is preferably a medium which is sparingly soluble in the resist solvent and insoluble in water. Furthermore, when the immersion liquid is an organic solvent, the topcoat may be either water-soluble or water-insoluble.

EXAMPLES

The present invention is described in greater detail below by referring to Examples, but the present invention should not be construed as being limited thereto.

Synthesis Example 1 Synthesis of Resin (1)

In a nitrogen stream, 8.6 g of cyclohexanone was charged into a three-neck flask and heated at 80° C. Thereto, a solution obtained by dissolving 9.8 g of 2-adamantyl-isopropyl methacrylate, 4.4 g of dihydroxyadamantyl methacrylate, 8.9 g of norbornane lactone methacrylate, and polymerization initiator V-601 (produced by Wako Pure Chemical Industries, Ltd.) in a concentration of 8 mol % based on the monomers, in 79 g of cyclohexanone was added dropwise over 6 hours. After the completion of dropwise addition, the reaction was further allowed to proceed at 80° C. for 2 hours. The resulting reaction solution was left standing to cool and then, added dropwise to a mixed solution of 800 m of hexane/200 ml of ethyl acetate over 20 minutes, and the powder precipitated was collected by filtration and dried, as a result, 19 g of Resin (1) was obtained. The weight average molecular weight of the obtained resin was 8,800 as calculated in terms of the standard polystyrene and the dispersity (Mw/Mn) was 1.9.

The structures of the acid-decomposable resin (A) used in Examples are shown below. Also, the molar ratio of repeating units (from the left in the structural formula), the weight average molecular weight and the dispersity in each resin are shown in Tables 1 to 4 below.

Resin (19) was synthesized according to Example 2 of JP-A-2004-124082.

Resin (22) was synthesized according to Example of JP-A-2005-331918.

Resin (23) was synthesized according to Example 1 of JP-A-2004-175981.

Resin (25) was synthesized according to Example 1 of JP-A-2005-156726.

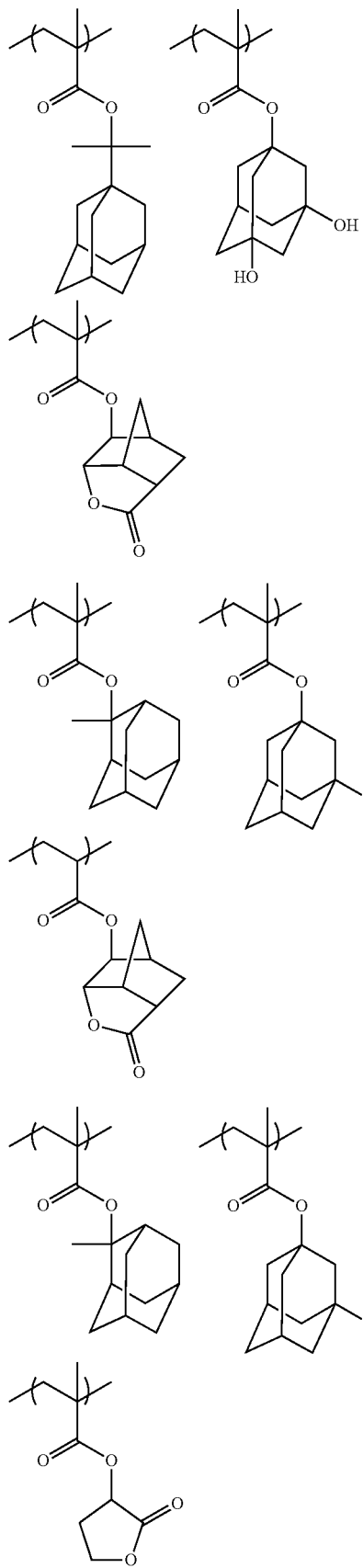
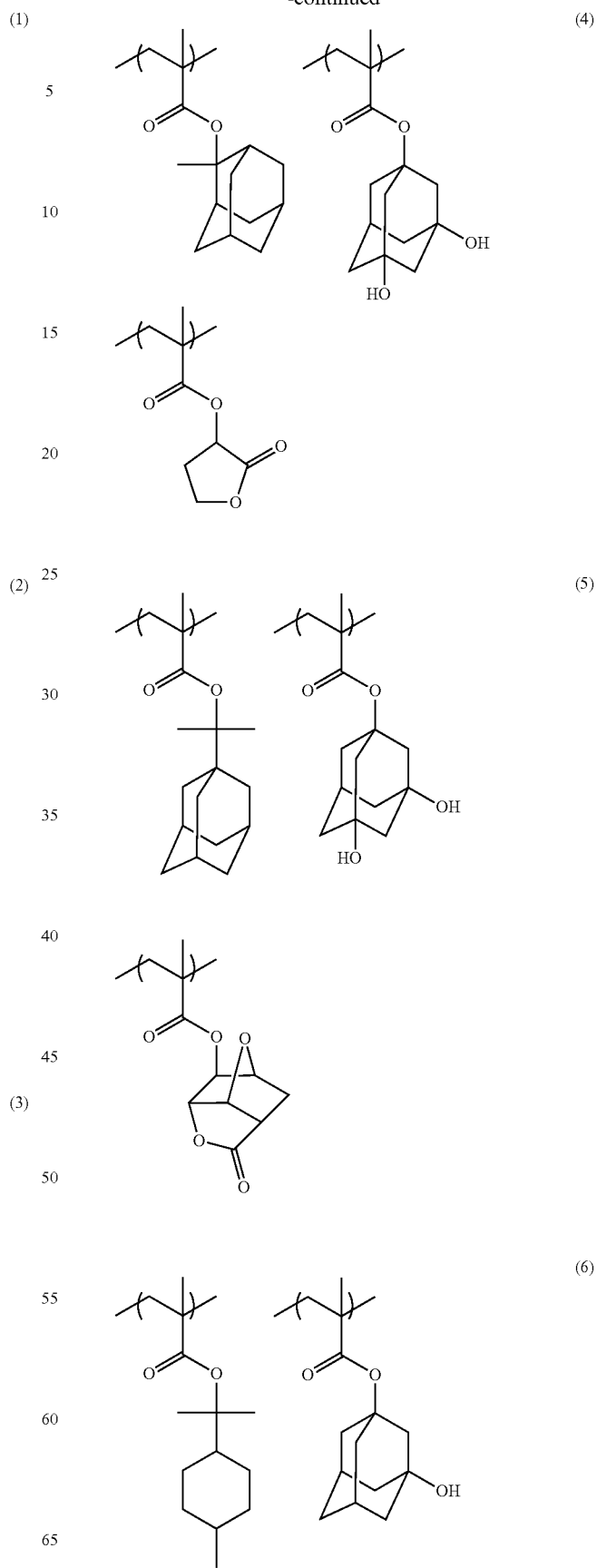

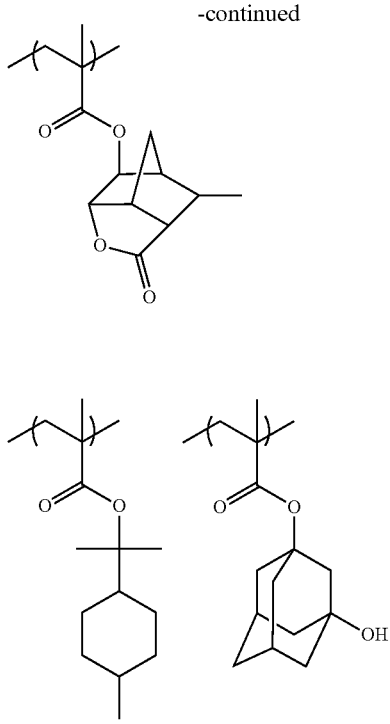
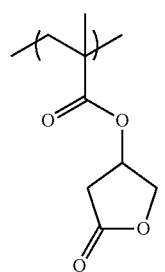
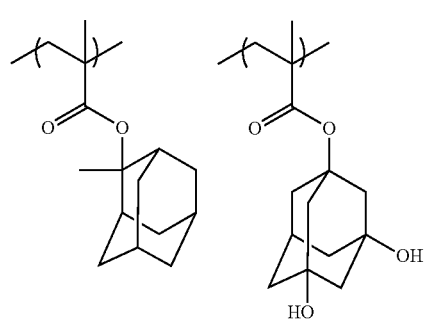
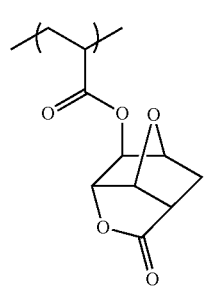
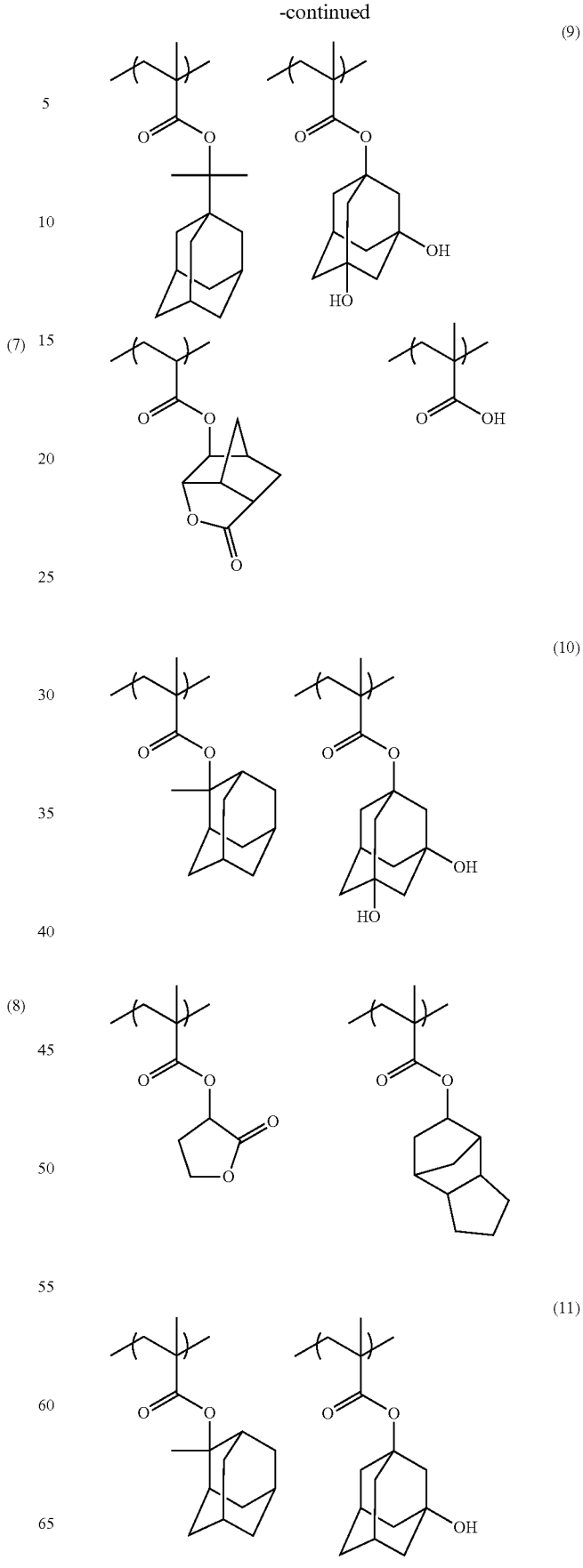

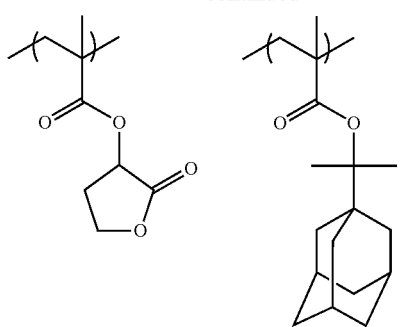
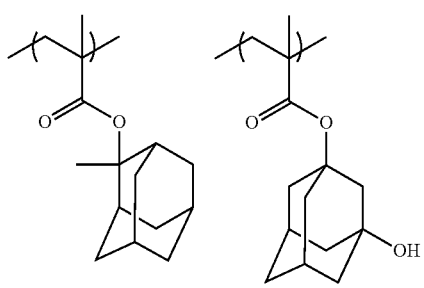
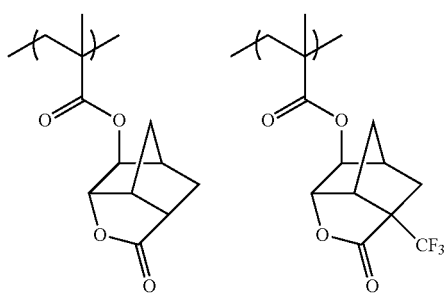
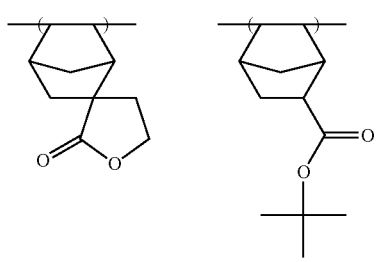
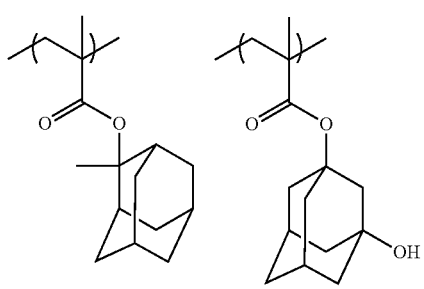
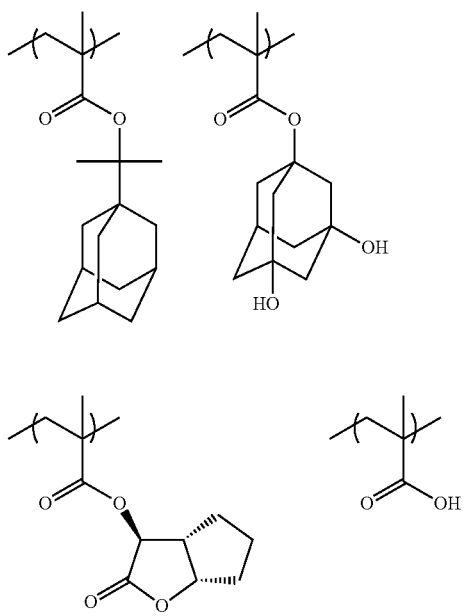
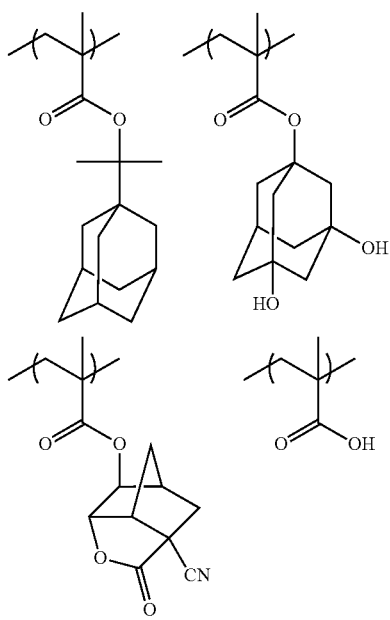

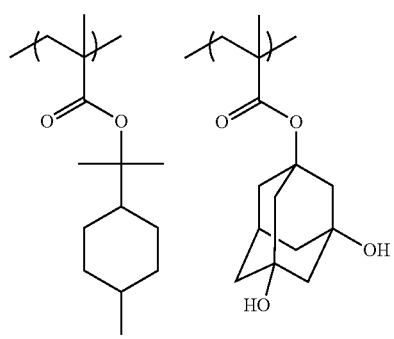
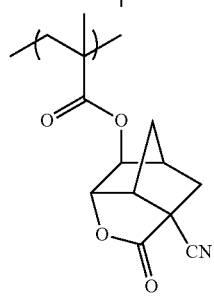
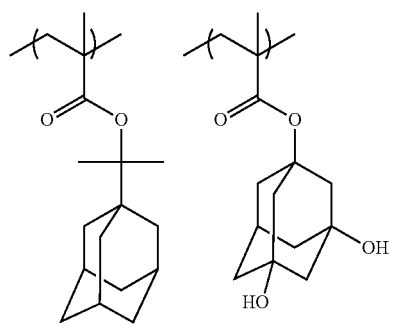
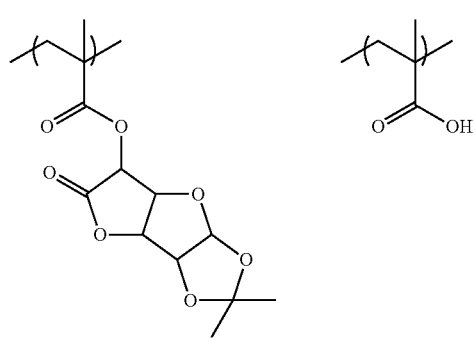
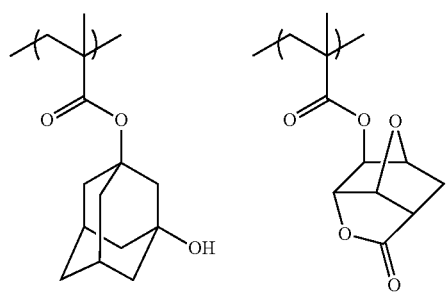
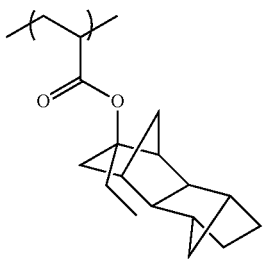
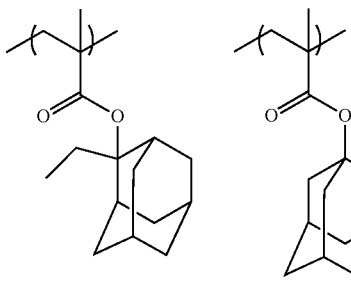
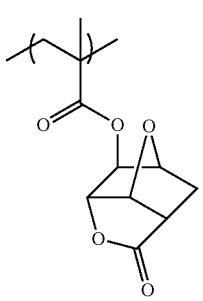
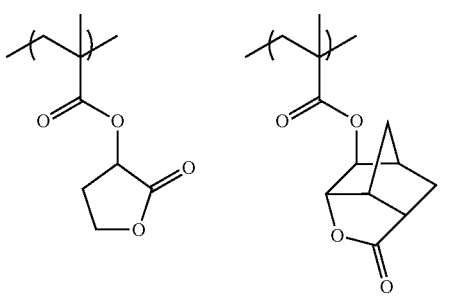

(22)
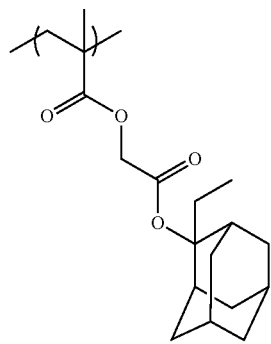
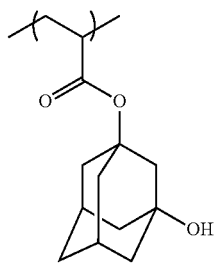
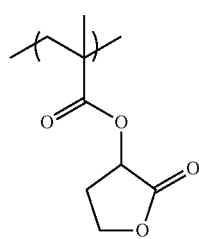
(23)
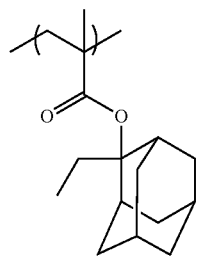
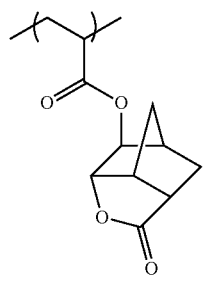
(24)
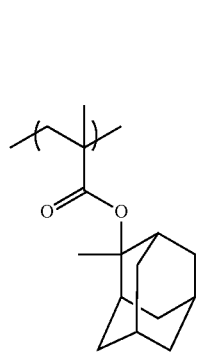
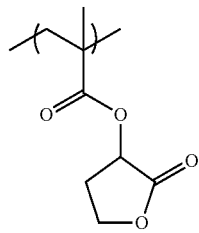
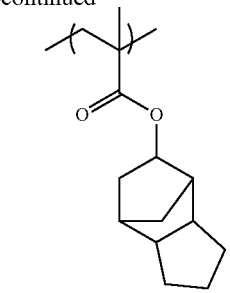
(25)
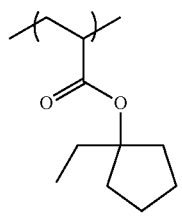
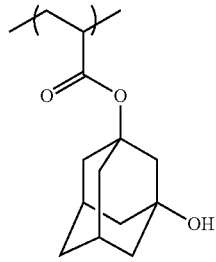
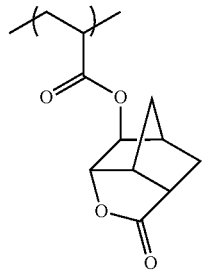
(26)
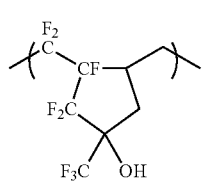
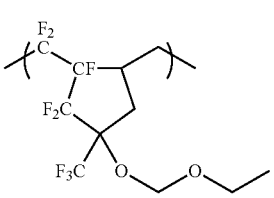
(27)
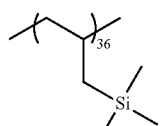
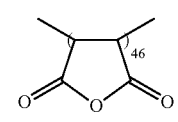
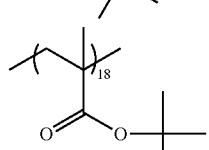
(28)
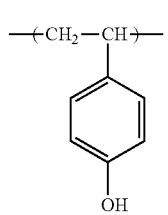
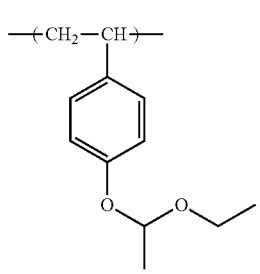

TABLE 1

| Resin | Composition (molar ratio) | Mw | Mw/Mn |
|---|---|---|---|
| 1 | 50/10/40 | 8800 | 1.9 |
| 2 | 40/22/38 | 12000 | 2.0 |
| 3 | 34/33/33 | 11000 | 2.3 |
| 4 | 45/15/40 | 10500 | 2.1 |
| 5 | 30/25/45 | 8400 | 2.3 |
| 6 | 39/20/41 | 10500 | 2.1 |
| 7 | 49/10/41 | 9500 | 2.5 |
| 8 | 35/32/33 | 14000 | 2.6 |
| 9 | 40/20/35/5 | 12500 | 2.4 |
| 10 | 40/15/40/5 | 10000 | 1.8 |
| 11 | 40/15/40/5 | 9800 | 2.3 |
| 12 | 35/20/40/5 | 6100 | 2.3 |
| 13 | 50/50 | 5200 | 2.1 |
| 14 | 30/30/30/10 | 8600 | 2.5 |
| 15 | 40/20/35/5 | 12000 | 2.1 |

TABLE 2

| Resin | Composition (molar ratio) | Mw | Mw/Mn |
|---|---|---|---|
| 16 | 30/20/40/10 | 8000 | 2.0 |
| 17 | 40/10/50 | 6000 | 1.8 |
| 18 | 30/20/40/10 | 8500 | 1.5 |

TABLE 3

| Resin | Composition (molar ratio) | Mw | Mw/Mn |
|---|---|---|---|
| 19 | 35/30/35 | 9800 | 1.8 |
| 20 | 30/40/30 | 9500 | 1.9 |
| 21 | 25/25/50 | 6700 | 2.0 |
| 22 | 50/25/25 | 12000 | 2.0 |
| 23 | 50/30/20 | 10000 | 2.0 |
| 24 | 40/20/20/10 | 6400 | 2.1 |
| 25 | 40/10/50 | 7700 | 2.0 |

TABLE 4

| Resin | Composition (molar ratio) | Mw | Mw/Mn |
|---|---|---|---|
| 26 | 70/30 | 8000 | 1.8 |
| 27 | 36/46/18 | 8500 | 1.8 |
| 28 | 70/30 | 8000 | 1.8 |

Synthesis Example 2 Synthesis of Compound (A)

In 1 L-volume three-neck flask, 23.2 g of 2,4-dimethyl-3-pentanol, 33.3 mL of triethylamine and 400 mL of tetrahydrofuran were adjusted and ice-cooled. To this solution, a solution obtained by dissolving 38 g of 2-trifluoromethyl-acrylic acid chloride in 200 mL of tetrahydrofuran was added dropwise over 1 hour. The resulting solution was stirred for 1 hour and after the completion of reaction, the reaction solution was neutralized with 2 mol/L of dilute hydrochloric acid and extracted twice with ethyl acetate. The oil layer was washed with a saturated aqueous sodium hydrogencarbonate solution and pure water. Furthermore, the oil layer was dried over sodium sulfate, concentrated and then subjected to separation through a silica gel column (hexane:ethyl acetate=9:1) to obtain 30 g of the objective Compound (A) shown below.

$^1$H-NMR (400 MHz, CDCl3) δ 0.91 (td, 12H), 1.98 (m, 2H), 4.76 (t, 1H), 6.31 (s, 1H), 6.73 (s, 1H)

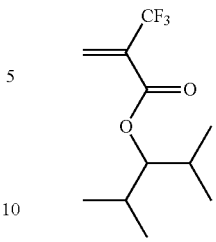

Compound A

Synthesis Example 3 Synthesis of Resin (C-1)

Heptafluorobutyl methacrylate and tert-butyl methacrylate were charged at a ratio of 50/50 (by mol) and dissolved in cyclohexanone to prepare 450 g of a solution having a solid content concentration of 22%. To this solution, 50 mol % of polymerization initiator V-601 produced by Wako Pure Chemical Industries, Ltd. was added. The resulting solution was added dropwise to 50 mL of cyclohexanone heated at 80° C., over 2 hours in a nitrogen atmosphere. After the completion of dropwise addition, the reaction solution was stirred for 2 hours to obtain Reaction Solution (C-1). After the completion of reaction, Reaction Solution (C-1) was cooled to room temperature and crystallized from a 10-fold amount of methanol, the precipitated white powder was collected by filtration, and the objective Resin (C-1) was recovered.

The polymer compositional ratio determined from $^1$H-NMR was 50/50 (by mol). Also, the weight average molecular weight determined by the GPC measurement and calculated in terms of standard polystyrene was 8,800, and the dispersity was 2.1.

Synthesis Example 4 Synthesis of Resin (C-2)

A 1,1,2-trichloro-trifluoroethylene 150 ml solution containing 25 g (0.20 mol) of trifluoroethyl vinyl ether was charged in a 1 L-volume autoclave, and the system was pressurized to 200 psi in a nitrogen atmosphere. Furthermore, 20 g (0.20 mol) of tetrafluoroethylene was poured thereinto, and the mixture was heated at 50° C. under stirring. In this reaction solution, a 1,1,2-trichloro-trifluoroethylene 15 ml solution containing 1.2 g of di(4-tert-butylcyclohexyl)peroxydicarbonate was poured over 20 minutes, and the stirring was further continued for 20 hours. After the completion of reaction, the reaction solution was charged into 2 L of methanol while vigorously stirring to precipitate a colorless transparent resin.

The obtained resin was measured by gel permeation chromatography (GPC) and found to have a weight average molecular weight of 5,200 and a dispersity of 1.8. Also, the polymer compositional ratio determined from 19F-NMR was 50/50.

Synthesis Example 5 Synthesis of Resin (C-3)

0.05 Mol of heptafluorobutyl 2-trifluoromethylmethacrylate and 0.05 mol of norbornene were mixed. To this mixture kept under stirring at 80° C. in a nitrogen atmosphere, 1.5 mol % of polymerization initiator V-59 produced by Wako Pure Chemical Industries, Ltd. was added. The stirring was continued for 3 hours. Thereafter, the solution was stirred for 12 hours while adding 1.5 mol % of polymerization initiator V-59 every 3 hours. After the completion of reaction, the reaction solution was dissolved in 20 mL of THF. The resulting solution was cooled to room temperature and crystallized from 800 mL of methanol, and the precipitated white powder was collected by filtration to recover the objective Resin (C-3).

The polymer compositional ratio determined from ¹HNMR was 50/50 (from the left in the structural formula). Also, the weight average molecular weight determined by the GPC measurement and calculated in terms of standard polystyrene was 4,800, and the dispersity was 1.9.

Synthesis Example 6 Synthesis of Resin (C-6)

4-(1,1,1,3,3,3-Hexafluoro-2-hydroxypropan-2-yl)styrene (50 g) was dissolved in 200 mL of cyclohexanone. To this solution kept under stirring at 80° C. in a nitrogen atmosphere, 5 mol % of polymerization initiator V-601 produced by Wako Pure Chemical Industries, Ltd. was added. The resulting solution was stirred for 5 hours. After the completion of reaction, the reaction solution was cooled to room temperature and crystallized from a 5-fold amount of hexane, and the precipitated white powder was collected by filtration to recover the objective resin (C-6).

The weight average molecular weight determined by the GPC measurement and calculated in terms of standard polystyrene was 12,000, and the dispersity was 2.0.

Synthesis Example 7 Synthesis of Resin (C-7)

Equimolar amounts of allyltrimethylsilane and maleic anhydride were dissolved in tetrahydrofuran to prepare 450 g of a solution having a solid content concentration of 50 mass %. To this mixture kept under stirring at 65° C. in a nitrogen atmosphere, 0.17 mol % of polymerization initiator V-65 produced by Wako Pure Chemical Industries, Ltd. was added. The stirring was continued for 5 hours. After the completion of reaction, 100 mL of tetrahydrofuran was added to the reaction solution and dissolved. The resulting solution was then cooled to room temperature and crystallized from 800 mL of hexane, and the precipitated white powder was collected by filtration to recover the objective Resin (C-7).

The polymer compositional ratio determined from ¹HNMR was 50/50 (from the left in the structural formula). Also, the weight average molecular weight determined by the GPC measurement and calculated in terms of standard polystyrene was 5,800, and the dispersity was 1.9.

Resin (C-4) was synthesized in the same manner as in Synthesis Example 4.

Resins (C-5) and (C-10) were synthesized in the same manner as in Synthesis Example 5.

Resins (C-8), (C-30), (C-36) to (C-38), (C-40) and (C-42) were synthesized in the same manner as in Synthesis Example 7 except for performing the crystallization from a methanol solvent.

Resins (C-9) and (C-22) were synthesized in the same manner as in Synthesis Example 6 except for performing the crystallization from a methanol solvent.

Resins (C-11) to (C-20), (C-23) to (C-29), (C-31) to (C-35), (C-39), (C-41), (C-43), (C-44) and (C-45) were synthesized in the same manner as in Synthesis Example 3.

Resin (C-21) was synthesized in the same manner as in Synthesis Example 6.

Resin (C-46) was synthesized in the same manner as in Synthesis Example 7.

Structures of Resins (C-1) to (C-44) are shown below. Also, the molar ratio of repeating units (repeating units from the left), weight average molecular weight, dispersity, shape and glass transition temperature in each resin are shown in Tables 5 to 8 below.

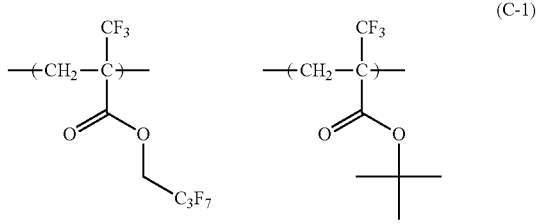
(C-1)

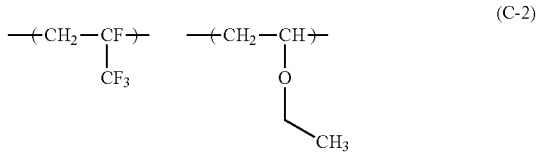
(C-2)

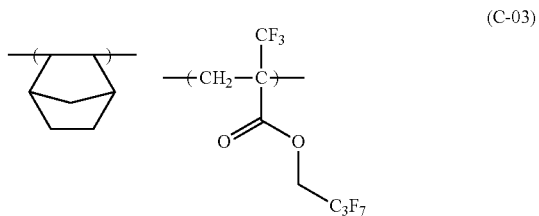
(C-03)

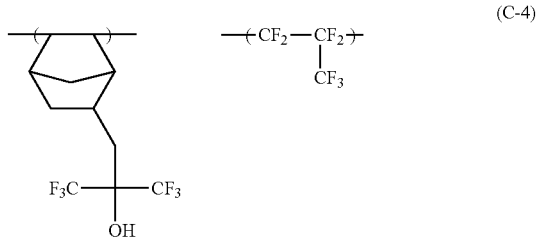
(C-4)

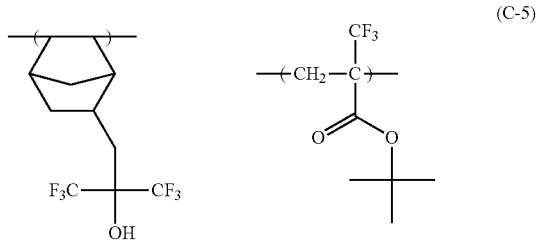
(C-5)

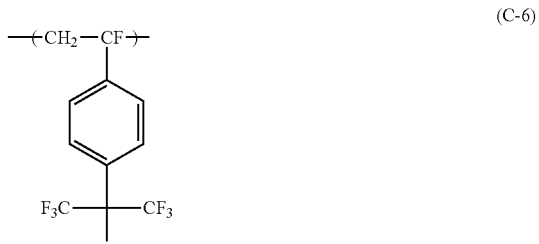
(C-6)

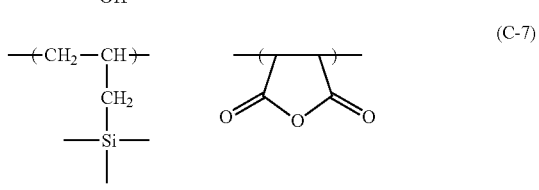
(C-7)

-continued
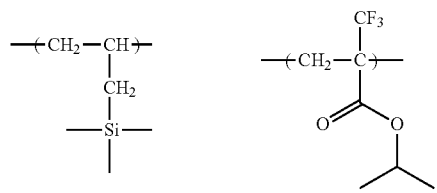 (C-8)
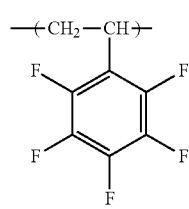 (C-9)
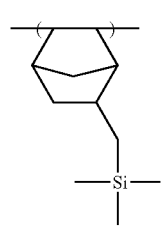 (C-10) 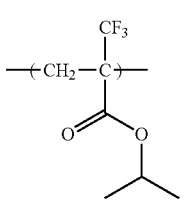
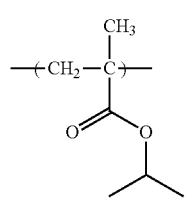 (C-11) 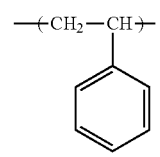
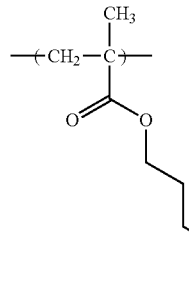 (C-12) 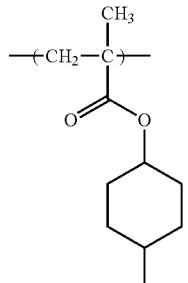
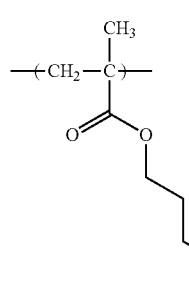 (C-13) 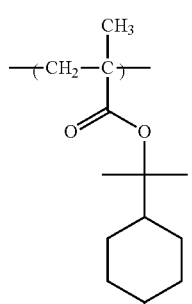
-continued
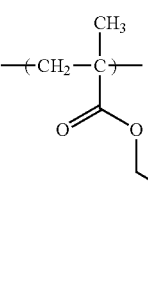 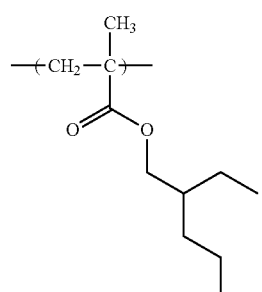 (C-14)
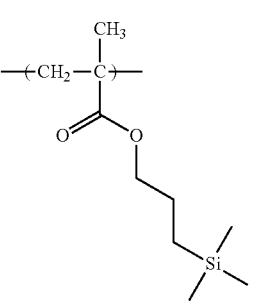 (C-15)
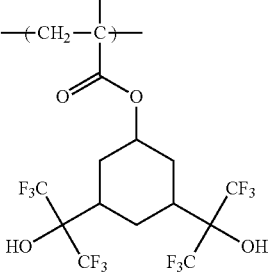
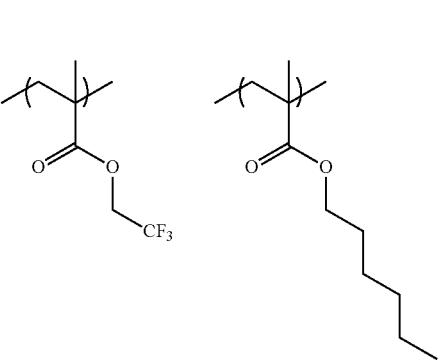 (C-16)
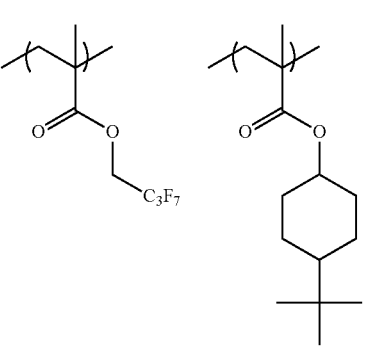 (C-17)

(C-18) 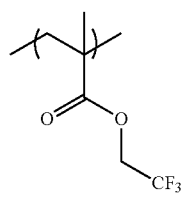 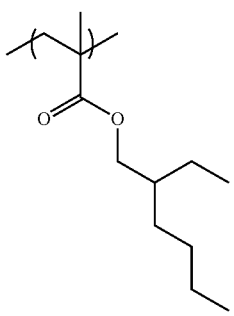
(C-19) 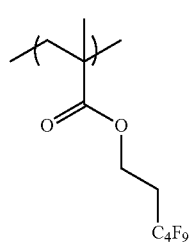 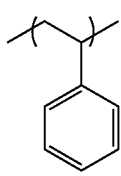
(C-20) 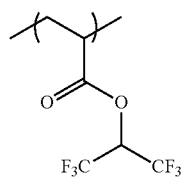
(C-21) 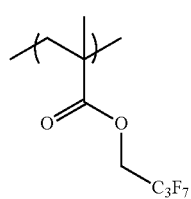
(C-22) 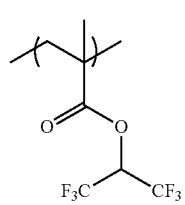
(C-23) 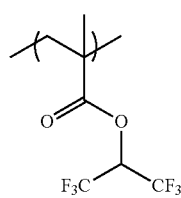 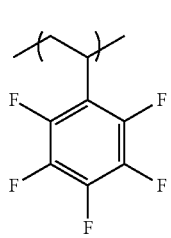
(C-24) 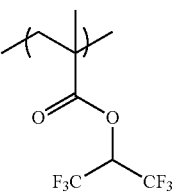 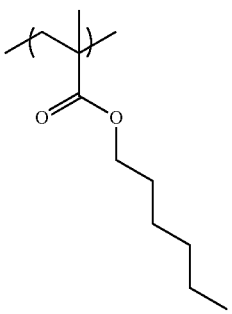
(C-25) 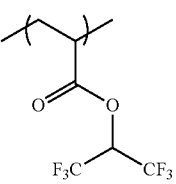 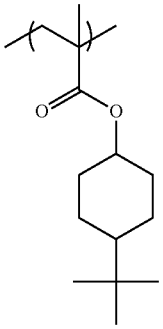
(C-26) 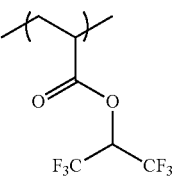 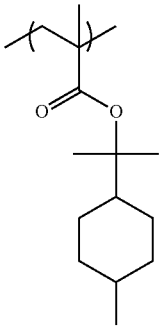
(C-27) 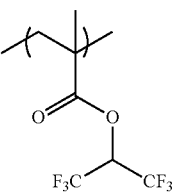 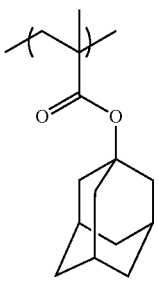
(C-28) 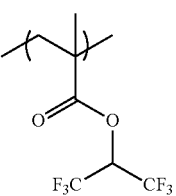 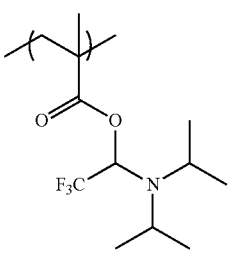

-continued
(C-29) 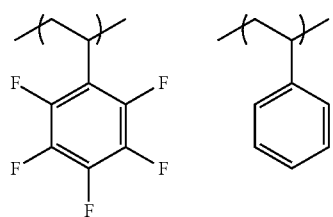
(C-30) 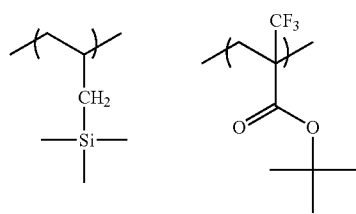
(C-31) 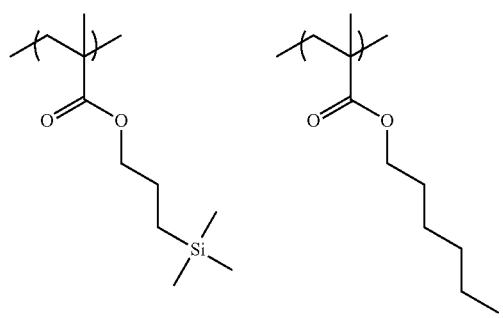
(C-32) 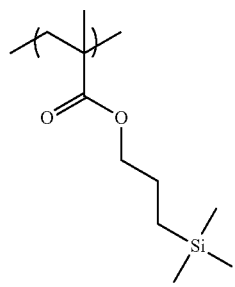
(C-33) 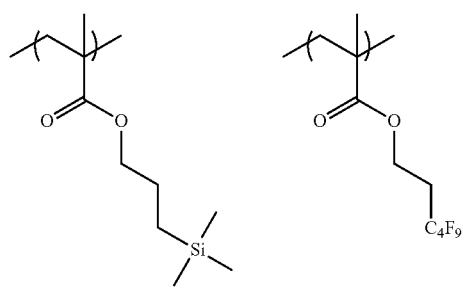
(C-34) 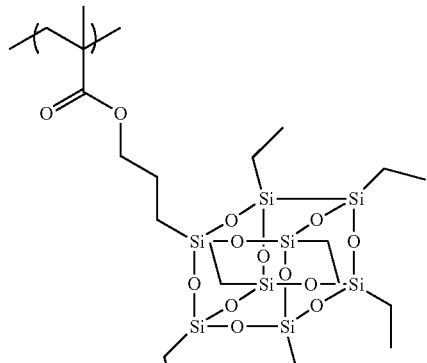
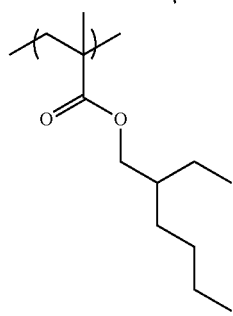
(C-35) 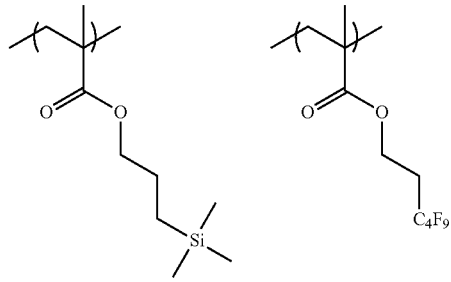
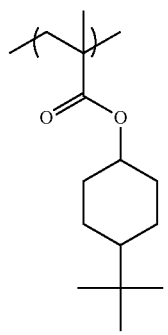
(C-36) 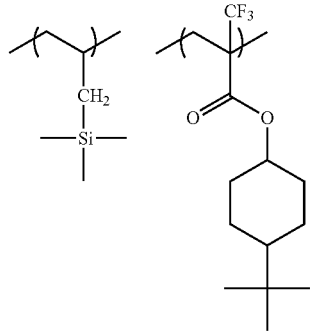

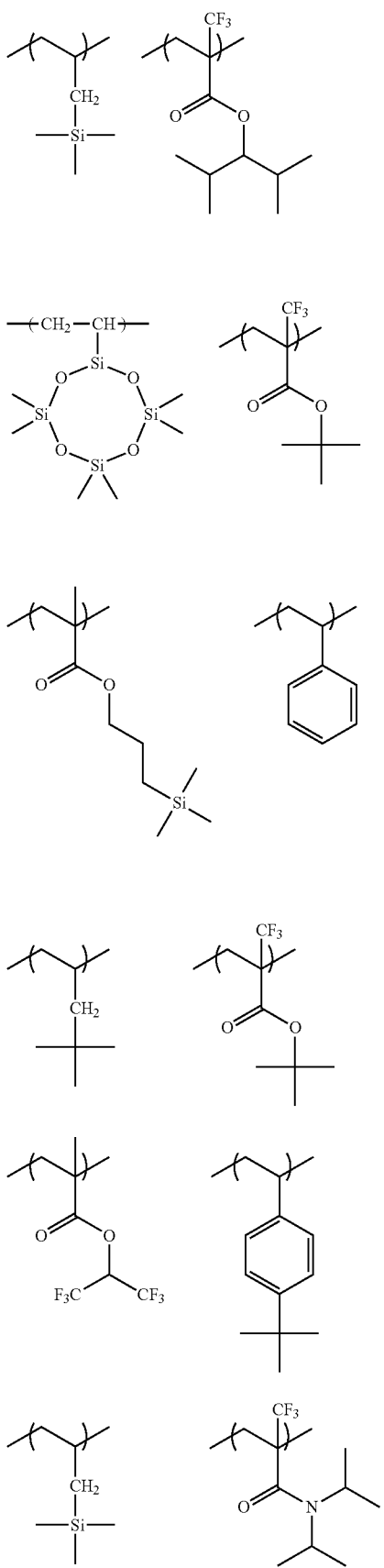
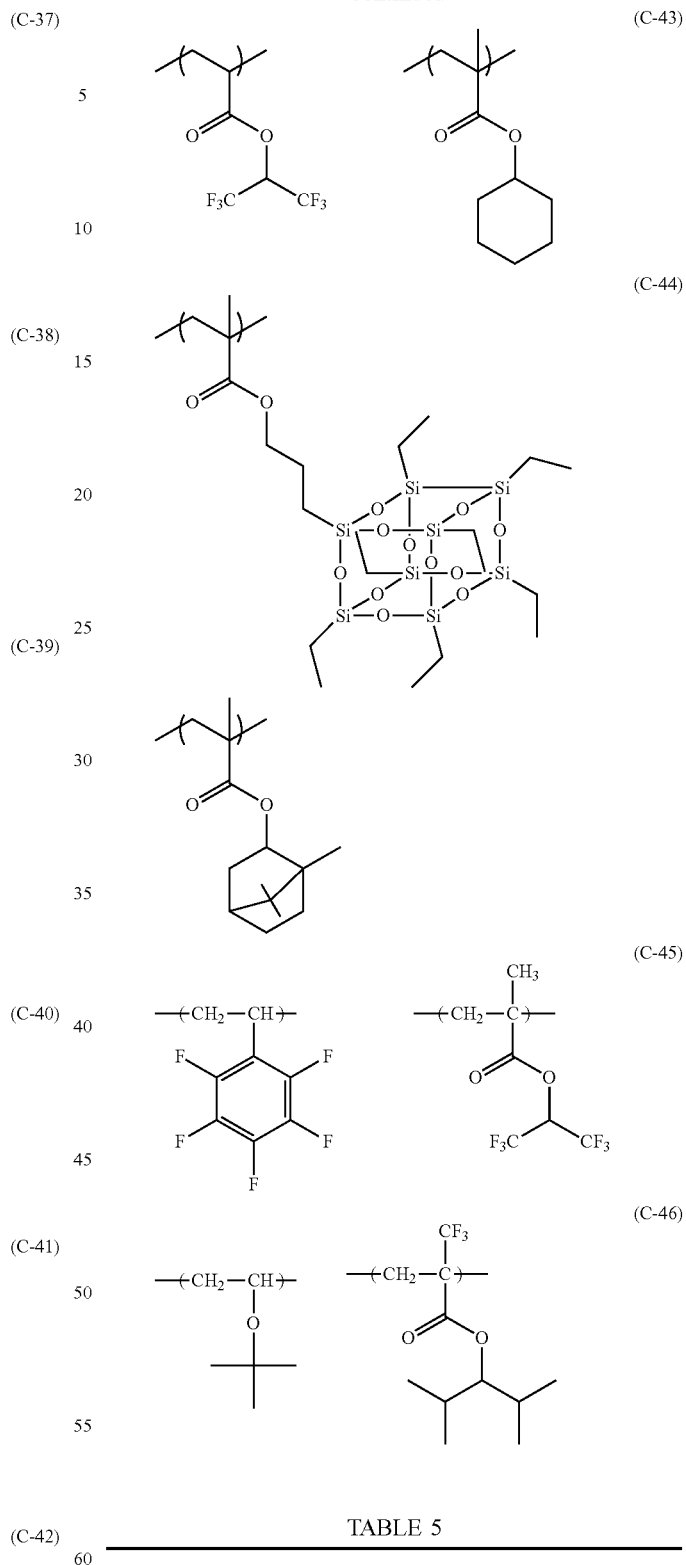
TABLE 5
| Resin | Composition (molar ratio) | Mw | Mw/Mn | Shape | Tg |
|---|---|---|---|---|---|
| C-1 | 50/50 | 8800 | 2.1 | solid | 60 |
| C-2 | 50/50 | 5200 | 1.8 | liquid | <25 |
| C-3 | 50/50 | 4800 | 1.9 | solid | 150 |
| C-4 | 50/50 | 5300 | 1.9 | solid | 100 |
| C-5 | 50/50 | 6200 | 1.9 | solid | >160 |

TABLE 5-continued

| Resin | Composition (molar ratio) | Mw | Mw/Mn | Shape | Tg |
|---|---|---|---|---|---|
| C-6 | 100 | 12000 | 2.0 | solid | 100 |
| C-7 | 50/50 | 5800 | 1.9 | solid | 100 |
| C-8 | 50/50 | 6300 | 1.9 | solid | 80 |
| C-9 | 100 | 5500 | 2.0 | solid | 80 |
| C-10 | 50/50 | 7500 | 1.9 | solid | >160 |
| C-11 | 70/30 | 10200 | 2.2 | solid | 80 |
| C-12 | 40/60 | 15000 | 2.2 | solid | 130 |
| C-13 | 40/60 | 13000 | 2.2 | solid | 130 |
| C-14 | 80/20 | 11000 | 2.2 | liquid | <25 |
| C-15 | 60/40 | 9800 | 2.2 | solid | 90 |

TABLE 6

| Resin | Composition (molar ratio) | Mw | Mw/Mn | Shape | Tg |
|---|---|---|---|---|---|
| C-16 | 50/50 | 8000 | 2.2 | liquid | <25 |
| C-17 | 50/50 | 7600 | 2.0 | solid | 70 |
| C-18 | 50/50 | 12000 | 2.0 | liquid | <25 |
| C-19 | 20/80 | 6500 | 1.8 | solid | 45 |
| C-20 | 100 | 4000 | 1.6 | solid | 35 |
| C-21 | 100 | 6000 | 1.6 | liquid | <25 |
| C-22 | 100 | 2000 | 1.6 | solid | 35 |
| C-23 | 50/50 | 6000 | 1.7 | solid | 70 |
| C-24 | 50/50 | 8800 | 1.9 | liquid | <25 |
| C-25 | 50/50 | 7800 | 2.0 | solid | 100 |
| C-26 | 50/50 | 8000 | 2.0 | solid | 100 |
| C-27 | 80/20 | 8000 | 1.8 | solid | 140 |
| C-28 | 30/70 | 7000 | 1.7 | solid | 100 |
| C-29 | 50/50 | 6500 | 1.6 | solid | 100 |
| C-30 | 50/50 | 6500 | 1.6 | solid | 100 |
| C-31 | 50/50 | 9000 | 1.8 | liquid | <25 |
| C-32 | 100 | 10000 | 1.6 | liquid | <25 |
| C-33 | 70/30 | 8000 | 2.0 | liquid | <25 |
| C-34 | 10/90 | 8000 | 1.8 | solid | 100 |
| C-35 | 30/30/40 | 9000 | 2.0 | solid | 80 |
| C-36 | 50/50 | 6000 | 1.4 | solid | 110 |
| C-37 | 50/50 | 5500 | 1.5 | solid | 90 |

TABLE 7

| Resin | Composition (molar ratio) | Mw | Mw/Mn | Shape | Tg |
|---|---|---|---|---|---|
| C-38 | 50/50 | 4800 | 1.8 | solid | 100 |
| C-39 | 60/40 | 5200 | 1.8 | solid | 50 |
| C-40 | 50/50 | 8000 | 1.5 | solid | 100 |
| C-41 | 20/80 | 7500 | 1.8 | solid | 120 |
| C-42 | 50/50 | 6200 | 1.6 | solid | 100 |
| C-43 | 60/40 | 16000 | 1.8 | solid | 80 |
| C-44 | 80/20 | 10200 | 1.8 | solid | 100 |

TABLE 8

| Resin | Composition (molar ratio) | Mw | Mw/Mn | Shape | Tg |
|---|---|---|---|---|---|
| C-45 | 80/20 | 20000 | 2.0 | solid | 110 |
| C-46 | 50/50 | 4500 | 1.2 | solid | 100 |

Examples 1 to 52 and Comparative Examples 1 to 8

<Preparation of Resist>

The components shown in Tables 9 to 12 below were dissolved in a solvent to prepare a solution having a solid content concentration of 6 mass %, and the obtained solution was filtered through a 0.1-μm polyethylene filter to prepare a positive resist solution. The positive resist solutions prepared were evaluated by the following methods, and the results are shown in Tables 9 to 12. As for each component in Tables 9 to 12, when a plurality of species were used, the ratio is a ratio by mass.

[Image Performance Test]
(Exposure Condition (1))

An organic antireflection film, ARC29A (produced by Nissan Chemical Industries, Ltd.), was coated on a silicon wafer and baked at 205° C. for 60 seconds to form a 78-nm antireflection film, and the positive resist solution prepared above was coated thereon and baked at 130° C. for 60 seconds to form a 250-nm resist film. The obtained wafer was subjected to pattern exposure by using an ArF excimer laser scanner (PAS5500/1100, manufactured by ASML, NA: 0.75, σo/σi: 0.85/0.55). Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (2))

This condition is for forming a resist pattern by an immersion exposure method using pure water.

An organic antireflection film, ARC29A (produced by Nissan Chemical Industries, Ltd.), was coated on a silicon wafer and baked at 205° C. for 60 seconds to form a 78-nm antireflection film, and the positive resist solution prepared above was coated thereon and baked at 130° C. for 60 seconds to form a 250-nm resist film. The obtained wafer was subjected to pattern exposure by using an ArF excimer laser immersion scanner (NA: 0.85). The immersion liquid used was ultrapure water. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

[Evaluation of PED]

The resist patterns obtained in (Exposure Condition 1) and (Exposure Condition 2) and resist patterns obtained by allowing to stand for 30 minutes after exposure and then performing the same operation as above were observed through a scanning electron microscope (S-4800, manufactured by Hitachi, Ltd.) to evaluate the pattern collapse performance and the pattern profile.

As for the pattern collapse, an exposure amount of reproducing a 90-nm line-and-space pattern was defined as an optimal exposure amount, and the line width at which a pattern, that is, a dense pattern having a line-and-space ratio of 1:1 or an isolated pattern having a line-and-space ratio of 1:10, is resolved without collapse to a finer mask size than that when exposed with an optimal exposure amount, was defined as a threshold pattern-collapse line width. A smaller value reveals that a finer pattern is resolved without collapse and that pattern collapse is less liable to occur.

[Followability of Water]

The positive resist composition prepared was coated on a silicon wafer and baked at 130° C. for 60 seconds to form a 160-nm resist film. Subsequently, as shown in FIG. 1, pure water 2 was filled between the wafer 1 having coated thereon the positive resist composition and a quartz glass substrate 3.

In this state, the quartz glass substrate 3 was horizontally moved (scan) with respect to the surface of the resist-coated substrate 1, and the pure water 2 following it was observed with an eye. The scan speed of the quartz glass substrate 3 was gradually increased, and the followability of water was evaluated by determining the limit scan speed where a water droplet starts remaining on the receding side due to failure of the pure water 2 in following the scan speed of the quartz glass substrate 3. A larger limit speed allowing for scanning indicates that water can follow a higher scan speed and the followability of water on the resist film is better.

TABLE 9

| | Composition | | | | | |
|---|---|---|---|---|---|---|
| | Resin (2 g) | Photoacid Generator (mg) | Solvent (mass ratio) | Basic Compound (mg) | Resin (C) (wt %) | Surfactant (mg) |
| Example 1 | 1 | z2 (80) | SL-4/SL-2 40/60 | N-5 (7) | C-1 (1.0) | W-1 (3) |
| Example 2 | 1 | z1 (60) | SL-4/SL-2 40/60 | N-5 (7) | C-1 (6.0) | W-1 (3) |
| Example 3 | 1 | z2 (80) | SL-4/SL-2 40/60 | N-3 (6) | C-2 (2.0) | W-1 (3) |
| Example 4 | 2 | z51 (100) | SL-2/SL-4/SL-6 40/59/1 | N-6 (10) | C-3 (1.0) | W-3 (3) |
| Example 5 | 2 | z51 (100) | SL-2/SL-4/SL-6 40/59/1 | N-1 (7) | C-4 (5.0) | W-3 (3) |
| Example 6 | 2 | z9 (100) | SL-2/SL-4/SL-6 40/59/1 | N-2 (9) | C-5 (2.0) | W-3 (3) |
| Example 7 | 3 | z2/z55 (20/100) | SL-2/SL-4 70/30 | N-3 (6) | C-6 (2.0) | W-6 (3) |
| Example 8 | 3 | z2/z15 (40/60) | SL-2/SL-4 70/30 | N-3 (6) | C-7 (0.5) | W-6 (3) |
| Example 9 | 4 | z9 100 | SL-2/SL-4 60/40 | — | C-7 (1.0) | W-1 (5) |
| Example 10 | 5 | z65/z9 (20/80) | SL-3/SL-4 30/70 | N-6 (10) | C-8 (1.5) | W-5 (4) |
| Example 11 | 6 | z44/z65 (25/80) | SL-2/SL-4/SL-5 40/58/2 | N-1 (7) | C-9 (2.0) | W-1 (4) |
| Example 12 | 7 | z55/z47 (30/60) | SL-1/SL-2 60/40 | N-4 (13) | C-10 (1.5) | W-6 (4) |
| Example 13 | 8 | z44/z65 (50/50) | SL-1/SL-2 60/40 | N-3 (6) | C-12 (2.0) | W-2 (3) |
| Example 14 | 9 | z65 100 | SL-2/SL-4/SL-6 40/59/1 | N-2 (9) | C-13 (2.0) | W-3 (3) |
| Example 15 | 10 | z15/z37 (80/50) | SL-2/SL-4/SL-6 40/59/1 | N-6 (10) | C-8 (1.0) | W-4 (5) |
| Example 16 | 11 | z15/z37 (80/50) | SL-2/SL-4 60/40 | N-1 (7) | C-11 (1.0) | — |
| Example 17 | 12 | z55/z65 40/60 | SL-1/SL-2 50/50 | N-3 (6) | C-12 (1.0) | W-1 (3) |
| Example 18 | 13 | z2/z15 (40/60) | SL-2/SL-4/SL-6 40/59/1 | N-6 (10) | C-13 (1.0) | W-4 (5) |
| Example 19 | 14 | z62 (120) | SL-2/SL-4/SL-6 40/59/1 | N-1 (7) | C-14 (0.5) | W-2 (5) |
| Example 20 | 15 | z44 (80) | SL-1/SL-2 60/40 | N-1 (7) | C-15 (1.5) | W-1 (3) |

| | Evaluation Results | | | | | | | |
|---|---|---|---|---|---|---|---|---|
| | Normal Exposure | | | | Immersion Exposure | | | |
| | Normal Exposure | | When Allowed to Stand for 30 Minutes after Exposure | | Normal Immersion Exposure | | When Allowed to Stand for 30 Minutes after Exposure | | Followability of Water |
| | Profile | Collapse | Profile | Collapse | Profile | Collapse | Profile | Collapse | (mm/sec) |
| Example 1 | rectangular | 71 | rectangular | 71 | rectangular | 71 | rectangular | 71 | 200 |
| Example 2 | rectangular | 71 | rectangular | 73 | rectangular | 71 | rectangular | 73 | 200 |
| Example 3 | rectangular | 70 | rectangular | 72 | rectangular | 70 | rectangular | 74 | 200 |
| Example 4 | rectangular | 70 | rectangular | 70 | rectangular | 70 | rectangular | 70 | 250 |
| Example 5 | rectangular | 71 | rectangular | 71 | rectangular | 71 | rectangular | 71 | 150 |
| Example 6 | rectangular | 71 | rectangular | 71 | rectangular | 71 | rectangular | 71 | 150 |
| Example 7 | rectangular | 71 | rectangular | 71 | rectangular | 71 | rectangular | 71 | 150 |
| Example 8 | rectangular | 71 | rectangular | 71 | rectangular | 71 | rectangular | 71 | 150 |
| Example 9 | rectangular | 71 | rectangular | 71 | rectangular | 71 | rectangular | 73 | 150 |
| Example 10 | rectangular | 70 | rectangular | 70 | rectangular | 70 | rectangular | 70 | 250 |
| Example 11 | rectangular | 70 | rectangular | 70 | rectangular | 70 | rectangular | 71 | 250 |
| Example 12 | rectangular | 70 | rectangular | 70 | rectangular | 70 | rectangular | 70 | 250 |
| Example 13 | rectangular | 70 | rectangular | 70 | rectangular | 70 | rectangular | 70 | 250 |
| Example 14 | rectangular | 71 | rectangular | 71 | rectangular | 71 | rectangular | 71 | 200 |
| Example 15 | rectangular | 70 | rectangular | 70 | rectangular | 70 | rectangular | 70 | 250 |
| Example 16 | rectangular | 70 | rectangular | 70 | rectangular | 70 | rectangular | 73 | 250 |
| Example 17 | rectangular | 70 | rectangular | 70 | rectangular | 70 | rectangular | 73 | 250 |
| Example 18 | rectangular | 71 | rectangular | 71 | rectangular | 71 | rectangular | 73 | 200 |
| Example 19 | rectangular | 70 | rectangular | 72 | rectangular | 70 | rectangular | 74 | 200 |
| Example 20 | rectangular | 71 | rectangular | 71 | rectangular | 71 | rectangular | 73 | 150 |

TABLE 10

| | Composition | | | | | |
|---|---|---|---|---|---|---|
| | Resin (2 g) | Photoacid Generator (mg) | Solvent (mass ratio) | Basic Compound (mg) | Resin (C) (wt %) | Surfactant (mg) |
| Example 21 | 3 | z4 (65) | SL-2/SL-4 60/40 | N-1 (7) | C-16 (3.0) | W-1 (2) |
| Example 22 | 2 | z5 (70) | SL-1/SL-2 40/60 | N-1 (7) | C-17 (1.0) | W-1 (3) |
| Example 23 | 15 | z59 (90) | SL-1/SL-2 60/40 | N-1 (7) | C-18 (2.0) | W-4 (3) |
| Example 24 | 17 | z68 (120) | SL-1/SL-2 40/60 | N-1 (7) | C-19 (1.0) | W-1 (3) |
| Example 25 | 17 | z55/z23 (100/25) | SL-2/SL-4 60/40 | N-5/N-1 (7/7) | C-20 (2.0) | W-4 (2) |
| Example 26 | 18 | z55/z65 (75/75) | SL-2/SL-4 60/40 | N-5/N-1 (7/7) | C-21 (5.0) | W-4 (2) |
| Example 27 | 17 | z55 (100) | SL-2/SL-4 60/40 | N-5/N-1 (7/7) | C-22 (0.8) | W-4 (2) |
| Example 28 | 5 | z23/z55 (40/40) | SL-1/SL-2 60/40 | N-1 (7) | C-23 (0.5) | W-2 (3) |
| Example 29 | 8 | z55 (80) | SL-1/SL-2 60/40 | N-1 (7) | C-24 (3.0) | W-1 (3) |
| Example 30 | 1 | z17 (80) | SL-2/SL-4 60/40 | N-1 (7) | C-25 (2.0) | W-4 (1) |
| Example 31 | 15 | z55/z65 (75/75) | SL-1/SL-2 60/40 | N-1 (7) | C-26 (2.0) | W-1 (1) |
| Example 32 | 17 | z2/z12 (40/50) | SL-1/SL-3 40/60 | N-1 (7) | C-27 (1.0) | W-1 (3) |
| Example 33 | 3 | z23/z15 (60) | SL-1/SL-2 60/40 | N-1 (7) | C-28 (1.0) | W-1 (3) |

TABLE 10-continued

| | | | | | | |
|---|---|---|---|---|---|---|
| Example 34 | 5 | z23 (80) | SL-1/SL-2 60/40 | N-1 (7) | C-29 (0.5) | W-4 (1) |
| Example 35 | 16 | z55/z51 (45/45) | SL-2/SL-4 60/40 | N-1 (10) | C-30 (0.7) | W-4 (2) |
| Example 36 | 15 | z23/z55 (40/40) | SL-2/SL-4 60/40 | N-1 (7) | C-31 (2.0) | W-2 (2) |
| Example 37 | 18 | z55 (100) | SL-2/SL-4 60/40 | N-1 (7) | C-32 (3.0) | W-2 (2) |
| Example 38 | 1 | z17 (80) | SL-1/SL-2 60/40 | N-1 (7) | C-33 (3.0) | W-1 (3) |
| Example 39 | 16 | z23/z9 (40/50) | SL-1/SL-2 60/40 | N-1 (7) | C-34 (1.0) | W-1 (3) |
| Example 40 | 17 | z4 (65) | SL-2/SL-4 60/40 | N-1 (7) | C-35 (1.0) | W-1 (3) |
| Example 41 | 17 | z55 (100) | SL-2/SL-4 60/40 | N-1 (10) | C-36 (0.5) | W-4 (2) |
| Example 42 | 16 | z55/z51 (45/45) | SL-2/SL-4 60/40 | N-1 (10) | C-37 (0.7) | W-4 (2) |

| | Evaluation Results | | | | | | | | |
|---|---|---|---|---|---|---|---|---|---|
| | Normal Exposure | | | | Immersion Exposure | | | | |
| | Normal Exposure | | When Allowed to Stand for 30 Minutes after Exposure | | Normal Immersion Exposure | | When Allowed to Stand for 30 Minutes after Exposure | | Followability of Water |
| | Profile | Collapse | Profile | Collapse | Profile | Collapse | Profile | Collapse | (mm/sec) |
| Example 21 | rectangular | 70 | rectangular | 72 | rectangular | 70 | rectangular | 74 | 250 |
| Example 22 | rectangular | 70 | rectangular | 70 | rectangular | 70 | rectangular | 71 | 250 |
| Example 23 | rectangular | 70 | rectangular | 72 | rectangular | 70 | rectangular | 73 | 250 |
| Example 24 | rectangular | 70 | rectangular | 70 | rectangular | 70 | rectangular | 71 | 250 |
| Example 25 | rectangular | 70 | rectangular | 70 | rectangular | 70 | rectangular | 70 | 250 |
| Example 26 | rectangular | 70 | rectangular | 72 | rectangular | 70 | rectangular | 73 | 250 |
| Example 27 | rectangular | 70 | rectangular | 70 | rectangular | 70 | rectangular | 70 | 250 |
| Example 28 | rectangular | 70 | rectangular | 70 | rectangular | 70 | rectangular | 70 | 250 |
| Example 29 | rectangular | 70 | rectangular | 72 | rectangular | 70 | rectangular | 73 | 250 |
| Example 30 | rectangular | 70 | rectangular | 70 | rectangular | 70 | rectangular | 70 | 250 |
| Example 31 | rectangular | 70 | rectangular | 70 | rectangular | 70 | rectangular | 70 | 200 |
| Example 32 | rectangular | 70 | rectangular | 70 | rectangular | 70 | rectangular | 71 | 250 |
| Example 33 | rectangular | 70 | rectangular | 70 | rectangular | 70 | rectangular | 70 | 250 |
| Example 34 | rectangular | 70 | rectangular | 70 | rectangular | 70 | rectangular | 71 | 250 |
| Example 35 | rectangular | 70 | rectangular | 70 | rectangular | 70 | rectangular | 70 | 250 |
| Example 36 | rectangular | 70 | rectangular | 72 | rectangular | 70 | rectangular | 73 | 250 |
| Example 37 | rectangular | 70 | rectangular | 72 | rectangular | 70 | rectangular | 72 | 250 |
| Example 38 | rectangular | 70 | rectangular | 72 | rectangular | 70 | rectangular | 72 | 250 |
| Example 39 | rectangular | 70 | rectangular | 70 | rectangular | 70 | rectangular | 70 | 250 |
| Example 40 | rectangular | 70 | rectangular | 70 | rectangular | 70 | rectangular | 71 | 250 |
| Example 41 | rectangular | 70 | rectangular | 70 | rectangular | 70 | rectangular | 70 | 250 |
| Example 42 | rectangular | 70 | rectangular | 70 | rectangular | 70 | rectangular | 70 | 250 |

TABLE 11

| | Composition | | | | | |
|---|---|---|---|---|---|---|
| | Resin (2 g) | Photoacid Generator (mg) | Solvent (mass ratio) | Basic Compound (mg) | Resin (C) (wt %) | Surfactant (mg) |
| Example 43 | 19 | z2 (80) | SL-2 100 | N-7 (7) | C-38 (0.5) | W-3 (2) |
| Example 44 | 20 | z2 (80) | SL-1 100 | N-7 (7) | C-39 (0.7) | W-1 (2) |
| Example 45 | 21 | z23/z74 (50/50) | SL-2/SL-5 60/40 | N-3 (6) | C-40 (0.5) | W-1 (2) |
| Example 46 | 22 | z2/z42 (50/40) | SL-2/SL-5 60/40 | N-3 (6) | C-41 (0.7) | W-1 (2) |
| Example 47 | 23 | z2 (80) | SL-2/SL-3 60/40 | N-7 (7) | C-42 (0.5) | W-1 (2) |
| Example 48 | 24 | z2/z15 (50/75) | SL-2/SL-3 60/40 | N-4 (6) | C-43 (0.7) | W-1 (3) |
| Example 49 | 25 | z30/z12 (50/75) | SL-2 100 | N-8 (7) | C-44 (0.5) | W-1 (2) |

| | Evaluation Results | | | | | | | | |
|---|---|---|---|---|---|---|---|---|---|
| | Normal Exposure | | | | Immersion Exposure | | | | |
| | Normal Exposure | | When Allowed to Stand for 30 Minutes after Exposure | | Normal Immersion Exposure | | When Allowed to Stand for 30 Minutes after Exposure | | Followability of Water |
| | Profile | Collapse | Profile | Collapse | Profile | Collapse | Profile | Collapse | (mm/sec) |
| Example 43 | rectangular | 70 | rectangular | 70 | rectangular | 70 | rectangular | 70 | 250 |
| Example 44 | rectangular | 70 | rectangular | 70 | rectangular | 70 | rectangular | 72 | 250 |
| Example 45 | rectangular | 70 | rectangular | 70 | rectangular | 70 | rectangular | 72 | 250 |
| Example 46 | rectangular | 70 | rectangular | 70 | rectangular | 70 | rectangular | 70 | 250 |
| Example 47 | rectangular | 70 | rectangular | 70 | rectangular | 70 | rectangular | 70 | 250 |
| Example 48 | rectangular | 70 | rectangular | 70 | rectangular | 70 | rectangular | 70 | 250 |
| Example 49 | rectangular | 70 | rectangular | 70 | rectangular | 70 | rectangular | 70 | 250 |

TABLE 12

| | Composition | | | | | | |
|---|---|---|---|---|---|---|---|
| | Resin (2 g) | Photoacid Generator (mg) | Solvent (mass ratio) | Basic Compound (mg) | Resin (C) (wt %) | Surfactant (mg) | Additive (H) (mg) |
| Example 50 | 23/25 (1/1) | z66/z78 (50/50) | SL-1/SL-2 60/40 | N-8 (7) | C-45 (0.5) | W-1 (2) | — |
| Example 51 | 16/17 (1/1) | z63 (90) | SL-2/SL-4 60/40 | N-1 (10) | C-46 (0.7) | W-4 (2) | — |
| Example 52 | 1 | z63 (90) | SL-2/SL-4 60/40 | N-1 (10) | C-37/C-46 (0.35/0.35) | W-1 (2) | — |
| Comparative Example 1 | 1 | z2 (80) | SL-4/SL-2 40/60 | N-5 (7) | — | — | — |
| Comparative Example 2 | 2 | z2 (80) | SL-4/SL-2 40/60 | N-5 (7) | — | W-1 (3) | — |
| Comparative Example 3 | 2 | z2 (80) | SL-4/SL-2 40/60 | N-5 (7) | — | W-2 (3) | — |
| Comparative Example 4 | 26 | z2 (80) | SL-4/SL-2 40/60 | N-5 (7) | — | W-1 (5) | — |
| Comparative Example 5 | 27 | z2 (80) | SL-4/SL-2 40/60 | N-5 (7) | — | W-1 (5) | — |
| Comparative Example 6 | 28 | z2 (80) | SL-4/SL-2 40/60 | N-5 (7) | C-1 (1.0) | W-1 (5) | — |
| Comparative Example 7 | 1 | z2 (80) | SL-4/SL-2 40/60 | N-5 (7) | — | W-1 (5) | H-1 (5) |
| Comparative Example 8 | 1 | z2 (80) | SL-4/SL-2 40/60 | N-5 (7) | — | W-1 (5) | H-2 (5) |

| | Evaluation Results | | | | | | | |
|---|---|---|---|---|---|---|---|---|
| | Normal Exposure | | | | Immersion Exposure | | | |
| | Normal Exposure | | When Allowed to Stand for 30 Minutes after Exposure | | Normal Immersion Exposure | | When Allowed to Stand for 30 Minutes after Exposure | | Followability of Water |
| | Profile | Collapse | Profile | Collapse | Profile | Collapse | Profile | Collapse | (mm/sec) |
| Example 50 | rectangular | 70 | rectangular | 70 | rectangular | 70 | rectangular | 70 | 250 |
| Example 51 | rectangular | 70 | rectangular | 70 | rectangular | 70 | rectangular | 70 | 250 |
| Example 52 | rectangular | 70 | rectangular | 70 | rectangular | 70 | rectangular | 70 | 250 |
| Comparative Example 1 | rectangular | 75 | T-top | 110 | rectangular | 75 | T-top | 110 | 50 |
| Comparative Example 2 | rectangular | 75 | T-top | 90 | rectangular | 100 | T-top | 110 | 50 |
| Comparative Example 3 | rectangular | 75 | T-top | 90 | rectangular | 75 | T-top | 110 | 50 |
| Comparative Example 4 | rectangular | 75 | T-top | 90 | rectangular | 75 | T-top | 110 | 50 |
| Comparative Example 5 | rectangular | 100 | T-top | 110 | rectangular | 100 | T-top | 130 | 50 |
| Comparative Example 6 | no image resolution | — | no image resolution | — | No image resolution | — | no image resolution | — | 250 |
| Comparative Example 7 | rectangular | 75 | T-top | 90 | rectangular | 75 | T-top | 110 | 50 |
| Comparative Example 8 | rectangular | 75 | T-top | 90 | rectangular | 75 | T-top | 110 | 50 |

The symbols in Tables 7 to 9 denote the followings.

The acid generators are corresponding to those described above.

N-1: N,N-Dibutylaniline
N-2: N,N-Dihexylaniline
N-3: 2,6-Diisopropylaniline
N-4: Tri-n-octylamine
N-5: N,N-Dihydroxyethylaniline
N-6: 2,4,5-Triphenylimidazole
N-7: Tris(methoxyethoxyethyl)amine
N-8: 2-Phenylbenzimidazole
W-1: Megafac F176 (produced by Dainippon Ink & Chemicals, Inc.) (fluorine-containing)
W-2: Megafac R08 (produced by Dainippon Ink & Chemicals, Inc.) (fluorine- and silicon-containing)
W-3: Polysiloxane polymer KP-341 (produced by Shin-Etsu Chemical Co., Ltd.) (silicon-containing)
W-4: Troysol S-366 (produced by Troy Chemical)
W-5: PF656 (produced by OMNOVA) (fluorine-containing)
W-6: PF6320 (produced by OMNOVA) (fluorine-containing)
W-7: PF6520 (produced by OMNOVA) (fluorine-containing)
SL-1: Cyclohexanone
SL-2: Propylene glycol monomethyl ether acetate
SL-3: Ethyl lactate
SL-4: Propylene glycol monomethyl ether
SL-5: γ-Butyrolactone
SL-6: Propylene carbonate

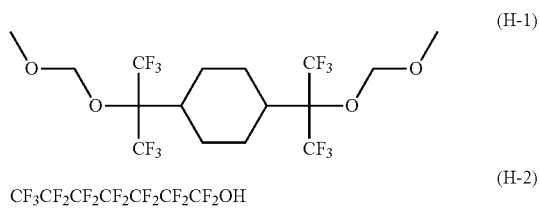

(H-1)

CF₃CF₂CF₂CF₂CF₂CF₂CF₂OH (H-2)

Additive (H-1) used in Comparative Example 7 and additive (H-2) used in Comparative Example 8 are compounds used for the comparison with the resin (C).

As seen from the results in Tables 9 to 12, the positive resist composition of the present invention ensures that collapse of the resist pattern and deterioration of the profile due to time delay between exposure and PEB less occur not only at the normal exposure but also at the immersion exposure and the followability for the immersion liquid at the immersion exposure is good.

When the exposure condition was changed to (3) to (6) below and the evaluations were conducted, the positive resist compositions of Examples 1 to 52 provided rectangular patterns as evaluated under the above mentioned exposure conditions (1) and (2).

(Exposure Condition (3))

A resist pattern was obtained by the same method as in Exposure Condition (1) except for setting the baking temperature after the coating of resist composition to 90° C. and setting the post-heating temperature after exposure to 110° C.

(Exposure Condition (4))

A resist pattern was obtained by the same method as in Exposure Condition (2) except for setting the baking temperature after the coating of resist composition to 90° C. and setting the post-heating temperature after exposure to 110° C.

(Exposure Condition (5))

A resist pattern was obtained by the same method as in Exposure Condition (1) except for coating the resist composition to form a 150-nm film, setting the post-heating temperature after exposure to 90° C., and setting the development time to 90 seconds.

(Exposure Condition (6))

A resist pattern was obtained by the same method as in Exposure Condition (2) except for coating the resist composition to form a 150-nm film, setting the post-heating temperature after exposure to 90° C., and setting the development time to 90 seconds.

According to the present invention, a positive resist composition improved in the collapse of resist pattern and the deterioration of profile due to time delay between exposure and PEB can be provided. Furthermore, a positive resist composition assured of good followability for the immersion liquid at the immersion exposure and suitable also for immersion exposure, a resin used for the positive resist composition, a compound used for the synthesis of the resin, and a pattern forming method using the positive resist composition can be provided.

The entire disclosure of each and every foreign patent application from which the benefit of foreign priority has been claimed in the present application is incorporated herein by reference, as if fully set forth.

What is claimed is:

1. A positive resist composition, which comprises:
(A) a resin of which solubility in an alkali developer increases under an action of an acid;
(B) a compound capable of generating an acid upon irradiation with actinic rays or radiation;
(C) a resin having at least one of a fluorine atom and a silicon atom; and
(D) a solvent,
wherein:
the amount added of the resin (C) is 0.1 to 6.0 mass %, based on the entire solids content of the positive resist composition,
the resin (C) is a linear polymer,
the resin (C) contains no ether group,
the resin (A) contains no fluorine atom or silicon atom, and
the resin (A) is a resin which has a monocyclic alicyclic hydrocarbon structure and decomposes under the action of an acid to increase its solubility in an alkali developer.

2. The positive resist composition according to claim 1, wherein in the resin (C), a total amount of repeating units having an alkali-soluble group or a group of which solubility in a developer increases under the action of an acid or an alkali is 20 mol % or less based on all repeating units constituting the resin (C).

3. The positive resist composition according to claim 1, wherein the weight average molecular weight of the resin (C) is 1,000 to 50,000.

4. The positive resist composition according to claim 1, further comprising at least one of a fluorine-containing surfactant and a silicon-containing surfactant.

5. The positive resist composition according to claim 1, wherein the compound (B) has a triphenylsulfonium structure.

6. The positive resist composition according to claim 1, wherein the resin (A) contains a lactone group.

7. The positive resist composition according to claim 1, wherein the resin (A) contains a lactone group represented by formula (LC1-4) or formula (LC1-5):

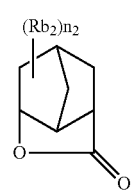

LC1-4

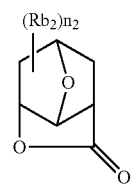

LC1-5 wherein $Rb_2$ represents an alkyl group having a carbon number of 1 to 8, a cycloalkyl group having a carbon number of 4 to 7, an alkoxy group having a carbon number of 1 to 8, an alkoxycarbonyl group having a carbon number of 1 to 8, a carboxyl group, a halogen atom, a hydroxyl group, a cyano group or an acid-decomposable group, and $n_2$ represents an integer of 0 to 4, and when $n_2$ is an integer of 2 or more, the plurality of $Rb_2$'s may be the same or different and the plurality of $Rb_2$'s may combine with each other to form a ring.

8. The positive resist composition according to claim 7, wherein the resin (A) contains a repeating unit represented by formula (A1):

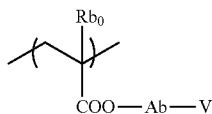

(AI)

wherein $Rb_0$ represents a hydrogen atom, a halogen atom or an alkyl group having a carbon number of 1 to 4,
Ab represents a linking group represented by $-Ab_1-CO_2-$, wherein $Ab_1$ is a methylene group, and
V represents a group represented by formulae (LC1-4) or (LC1-5).

9. The positive resist composition according to claim 1, wherein the resin (A) contains a repeating unit having an alicyclic hydrocarbon structure and not exhibiting acid decomposability.

10. The positive resist composition according to claim 1, wherein the resin (A) has no aromatic group.

11. The positive resist composition according to claim 1, wherein the resin (A) is a resin in which all repeating units comprise a (meth)acrylate-based repeating unit.

12. The positive resist composition according to claim 1, wherein the compound (B) is a compound represented by formula (ZI):

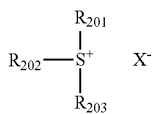

ZI wherein $R_{201}$, $R_{202}$ and $R_{203}$ each independently represents an organic group, and $X^-$ represents an organic anion represented by the following formula:

wherein $Rc_1$ represents an alkyl group with a 1-position being substituted by a fluorine atom or a fluoroalkyl group.

13. The positive resist composition according to claim 12, wherein $Rc_1$ is a group having an alicyclic group.

14. The positive resist composition according to claim 1, wherein the positive resist composition contains at least two of the compound (B), and
each of the compounds (B) is capable of generating an organic acid differing in a total atom number except for hydrogen atom by 2 or more from each other.

15. A pattern forming method, which comprises:
forming a resist film from a positive resist composition according to claim 1; and
exposing and developing the resist film.

16. The positive resist composition according to claim 1, wherein the resin (C) is a polymer consisting of a monomer containing only one addition polymerizable unsaturated bond.

17. The positive resist composition according to claim 1, wherein the resin (C) is a polymer consisting of a (meth) acrylic ester monomer containing only one addition polymerizable unsaturated bond.

18. The positive resist composition according to claim 1, wherein the resin (C) contains at least one repeating unit represented by any one of formula (C-Ia) to (C-Ic):

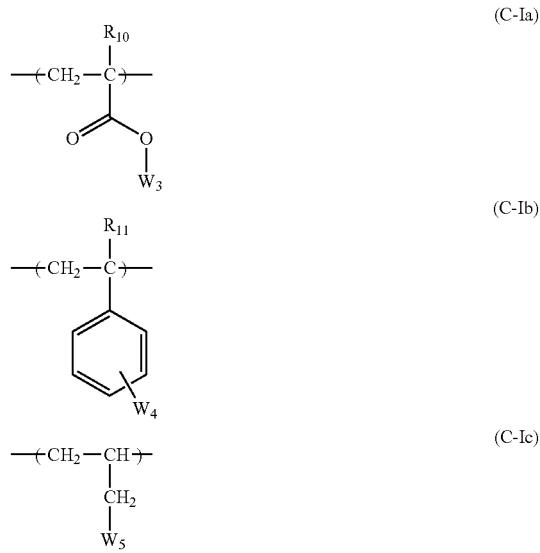

wherein in formulas (C-Ia) to (C-Ic), $R_{10}$ and $R_{11}$ each represents a hydrogen atom, a fluorine atom, a linear or branched alkyl group having a carbon number of 1 to 4, or a linear or branched fluorinated alkyl group having a carbon number of 1 to 4; and
$W_3$ to $W_5$ each represents a fluorinated branched alkyl group having 1 to 20 carbon atoms.

19. The positive resist composition according to claim 1, wherein the resin (C) contains hexafluoroisopropanol.

20. The positive resist composition according to claim 1, wherein the resin (C) has a weight average molecular weight calculated in terms of standard polystyrene of from 4800 to 15000.

21. The positive resist composition according to claim 1, wherein the amount added of the resin (C) is 0.2 to 3.0 mass % based on the total solid components.

22. The positive resist composition according to claim 1, wherein the amount added of the resin (C) is 0.3 to 2.0 mass % based on the total solid components.

23. A method for filtrating a composition comprising:
filtrating the composition using a filter,
wherein the composition contains:
(A) a resin of which solubility in an alkali developer increases under an action of an acid;
(B) a compound capable of generating an acid upon irradiation with actinic rays or radiation;
(C) a resin having at least one of a fluorine atom and a silicon atom; and
(D) a solvent,
wherein:
the amount added of the resin (C) is 0.1 to 6.0 mass %, based on the entire solids content of the positive resist composition,
the resin (C) is a linear polymer,
the resin (C) contains no ether group,
the resin (A) contains no fluorine atom or silicon atom, and
the resin (A) is a resin which has a monocyclic alicyclic hydrocarbon structure and decomposes under the action of an acid to increase its solubility in an alkali developer.

24. A resist film obtained by:
applying a resist composition onto a substrate; and
heating the substrate,
wherein the resist composition contains:
(A) a resin of which solubility in an alkali developer increases under an action of an acid;
(B) a compound capable of generating an acid upon irradiation with actinic rays or radiation;
(C) a resin having at least one of a fluorine atom and a silicon atom; and
(D) a solvent,
wherein:
the amount added of the resin (C) is 0.1 to 6.0 mass %, based on the entire solids content of the positive resist composition,
the resin (C) is a linear polymer,
the resin (C) contains no ether group,
the resin (A) contains no fluorine atom or silicon atom, and
the resin (A) is a resin which has a monocyclic alicyclic hydrocarbon structure and decomposes under the action of an acid to increase its solubility in an alkali developer.

* * * * *